US010584181B2

(12) United States Patent
Scheer et al.

(10) Patent No.: US 10,584,181 B2
(45) Date of Patent: Mar. 10, 2020

(54) METHODS OF MAKING AND USING MULTISPECIFIC ANTIBODY PANELS AND ANTIBODY ANALOG PANELS

(75) Inventors: Justin Scheer, San Francisco, CA (US); Richard L. Vandlen, Hillsborough, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/510,145

(22) PCT Filed: Dec. 3, 2010

(86) PCT No.: PCT/US2010/058958
§ 371 (c)(1),
(2), (4) Date: Sep. 19, 2012

(87) PCT Pub. No.: WO2011/069104
PCT Pub. Date: Jun. 9, 2011

(65) Prior Publication Data
US 2013/0017200 A1 Jan. 17, 2013

Related U.S. Application Data

(60) Provisional application No. 61/346,566, filed on May 20, 2010, provisional application No. 61/267,006, filed on Dec. 4, 2009.

(51) Int. Cl.
| C07K 16/46 | (2006.01) |
| C07K 16/30 | (2006.01) |
| C07K 16/28 | (2006.01) |
| C07K 16/32 | (2006.01) |
| A61K 39/00 | (2006.01) |

(52) U.S. Cl.
CPC .......... *C07K 16/468* (2013.01); *C07K 16/283* (2013.01); *C07K 16/2863* (2013.01); *C07K 16/32* (2013.01); *A61K 2039/505* (2013.01); *C07K 2317/31* (2013.01); *C07K 2317/55* (2013.01); *C07K 2317/73* (2013.01); *C07K 2317/75* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| 4,002,531 A | 1/1977 | Royer |
| 4,120,649 A | 10/1978 | Schechter |
| 4,179,337 A | 12/1979 | Davis et al. |
| 4,256,746 A | 3/1981 | Miyashita et al. |
| 4,275,149 A | 6/1981 | Litman et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,318,980 A | 3/1982 | Boguslaski et al. |
| 4,322,348 A | 3/1982 | Asai et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,415,732 A | 11/1983 | Caruthers et al. |
| 4,424,219 A | 1/1984 | Hashimoto et al. |
| 4,450,254 A | 5/1984 | Isley et al. |
| 4,458,066 A | 7/1984 | Caruthers et al. |
| 4,665,077 A | 5/1987 | Stringfellow et al. |
| 4,732,863 A | 3/1988 | Tomasi et al. |
| 4,737,456 A | 4/1988 | Weng et al. |
| 4,816,567 A | 3/1989 | Cabilly et al. |
| 4,943,533 A | 7/1990 | Mendelsohn et al. |
| 5,047,524 A | 9/1991 | Andrus et al. |
| 5,078,998 A | 1/1992 | Bevan et al. |

(Continued)

FOREIGN PATENT DOCUMENTS

| CN | 1668636 A | 9/2005 |
| EP | 0 599 274 A1 | 6/1994 |

(Continued)

OTHER PUBLICATIONS

Glennie, The Journal of Immunology, vol. 139, No. 7, p. 2367-2375, 1987.*
Paul, Fundamental Immunology, 3rd Edition, 1993, pp. 292-295.*
Bendig M. M. (Methods: A Companion to Methods in Enzymology, 1995; 8:83-93).*
Planque (FASEB J. vol. 17, p. 136-143, 2003).*
Lauterlein (Clin. Chem. Lab Med. (vol. 49, No. 5, p. 877-883, 2011).*
Schmidt (Int. J. Cancer, vol. 65, p. 538-546, 1996).*
Rudikoff et al. (Proceedings of the National Academy of Sciences USA, vol. 79, p. 1979-1983, 1982) (Year: 1982).*

(Continued)

*Primary Examiner* — Michael Allen
(74) *Attorney, Agent, or Firm* — Morrison & Foerster LLP

(57) ABSTRACT

Multispecific antibodies that specifically bind at least two different epitopes are provided. Structural variants of native antibodies (antibody analogs) are also provided. Also provided are multispecific antibodies and antibody analogs having a range of biological activities. Agonist and antagonist multispecific antibodies and agonist and antagonist antibody analogs are provided. Multispecific antibodies and antibody analogs conjugated with therapeutic and/or diagnostic agents are also provided, as are multispecific antibodies and antibody analogs conjugated with agents to increase in vivo half-life compared to multispecific antibodies and antibody analogs lacking such agents. In addition, methods of making multispecific antibodies and antibody analogs and compositions comprising multispecific antibodies and antibody analogs are provided. Therapeutic, research, and diagnostic uses of multispecific antibodies and antibody analogs are also provided.

30 Claims, 22 Drawing Sheets
Specification includes a Sequence Listing.

(56) References Cited

U.S. PATENT DOCUMENTS

| | | | |
|---|---|---|---|
| 5,091,178 A | 2/1992 | Hellstrom et al. |
| 5,114,721 A | 5/1992 | Cohen et al. |
| 5,166,322 A | 11/1992 | Shaw et al. |
| 5,183,884 A | 2/1993 | Kraus et al. |
| 5,187,098 A | 2/1993 | Malke et al. |
| 5,206,344 A | 4/1993 | Katre et al. |
| 5,208,020 A | 5/1993 | Chari et al. |
| 5,212,290 A | 5/1993 | Vogelstein et al. |
| 5,316,757 A | 5/1994 | Sherry et al. |
| 5,342,606 A | 8/1994 | Sherry et al. |
| 5,385,893 A | 1/1995 | Kiefer |
| 5,416,064 A | 5/1995 | Chari et al. |
| 5,428,155 A | 6/1995 | Sherry et al. |
| 5,457,090 A | 10/1995 | Scott et al. |
| 5,462,725 A | 10/1995 | Kiefer et al. |
| 5,480,968 A | 1/1996 | Kraus et al. |
| 5,480,990 A | 1/1996 | Kiefer et al. |
| 5,500,362 A | 3/1996 | Robinson et al. |
| 5,583,024 A | 12/1996 | McElroy et al. |
| 5,601,819 A | 2/1997 | Wong et al. |
| 5,635,483 A | 6/1997 | Pettit et al. |
| 5,641,870 A | 6/1997 | Rinderknecht et al. |
| 5,663,149 A | 9/1997 | Pettit et al. |
| 5,674,713 A | 10/1997 | McElroy et al. |
| 5,677,171 A | 10/1997 | Hudziak et al. |
| 5,700,670 A | 12/1997 | Yamagishi et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,739,294 A | 4/1998 | Kiefer et al. |
| 5,750,660 A | 5/1998 | Kiefer et al. |
| 5,766,897 A | 6/1998 | Braxton |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,804,396 A | 9/1998 | Plowman |
| 5,807,715 A | 9/1998 | Morrison et al. |
| 5,821,337 A | 10/1998 | Carter et al. |
| 5,834,456 A | 11/1998 | Kiefer et al. |
| 5,837,234 A | 11/1998 | Gentile et al. |
| 5,877,296 A | 3/1999 | Hamann et al. |
| 5,880,131 A | 3/1999 | Greenwald et al. |
| 5,891,996 A | 4/1999 | Mateo De Acosta Del Rio et al. |
| 5,985,265 A | 11/1999 | Kinstler et al. |
| 6,048,529 A | 4/2000 | Atassi et al. |
| 6,124,431 A | 9/2000 | Sakakibara et al. |
| 6,129,914 A | 10/2000 | Weiner et al. |
| 6,214,345 B1 | 4/2001 | Firestone et al. |
| 6,372,907 B1 | 4/2002 | Lee et al. |
| 6,399,743 B1 | 6/2002 | Majumdar |
| 6,407,213 B1 | 6/2002 | Carter et al. |
| 6,441,163 B1 | 8/2002 | Chari et al. |
| 6,511,663 B1* | 1/2003 | King ............... A61K 51/10 424/130.1 |
| 6,528,624 B1 | 3/2003 | Idusogie et al. |
| 6,541,543 B2 | 4/2003 | Harris et al. |
| 6,602,677 B1 | 8/2003 | Wood et al. |
| 6,673,580 B2 | 1/2004 | Koren et al. |
| 6,683,046 B1 | 1/2004 | Gately et al. |
| 6,753,165 B1 | 6/2004 | Cox et al. |
| 6,774,180 B2 | 8/2004 | Kozlowski et al. |
| 6,828,401 B2 | 12/2004 | Nho et al. |
| 6,884,874 B2 | 4/2005 | Eldridge et al. |
| 6,908,963 B2 | 6/2005 | Roberts et al. |
| 7,005,504 B2 | 2/2006 | Hsei et al. |
| 7,078,496 B2 | 7/2006 | Roberts et al. |
| 7,101,932 B2 | 9/2006 | Kozlowski |
| 7,112,324 B1 | 9/2006 | Dorken et al. |
| 7,122,636 B1 | 10/2006 | Hsei et al. |
| 7,235,641 B2 | 6/2007 | Kufer et al. |
| 7,262,276 B2 | 8/2007 | Huang et al. |
| 7,270,809 B2 | 9/2007 | Cox, III |
| 7,329,516 B2 | 2/2008 | Li et al. |
| 7,354,584 B2* | 4/2008 | Reed ............... C07K 16/244 424/133.1 |
| 7,521,541 B2 | 4/2009 | Eigenbrot et al. |
| 7,855,275 B2 | 12/2010 | Eigenbrot et al. |
| 2003/0078388 A1 | 4/2003 | Basey et al. |
| 2003/0096373 A1 | 5/2003 | Majumdar et al. |
| 2003/0096743 A1 | 5/2003 | Senter |
| 2003/0130189 A1 | 7/2003 | Senter et al. |
| 2003/0224397 A1 | 12/2003 | Lowman et al. |
| 2004/0001827 A1 | 1/2004 | Dennis |
| 2004/0001838 A1 | 1/2004 | Zhao et al. |
| 2004/0039176 A1 | 2/2004 | Widdison |
| 2004/0213791 A1* | 10/2004 | Bander ............ A61K 47/48638 424/155.1 |
| 2004/0229310 A1 | 11/2004 | Simmons |
| 2005/0048572 A1 | 3/2005 | Reilly et al. |
| 2005/0079184 A1* | 4/2005 | Hsing-Chang et al. ... 424/178.1 |
| 2005/0169933 A1 | 8/2005 | Steeves et al. |
| 2006/0013819 A1 | 1/2006 | Kelsey |
| 2006/0073142 A1 | 4/2006 | Chan et al. |
| 2006/0280747 A1 | 12/2006 | Fuh et al. |
| 2007/0059806 A1* | 3/2007 | Arnon ................ C12N 15/115 435/91.1 |
| 2007/0092940 A1* | 4/2007 | Eigenbrot et al. ........... 435/69.1 |
| 2007/0248604 A1 | 10/2007 | Desnoyers et al. |
| 2009/0035552 A1 | 2/2009 | Childs et al. |
| 2009/0041770 A1 | 2/2009 | Chamberlain et al. |
| 2009/0092582 A1 | 4/2009 | Bogin et al. |
| 2009/0098574 A1 | 4/2009 | Brisson et al. |
| 2009/0117100 A1 | 5/2009 | Mao et al. |
| 2009/0130114 A1 | 5/2009 | Qian et al. |
| 2009/0214541 A1* | 8/2009 | Gillies ................. C07K 16/32 424/136.1 |
| 2009/0285837 A1 | 11/2009 | Kao et al. |
| 2011/0256150 A1* | 10/2011 | Watts et al. ................ 424/158.1 |

FOREIGN PATENT DOCUMENTS

| | | |
|---|---|---|
| EP | 0404097 B1 | 9/1996 |
| EP | 0 340 109 B1 | 5/1997 |
| EP | 0 616 812 B1 | 11/1999 |
| EP | 0 659 439 B1 | 10/2001 |
| JP | 2007-516213 A | 6/2007 |
| JP | 2008-516896 A | 5/2008 |
| JP | 2009-525764 A | 7/2009 |
| JP | 2009-539836 A | 11/2009 |
| WO | 90/08187 A1 | 7/1990 |
| WO | 90/11294 A1 | 10/1990 |
| WO | 91/01133 A1 | 2/1991 |
| WO | 93/11161 A1 | 6/1993 |
| WO | 93/21319 A1 | 10/1993 |
| WO | 94/11026 A2 | 5/1994 |
| WO | 94/11026 A3 | 5/1994 |
| WO | 94/11026 R1 | 5/1994 |
| WO | 95/25167 A1 | 9/1995 |
| WO | 96/30347 A1 | 1/1996 |
| WO | WO-1996/01653 A1 | 1/1996 |
| WO | 96/03397 A1 | 2/1996 |
| WO | 96/16673 A1 | 6/1996 |
| WO | 96/33978 A1 | 10/1996 |
| WO | 96/33980 A2 | 10/1996 |
| WO | 96/40210 A1 | 12/1996 |
| WO | 97/04801 A1 | 2/1997 |
| WO | 97/35885 A1 | 10/1997 |
| WO | 97/38983 A1 | 10/1997 |
| WO | 98/02463 A1 | 1/1998 |
| WO | 98/43960 A1 | 10/1998 |
| WO | 98/45479 A1 | 10/1998 |
| WO | 98/50433 A2 | 11/1998 |
| WO | 98/50433 A3 | 11/1998 |
| WO | 99/03887 A1 | 1/1999 |
| WO | 99/06378 A1 | 2/1999 |
| WO | 99/06396 A1 | 2/1999 |
| WO | 99/09016 A1 | 2/1999 |
| WO | 99/19488 A1 | 4/1999 |
| WO | 99/64460 A1 | 12/1999 |

(56) References Cited

FOREIGN PATENT DOCUMENTS

| WO | WO-1999/66951 A2 | 12/1999 |
|---|---|---|
| WO | WO-1999/66951 A3 | 12/1999 |
| WO | 00/29004 A1 | 5/2000 |
| WO | 01/00245 A2 | 1/2001 |
| WO | 2001/024763 A2 | 4/2001 |
| WO | 2001/024763 A3 | 4/2001 |
| WO | 01/45746 A2 | 6/2001 |
| WO | 01/45746 A3 | 6/2001 |
| WO | 02/18444 A2 | 3/2002 |
| WO | 02/18444 A3 | 3/2002 |
| WO | 02/051870 A2 | 7/2002 |
| WO | 02/088172 A2 | 11/2002 |
| WO | 02/088172 A3 | 11/2002 |
| WO | 02/088172 R1 | 11/2002 |
| WO | 03/026577 A2 | 4/2003 |
| WO | 03/026577 A3 | 4/2003 |
| WO | 03/035694 A2 | 5/2003 |
| WO | 03/035694 A3 | 5/2003 |
| WO | 03/043583 A2 | 5/2003 |
| WO | 03/043583 A3 | 5/2003 |
| WO | WO-03/055914 A2 | 7/2003 |
| WO | WO-03/055914 A3 | 7/2003 |
| WO | 03/068144 A2 | 8/2003 |
| WO | 03/068144 A3 | 8/2003 |
| WO | 2004/01993 A1 | 12/2003 |
| WO | WO-2004/009618 A2 | 1/2004 |
| WO | WO-2004/009618 A3 | 1/2004 |
| WO | 04/016801 A2 | 2/2004 |
| WO | 04/016801 A3 | 2/2004 |
| WO | 04/032828 A2 | 4/2004 |
| WO | 04/032828 A3 | 4/2004 |
| WO | WO-2004/032961 A1 | 4/2004 |
| WO | WO-2005/014618 A2 | 2/2005 |
| WO | WO-2005/014618 A3 | 2/2005 |
| WO | WO-2005/026209 A2 | 3/2005 |
| WO | 2005/035572 A2 | 4/2005 |
| WO | 2005/035572 A3 | 4/2005 |
| WO | 2005/037992 A2 | 4/2005 |
| WO | 2005/081711 A2 | 9/2005 |
| WO | WO-2005/086612 A2 | 9/2005 |
| WO | WO-2005/086612 A3 | 9/2005 |
| WO | WO-2006/034488 A2 | 3/2006 |
| WO | WO-2007/145862 A2 | 12/2007 |
| WO | WO-2007/145862 A3 | 12/2007 |
| WO | WO-2007/145941 A2 | 12/2007 |
| WO | WO-2007/145941 A3 | 12/2007 |
| WO | WO-2008/140493 A2 | 11/2008 |
| WO | WO-2008/140493 A3 | 11/2008 |
| WO | WO-2009/012256 A1 | 1/2009 |
| WO | WO-2009/023270 A2 | 2/2009 |
| WO | WO-2009/023270 A3 | 2/2009 |
| WO | WO2010/048446 * | 4/2010 |
| WO | 2010/108127 A1 | 9/2010 |

OTHER PUBLICATIONS

Albert et al., "Direct synthesis of [DOTA-DPhe $^1$]-octreotide and [DOTA-DPhe $^1$,Tyr $^3$]-octreotide (SMT487): Two conjugates for systemic delivery of radiotherapeutical nuclides to somatostatin receptor positive tumors in man" Bioorg Med Chem Lett 8:1207-1210 ( 1998).
Amir et al., "Self-immmolative dendrimers" Angew. Chem. Int. Ed. 42:4494-4499 ( 2003).
Amsberry et al., "The lactonization of 2'-hydroxyhydrocinnamic acid amides: A potential prodrug for amines" J Org Chem 55:5867-5877 ( 1990).
Axworthy et al., "Cure of human carcinoma xenografts by a single dose of pretargeted yttrium-90 with negligible toxicity" P Natl Acad Sci USA 97(4):1802-1807 ( 2000).
Baeuerle and Reinhardt, "Bispecific T-cell engaging antibodies for cancer therapy" Cancer Res 69(12):4941-4944 ( 2009).
Balan et al., "Site-specific PEGylation of protein disulfide bonds using a three-carbon bridge" Bioconjugate Chem 18:61-76 ( 2007).

Bargou et al., "Tumor regression in cancer patients by very low doses of a T cell—engaging antibody" Science 321(5891):974-977 ( 2008).
Basic and Clinical Immunology (p. 71 and Chapter 6), Stites, Ten and Parslow, 8th edition, Norwalk, CT:Appleton & Lange, ( 1994).
Beaucage and Iyer, "Advances in the synthesis of oligonucleotides by the phosphoramidite approach" Tetrahedron 48(12):2223-2311 ( 1992).
Berg et al., "Bispecific antibodies that mediate killing of cells infected with human immunodeficiency virus of any strain" P Natl Acad Sci USA 88:4723-4727 (Jun. 1991).
Bergmann et al., "Evidence for cardiomyocyte renewal in humans" Science 324(5923):98-102 (Apr. 3, 2009).
Bernhard et al., "Cysteine analogs of recombinant barley ribosome inactivating protein form antibody conjugates with enhanced stability and potency in vitro" Bioconjug Chem 5:126-132 ( 1994).
Bersell et al., "Neuregulin 1/ErbB4 signaling induces cardiomyocyte proliferation and repair of heart injury" Cell 138(2):257-270 (Jul. 24, 2009).
Blend et al., "Labeling anti-HER2/neu monoclonal antibodies with $^{111}$In and $^{90}$Y using a bifunctional DTPA chelating agent" Cancer Biother Radio 18(3):355-363 ( 2003).
Bocharov et al., "Spatial structure of the dimeric transmembrane domain of the growth factor receptor ErbB2 presumably corresponding to the receptor active state" J Biol Chem 283(11):6950-6956 (Mar. 14, 2008).
Brennan et al., "Preparation of bispecific antibodies by chemical recombination of monoclonal immunoglobulin G $_1$ fragments" Science 229(4708):81-83 (Jul. 5, 1985).
Briggs and Panfili, "Quantitation of DNA and protein impurities in biopharmaceuticals" Anal Chem 63:850-859 ( 1991).
Briggs et al., "Synthesis of functionalised fluorescent dyes and their coupling to amines and amino acids" J Chem Soc, Perkin Trans 1:1051-1058 ( 1997).
Brinkley, M., "A brief survey of methods for preparing protein conjugates with dyes, haptens, and cross-linking reagents" Bioconj Chem 3:2-13 ( 1992).
Britsch et al., "The ErbB2 and ErbB3 receptors and their ligand, neuregulin-1, are essential for development of the sympathetic nervous system" Genes Dev 12:1825-1836 ( 1998).
Britsch, S., "The neuregulin-I/ErbB signaling system in development and disease" Adv Anat Embryol Cell Biol 190:1-65 ( 2007).
Brocchini et al., "Disulfide bridge based PEGylation of proteins" Adv Drug Delivery Rev 60(1):3-12 ( 2008).
Brufsky, A., "Trastuzumab-based therapy for patients with HER2-positive breast cancer" Am J Clin Oncol 33(2):186-195 (Apr. 2, 2010).
Buddelmeijer and Young, "The essential *Escherichia coli* apolipoprotein N-acyltransferase (Lnt) exists as an extracytoplasmic thioester acyl-enzyme intermediate" Biochem 49:341-346 ( 2010).
Bundy et al., "Site-specific incorporation of p-propargyloxyphenylalanine in a cell-free environment for direct protein-protein click conjugation" Bioconjugate Chem 21:255-263 ( 2010).
Burton, D., "Immunoglobulin G: Functional sites" Mol Immunol 22(3):161-206 ( 1985).
Camera et al., "Comparative biodistribution of indium- and yttrium-labeled B3 monoclonal antibody conjugated to either 2-(p-SCN-Bz)-6-methyl-DTPA (1B4M-DTPA) or 2-(p-SCN-Bz)-1,4,7,10-tetraazacyclododecane tetraacetic acid (2B-DOTA)" Eur J Nucl Med 21(7):640-646 ( 1994).
Camera et al., "Evaluation of a new DTPA-derivative chelator: Comparative biodistribution and imaging studies of $^{111}$in-labeled B3 monoclonal antibody in athymic mice bearing human epidermoid carcinoma xenografts" Nucl Med Biol 20(8):955-962 ( 1993).
Capel et al., "Heterogeneity of human IgG Fc receptors" Immunomethods 4:25-34 ( 1994).
Carpenter, G., "Receptors for epidermal growth factor and other polypeptide mitogens" Ann Rev Biochem 56:881-914 ( 1987).
Carrico et al., "Introducing genetically encoded aldehydes into proteins" Nature Chem Biol 3(6):321-322 (Jun. 2007).
Carter and Senter, "Antibody-drug conjugates for cancer therapy" Cancer J 14(3):154-169 ( 2008).

(56) References Cited

OTHER PUBLICATIONS

Carter et al., "High level *Escherichia coli* expression and production of a bivalent humanized antibody fragment" Bio/Technology 10(2):163-167 (Feb. 1992).
Carter et al., "Improved oligonucleotide site-directed mutagenesis Using M 13 vectors" Nucl Acids Res 1312):4431-4443 ( 1985).
Casalini et al., "Role of HER receptors family in development and differentiation" J Cell Physiol 200:343-350 ( 2004).
Chames et al., "Bispecific antibodies for cancer therapy" Curr Opin Drug Disco Devel 12(2):276-283 ( 2009).
Chames et al., "Themed Section: Vector Design and Drug Delivery Review; Therapeutic antibodies: successes, limitations and hopes for the future" Brit J Pharmacol 157(2):220-233 ( 2009).
Chatal Monoclonal Antibodies in Immunoscintigraphy (CRC Press), ( 1989).
Chen et al., "MicroPET and autoradiographic imaging of breast cancer a $_v$-integrin expression using $^{18}$F- and $^{64}$Cu-labeled RGD peptide" Bioconj Chem 15:41-49 ( 2004).
Chen et al., "Selection and analysis of an optimized anti-VEGF antibody: Crystal structure of an affinity-matured Fab in complex with antigen" J Mol Biol 293:865-881 ( 1999).
Chien, K., "Herceptin and the heart—A molecular modifier of cardiac failure" N Engl J Med 354(8):789-790 (Feb. 23, 2006).
Cho et al. et al., "Structure of the extracellular region of HER2 alone and in complex with the Herceptin Fab" Nature 421:756-760 (Feb. 13, 2003).
Chothia and Lesk, "Canonical structures for the hypervariable regions of immunoglobulins" J Mol Biol 196(4):901-917 ( 1987).
Clackson et al., "Making antibody fragments using phage display libraries" Nature 352:624-628 (Aug. 15, 1991).
Clynes et al., "Fc receptors are required in passive and active immunity to melanoma" P Natl Acad Sci USA 95(2):652-656 (Jan. 1998).
Cree et al., "Methotrexate chemosensitivity by ATP luminescence in human leukemia cell lines and in breast cancer primary cultures: comparison of the TCA-100 assay with a clonogenic assay" Anti-cancer Drugs 6:398-404 ( 1995).
Crouch et al., "The use of ATP bioluminescence as a measure of cell proliferation and cytotoxicity" J Immunol Methods 160:81-88 ( 1993).
Daeron, M., "Fc receptor biology" Annu Rev Immunol 15:203-234 ( 1997).
Das and Suresh, "Producing bispecific and bifunctional antibodies" Methods Mol Med 109:329-345 ( 2005).
Davies and Riechmann, "Camelising' human antibody fragments: NMR studies on VH domains" FEBS Lett 339:285-290 ( 1994).
Davis, M., "The first targeted delivery of siRNA in humans via a self-assembling, cyclodextrin polymer-based nanoparticle: from concept to clinic" Mol Pharm 6(3):659-668 ( 2009).
de Graaf et al., "Nonnatural amino acids for site-specific protein conjugation" Bioconjugate Chem 20(7):1281-1295 (Jul. 2009).
De Haas et al., "Fcγ receptors of phagocytes" J Lab Clin Med 126:330-341 (Oct. 1995).
DeNardo et al., "Comparison of 1,4,7,10-tetraazacyclododecane-N,N', N', N'''-tetraacetic acid (DOTA)-Peptide-ChL6, a novel immunoconjugate with catabolizable linker, to 2-iminothiolane-2[p-(bromoacetamido)benzyl]-DOTA-ChL6 in breast cancer xenografts" Clin Cancer Res 4:2483-2490 (Oct. 1998).
Dennis et al., "Albumin binding as a general strategy for improving the pharmacokinetics of proteins" J Biol Chem 277(38):35035-35043 (Sep. 20, 2002).
Dillon et al., "Structural and functional characterization of disulfide isoforms of the human IgG subclass" J Biol Chem 283(23):16206-16215 (Jun. 6, 2008).
Dimitrov and Marks, "Therapeutic antibodies: Current state and future trends—Is a paradigm change coming soon?" Methods Mol Biol 525:1-27 ( 2009).
Doggen et al., "Ventricular ErbB2/ErbB4 activation and down-stream signaling in pacing-induced heart failure" J Mol Cell Cardiol 46:33-38 ( 2009).

Dooley and Flajnik, "Antibody repertoire development in cartilaginous fish" Developmental and Comparative Immunol 30:43-56 ( 2006).
Doppalapudi et al., "Chemically programmed antibodies: endothelin receptor targeting covX-bodies" Biorg and Med Chem Lett 17(2):501-506 ( 2007).
Doronina et al., "Development of potent monoclonal antibody auristatin conjugates for cancer therapy" Nat Biotechnol 21(7):778-784 (Jul. 2003).
Drakeman et al., "Bispecific antibodies for the treatment of tumours and infectious diseases" Expert Opin Investig Drugs 6(9):1169-1178 ( 1997).
D'Souza and Taylor-Papadimitriou, "Overexpression of ERBB2 in human mammary epithelial cells signals inhibition of transcription of the E-cadherin gene" P Natl Acad Sci USA 91(15):7202-7206 (Jul. 1994).
Dubowchik and Radia, "Monomethoxytrityl (MMT) as a versatile amino protecting group for complex prodrugs of anticancer compounds sensitive to strong acids, bases and nucleophiles" Tetrahedron Lett 38(30):5257-5260 ( 1997).
Erickson et al., "ErbB3 is required for normal cerebellar and cardiac development: a comparison with ErbB2- and heregulin-deficient mice" Development 124:4999-5011 ( 1997).
Ernst et al., "Isolation and characterization of the B-cell marker CD20" Biochem 44:15150-15158 ( 2005).
Falls, D., "Neuregulins and the neuromuscular system: 10 years of answers and questions" J Neurocytol 32:619-647 ( 2003).
Falls, D., "Neuregulins: functions, forms, and signaling strategies" Exp Cell Res 284:14-30 ( 2003).
Fanger et al., "Bispecific antibodies and targeted cellular cytotoxicity" Immunol Today 12(2):51-54 ( 1991).
Fanger et al., "Bispecific Antibodies" Crit Rev Immunol 12(3,4):101-124 ( 1992).
Fendly et al., "Characterization of murine monoclonal antibodies reactive to either the human epidermal growth factor receptor or HER2/neu gene product" Cancer Res 50:1550-1558 (Mar. 1, 1990).
Fischer and Leger, "Bispecific antibodies: Molecules that enable novel therapeutic strategies" Pathobiology 74:3-14 ( 2007).
Fraker et al., "Protein and cell membrane iodinations with a sparingly soluble chloroamide, 1,3,4,6-tetrachloro-3a,6a-diphenylglycoluril" Biochem Biophys Res Comm 80(4):849-857 (Feb. 28, 1978).
Francisco et al., "cAC10-vcMMAE, an anti-CD30 monomethyl auristatin E conjugate with potent and selective antitumor activity" Blood 102(4):1458-1465 (Aug. 15, 2003).
Franklin et al., "Insights into ErbB signaling from the structure of the ErbB2-pertuzumab complex" Cancer Cell 5:317-328 (Apr. 2004).
Freedman and Ginsburg, "Novel—and 'Neu'-therapeutic possibilities for heart failure" J Am Coll Cardiol 48(7):1448-1450 ( 2006).
Frisch et al., "Synthesis of short polyoxyethylene-based heterobifunctional cross-linking reagents. Application to the coupling of peptides to liposomes" Bioconj Chem 7:180-186 ( 1996).
Funderburgh et al., "Synthesis of corneal keratan sulfate proteoglycans by bovine keratocytes in vitro" J Biol Chem 271(49):31431-31436 (Dec. 6, 1996).
Garman, Non-Radioactive Labelling: A Practical Approach, London:Academic Press pp. 55 (1997).
Gavrilyuk et al., "An efficient chemical approach to bispecific and antibodies and antibodies of high valency" Biorg & Med Chem Lett 19:3716-3720 ( 2009).
Gazzano-Santoro et al., "A non-radiative complement-dependent cytotoxicity assay for anti-CD20 monoclonal antibody" J Immunol Methods 202:163-171 ( 1997).
Getz et al., "A comparison between the sylfhydryl reductants tris(2-carboxyethyl)phosphine and dithiothreitol for use in protein biochemistry" Anal Biochem 273:73-80 ( 1999).
Glading et al., "Epidermal growth factor receptor activation of Calpain is required for fibroblast motility and occurs via an ERK/MAP kinase signaling pathway" J Biol Chem 275(4):2390-2398 (Jan. 28, 2000).

(56) References Cited

OTHER PUBLICATIONS

Glennie et al., "Preparation and performance of biospecific F(60 β'γ) $_2$ antibody containing thioether-linked Faβ'γ fragments [1]" J Immunol 139(7):2367-2375 (Oct. 1, 1987).
Goodson et al. et al., "Site-directed Pegylation of Recombinant Interleukin-2 and Its Glycosylation Site" Bio-Technol 8:343-346 (Apr. 1990).
Graziano and Guptill, "Chemical production of bispecific antibodies" Methods Mol Biol 283:71-85 ( 2004).
Graziano et al., "Construction and characterization of a humanized anti-γ-Ig receptor Type I (FcγRI) monoclonal antibody" J Immunol 155:4996-5002 ( 1995).
Guyer et al., "Immunoglobulin binding by mouse intestinal epithelial cell receptors" J Immunol 117(2):587-593 (Aug. 1976).
Hamers-Casterman et al., "Naturally occurring antibodies devoid of light chains" Nature 363:446-448 (Jun. 3, 1993).
Haugland Molecular Probes Handbook of Fluorescent Probes and Research ChemicalsMolecular Probes, Inc., ( 2003).
Hay et al., "A 2-nitroimidazole carbamate prodrug of 5-amino-1-(chloromethyl)-3-[(5,6,7-trimethoxyindol-2-YL)carbonyl]-1,2-dihydro-3H-benz[E]indole (amino-seco-DB1-TMI) for use with ADEPT and GDEPT" Bioorg Med Chem Lett 9:2237-2242 ( 1999).
Hermanson, G., Bioconjugate Techniques (Academic Press, San Diego, CA),:40-55 and 643-671 ( 1996).
Higuchi, R. PCR Protocols: A Guide to Methods and Applications "Recombinant PCR" (Chapter 22), Innis et al.,Academic Press, Inc.,:177-183 ( 1990).
Hinman et al., "Preparation and characterization of monoclonal antibody conjugates of the calicheamicins: A novel and potent family of antitumor antibiotics" Cancer Res 53:3336-3342 (Jul. 15, 1993).
Hnatowich et al., "Protein labelling via deoxyribonucleic acid hybridization" Nucl Med Commun 17(1):66-75 ( 1996).
Hnatowich et al., "The preparation of DTPA-coupled antibodies radiolabeled with metallic radionuclides: an improved method" J Immunol Methods 65:147-157 ( 1983).
Ho et al., "Site-directed mutagenesis by overlap extension using the polymerase chain reaction" Gene 77:51-59 ( 1989).
Hollander et al., "Bispecific antibodies for cancer therapy" Immunotherapy 1(2):211-222 ( 2009).
Holliger et al., "'Diabodies': Small bivalent and bispecific antibody fragments" P Natl Acad Sci USA 90:6444-6448 (Jul. 1993).
Holt et al., "Domain antibodies: proteins for therapy" Trends Biotechnol 21(11):484-490 (Nov. 2003).
Horgan et al., "Studies on antigen binding by intact and hinge-deleted chimeric antibodies" J Immunol 150(12):5400-5407 (Jun. 15, 1993).
Hseih-Ma et al., "In vitro cytotoxic targeting by human mononuclear cells and bispecific antibody 2B1, recognizing c-erbB-2 protooncogene product and Fcγ receptor III" Cancer Res 52:6832-6839 (Dec. 15, 1992).
Hudziak et al., "Increased expression of the putative growth factor receptor p185 $^{HER2}$ causes transformation and tumorigenesis of NIH 3T3 cells" P Natl Acad Sci USA 84:7159-7163 (Oct. 1987).
Hudziak et al., "p185 $^{HER2}$ monoclonal antibody has antiproliferative effects in vitro and sensitizes human breast tumor cells to tumor necrosis factor" Mol Cell Biol 9(3):1165-1172 (Mar. 1989).
Humphrey et al., "Anti-synthetic peptide antibody reacting at the fusion junction of deletion-mutant epidermal growth factor receptors in human glioblastoma" P Natl Acad Sci USA 87:4207-4211 (Jun. 1990).
Issell and Crooke, "Maytansine" Cancer Treat Rev 5:199-207 ( 1978).
Ito et al., "A general method for introducing a series of mutations into cloned DNA using the polymerase chain reaction" Gene 102:67-70 ( 1991).
Izard et al., "An improved method for labeling monoclonal antibodies with samarium-153: Use of the bifunctional chelate 2-(p-isothiocyanatobenzyl)-6-methyldiethylenetriamianepentaacetic acid" Biocon Chem 3:346-350 ( 1992).

Jackman et al., "Development of a two-part strategy to identify a therapeutic human bispecific antibody that inhibits IgE receptor signaling" J Biol Chem 285(27):20850-20859 (Jul. 2, 2010).
Jackson et al., "Blockade of epidermal growth factor- or heregulin-dependent ErbB2 activation with the Anti-ErbB2 monoclonal antibody 2C4 has divergent downstream signaling and growth effects" Cancer Res 64(7):2601-2609 ( 2004).
Janeway et al. Immunobiology 5th edition, New York:Garland Publishing,:627-628 ( 2001).
Janeway, C., "Immunotherapy by peptides?" Nature 341:482-483 (Oct. 12, 1989).
Johnson et al. Methods in Molecular Biology "The Kabat Database and a Bioinformatics Example" Lo, Totowa, NJ:Hurnan Press, vol. 248:11-25 ( 2003).
Jones and Stern, "Expression of dominant-negative ErbB2 in the mammary gland of transgenic mice reveals a role in lobuloalveolar development and lactation" Oncogene 18:3481-3490 ( 1999).
Jones et al., "Replacing the complementarity-determining regions in a human antibody with those from a mouse" Nature 321:522-525 (May 29, 1986).
Junttila et al., "Ligand-independent HER2/HER3/PI3K complex is disrupted by trastuzumab and is effectively inhibited by the PI3K inhibitor GDC-0941" Cancer Cell 15:429-440 ( 2009).
Junutula et al., "Rapid identification of reactive cysteine residues for site-specific labeling of antibody-Fabs" J Immunol Methods 332:41-52 ( 2008).
Junutula et al., "Site-specific conjugation of a cytotoxic drug to an antibody improves the therapeutic index" Nat Biotechnol 26(8):925-32 (Aug. 2008).
Kabat et al. Sequences of Proteins of Immunological Interest 5th edition,NIH,:2 pages ( 1991).
Karpovsky et al., "Production of target-specific effector cells using hetero-cross-linked aggregates containing anti-target cell and anti-Fcγ receptor antibodies" J Experimental Med 160:1686-1701 (Dec. 1984).
Kaushik et al., "CDP-870 (certolizumab) in rhematoid arthritis" Expert Opin Biol Ther 5(4):601-606 ( 2005).
Khaw et al., "Bispecific enzyme-linked signal-enhanced immunoassay with subattomole sensitivity" Assay and Drug Dev Technol 3(3):319-327 ( 2005).
Khaw et al., "Imaging experimental atherosclerotic lesions in ApoE knockout mice: enhanced targeting with Z $_2$D $_3$-anti-DTPA bispecific antibody and $^{99m}$Tc-labeled negatively charged polymers" J Nucl Med 47(5):868-876 (May 2006).
Kim et al., "Localization of the site of the murine IgG1 molecule that is involved in binding to the murine intestinal Fc receptor" Eur J Immunol 24:2429-2434 ( 1994).
King et al., "Facile synthesis of maleimide bifunctional linkers" Tetrahedron Lett 43:1987-1990 ( 2002).
Kingsbury et al., "A novel peptide delivery system involving peptidase activated prodrugs as antimicrobial agents. Synthesis and biological activity of peptidyl derivatives of 5-fluorouracil" J Med Chem 27:1447-1451 ( 1984).
Kito et al., "Mass spectrometry-based approaches toward absolute quantitative proteomics" Curr Genomics 9(4):263-274 ( 2008).
Klussman et al., "Secondary mAb-vcMMAE conjugates are highly sensitive reporters of antibody internalization via the lysosome pathway" Bioconjugate Chem 15:765-773 ( 2004).
Knight, C., "Fluorimetric Assays of Proteolytic Enzymes" Methods Enzymol 248:18-34 ( 1995).
Kobayashi et al., "Evaluation of the in vivo biodistribution of indium-1 1 1 and yttrium-88 labeled dendrimer-1B4M-DTPA and its conjugation with anti-Tac monoclonal antibody" Bioconj Chem 10:103-111 ( 1999).
Kobayashi et al., "Evaluation of the in vivo biodistribution of yttrium-labeled isomers of CHX-CTPA-conjugated monoclonal antibodies" J. Nucl. Med 39:829-836 ( 1998).
Kohler and Milstein, "Continuous cultures of fused cells secreting antibody of predefined specificity" Nature 256:495-497 (Aug. 7, 1975).
Kolb et al., "Click Chemistry: Diverse chemical function from a few good reactions" Angew. Chem. Int. Ed. 40:2004-2021 ( 2001).

(56) References Cited

OTHER PUBLICATIONS

Kontermann et al., "Production of recombinant biscpecific antibodies" Methods Mol Biol 248:227-242 ( 2004).
Kontermann, R., "Recombinant bispecific antibodies for cancer therapy" Acta Pharmacologica Sinica 26(1):1-9 (Jan. 2005).
Kostelny et al., "Formation of a bispecific antibody by the use of leucine zippers" J Immunol 148(5):1547-1553 (Mar. 1, 1992).
Kotts et al., 'Differential growth inhibition of human carcinoma cells exposed to monoclonal antibodies directed against the extracellular domain of the HER2/ERBB2 protooncogene' In Vitro (Abstract #176) 26(3):59A (1990).
Kraeber-Bodere et al., "Radioimmunotherapy in medullary thyroid cancer using bispecific antibody and iodine 131-labeled bivalent hapten: preliminary results of a phase I/II clinical trial" Clin. Cancer Res 5(Suppl.):3190S-3198S (Oct. 1999).
Kraus et al., "Isolation and characterization of ERBB3, a third member of the ERBB/epidermal growth factor receptor family: Evidence for overexpression in a subset of human mammary tumors" P Natl Acad Sci USA 86:9193-9197 (Dec. 1989).
Kriangkum et al., "Bispecific and bifunctional single chain recombinant antibodies" Biomol Eng 18(1):31-40 (Aug. 2001).
Kukis et al., "Optimized conditions for chelation of yttrium-90-DOTA immunoconjugates" J Nucl Med 39:2105-2110 ( 1998).
Kumar et al., "New Insights into anti-HER-2 receptor monoclonal antibody research" Semin Oncol 27(6 Suppl 1 1):84-91 ( 2000).
Kumar et al., "Regulation of phosphorylation of the c-erbB-2/HER2 gene product by a monoclonal antibody and serum growth factor(s) in human mammary carcinoma cells" Mol Cell Biol 1 1(2):979-986 (Feb. 1991).
Kunkel, T., "Rapid and efficient site-specific mutagenesis without phenotypic selection" P Natl Acad Sci USA 82:488-492 (Jan. 1985).
Langer et al., "Capture of endothelial progenitor cells by a bispecific protein/monoclonal antibody molecule induces reendothelialization of vascular lesions" J. Mol Med 88:687-699 ( 2010).
Lee et al., "Antibody targeting of stem cells to infarcted myocardium" Stem Cells 25:712-717 ( 2007).
Lee et al., "Requirement for neuregulin receptor erbB2 in neural and cardiac development" Nature 378:394-398 (Nov. 23, 1995).
Lee et al., "Specific localization, gamma camera imaging, and intracellular trafficking of radiolabelled chimeric anti-$G_{D3}$ ganglioside monoclonal antibody KM871 in SK-MEL-28 melanoma xenografts" Cancer Res 61:4474-4482 ( 2001).
Lee-Hoeflich et al., "A central role for HER3 in HER2-amplified breast cancer: implications for targeted therapy" Cancer Res 68(14):5878-87 (Jul. 15, 2008).
Leone et al., "Expression of the c-ErbB-2/HER2 proto-oncogene in normal hematopoietic cells" J Leukoc Biol 74:593-601 (Oct. 2003).
Leu et al., "Erbb2 regulates neuromuscular synapse formation and is essential for muscle spindle development" Development 130(1 1):2291-2301 ( 2003).
Lewis et al., "Differential responses of human tumor cell lines to anti-p185[HER2] monoclonal antibodies" Cancer Immunol Immunother 37:255-263 ( 1993).
Lewis et al., "Growth regulation of human breast and ovarian tumor cells by heregulin: Evidence for the requirement of ErbB2 as a critical component in mediating heregulin responsiveness" Cancer Res 56:1457-1465 (Mar. 15, 1996).
Lewis et al., "Maleimidocysteineamido-DOTA derivatives: New reagents for radiometal chelate conjugation to antibody sulthydryl groups undergo pH-dependent cleavage reactions" Bioconj Chem 9:72-86 ( 1998).
Li et al., "Improved biodistribution and radioimmunoimaging with Poly(ethylene glycol)-DOTA-conjugated anti-CEA diabody" Bioconjugate Chem 17:68-76 ( 2006).
Lin et al., "Aberrant development of motor axons and neuromuscular synapses in erbB2-deficient mice" P Natl Acad Sci USA 97(3):1299-1304 (Feb. 1, 2000).
Lindmark et al., "Binding of immunoglobulins to protein A and immunoglobulin levels in mammalian sera" J Immunol Methods 62:1-13 ( 1983).

Liu and Wang, "Identification of active site residues in the 'GyrA' half of yeast DNA topoisomerase II" J Biol Chem 273(32):20252-20260 (Aug. 7, 1998).
Liu et al., "Adding new chemistries to the genetic code" Annu Rev Biochem 79:413-444 ( 2010).
Lode et al., "Targeted therapy with a novel tnediyene antibiotic calicheamicin $\Theta^1{}_1$ effectively suppresses growth and dissemination of liver metastases in a syngeneic model of murine neuroblastoma" Cancer Res 58:2925-2928 (Jul. 15, 1998).
Lowman and Wells, "Monovalent phage display: A method for selecting variant proteins from random libraries" Methods: A Companion to Methods in Enzymology 3(3):205-216 (Dec. 1991).
Lowman et al., "Mutational analysis and protein engineering of receptor-binding determinants in human placental lactogen" J Biol Chem 266(17):10982-10988 (Jun. 15, 1991).
Lum et al., "Induction of immune responses and improved survival after infusions of T cells armed with anti-CD3 X anti-Her2/Neu bispecific antibody in stage IV breast cancer patients" Blood (ASH Annual Meeting Abstracts) 110:2747 ( 2007).
Lund et al., "Expression and characterization of truncated forms of humanized L243 IgG 1. Architectural features can influence synthesis of its oligosaccharide chains and affect superoxide production triggered through human Fcγ receptor I" Eur J Biochem 267:7246-7256 ( 2000).
Malmborg and Borrebaeck, "BIAcore as a tool in antibody engineering" J Immunol Methods 183:7-13 ( 1995).
Mardirossian et al., "The stability in liver homogenates of indium-111 and yttrium-90 attached to antibody via two popular chelators" Nucl Med Biol 20(1):65-74 ( 1993).
Marks et al., "By-passing immunization. Human antibodies from V-gene libraries displayed on phage" J Mol Biol 222:581-597 ( 1991).
(Marvin and Zhu, "Bispecific antibodies for dual-modality cancer therapy: killing two signaling cascades with one stone" Curr Opin Drug Discov Delev 9(2):184-193 ( 2006).
Marvin and Zhu, "Recombinant approaches to IgG-like bispecific antibodies" Acta Pharmacologica Sinica 26(6):649-658 (Jun. 2005)
Means and Feeney, "Chemical modifications of proteins: History and applications" Bioconj Chem 1:2-12 ( 1990).
Meares et al., "Conjugation of antibodies with bifunctional chelating agents: Isothiocyanate and bromoacetamide reagents, methods of analysis, and subsequent addition of metal ions" Anal Biochem 142:68-78 ( 1984).
Meares et al., "Macrocyclic chelates of radiometals for diagnosis and therapy" Br J Cancer 62( Suppl X):21-26 ( 1990).
Miederer et al., "Pharmacokinetics, dosimetry, and toxicity of the targetable atomic generator, $^{225}$Ac-HuM195, in nonhuman primates" J Nucl Med 45:129-137 ( 2004).
Miller et al., "Design, construction, and in vitro analyses of multivalent antibodies" J Immunol 170:4854-4861 ( 2003).
Miraglia et al., "Homogeneous cell- and bead-based assays for high throughput screening using fluorometric microvolume assay technology" J Biomol Screening 4(4):193-204 ( 1999).
Mirzadeh et al., "Radiometal labeling of immunoproteins: Covalent linkage of 2-(4-isothiocyanatobenzyl)diethylenetriaminepentaacetic acid ligands to immunoglobulin" Bioconj Chem 1:59-65 ( 1990).
Mitchell et al., "Targeting primary human Ph $^+$B-cell precursor leukemia-engrafted SCID mice using radiolabeled anti-CD19 monoclonal antibodies" J Nucl Med 44:1105-1112 ( 2003).
Morimoto and Inouye, "Method for the preparation of bispecific F(ab')2 μ fragments from mouse monoclonal antibodies of the immunoglobulin M class and characterization of the fragments" J. Immunol Methods 224:43-50 ( 1999).
Morimoto et al., "Single nucleotide polymorphism in fibroblast growth factor receptor 4 at codon 388 is associated with prognosis in high-grade soft tissue sarcoma" Cancer 98(10):2245-50 ( 2003).
Morris et al., "Anthracyclines and trastuzumab; getting to the heart of the matter: when getting to the heart is the matter" Breast Cancer Res Treat 127:585-586 ( 2011).
Morris et al., "Rescue of the cardiac defect in ErbB2 mutant mice reveals essential roles of ErbB2 in peripheral nervous system development" Neuron 23:273-283 (Jun. 1999).

(56) References Cited

OTHER PUBLICATIONS

Morrison et al., "Chimeric human antibody molecules: Mouse antigen-binding domains with human constant region domains" P Natl Acad Sci USA 81:6851-6855 (Nov. 1984).
Murakami et al. The Molecular Basis of Cancer "Cell cycle regulation, oncogenes, and antineoplastic drugs" (Chapter 1), Mendelsohn and Israel, Philadelphia:WB Saunders, ( 1995).
Murthy et al., "Binding of an antagonistic monoclonal antibody to an intact and fragmented EGF-receptor polypeptide" Arch Biochem Biophys 252(2):549-560 (Feb. 1, 1987).
Muyldermans et al., "Recognition of antigens by single-domain antibody fragments: the superfluous luxury of paired domains" Trends Biochem Sci 26(4):230-235 (Apr. 2001).
Nakane and Kawaoi, "Peroxidase-labeled antibody. A new method of conjugation" J Histochem Cytochem 22(12):1084-1091 ( 1974).
Negro et al., "Essential roles of Her2/erbB2 in cardiac development and function" Recent Prog Horm Res 59:1-12 ( 2004).
Newsome and Ernstoff, "The clinical pharmacology of therapeutic monoclonal antibodies in the treatment of malignancy; have the magic bullets arrived?" Brit J Clin Pharmacol 66(1):6-19 ( 2008).
Nguyen et al., "The pharmacokinetics of an albumin-binding Fab (AB.Fab) can be modulated as a function of affinity for albumin" Protein Engineering Design & Selection 19(7):291-297 ( 2006).
Nicolaou et al., "Calicheamicin $\Theta^1{}_1$: A rationally designed molecule with extremely potent and selective DNA cleaving properties and apoptosis inducing activity" Angew Chem Intl Ed Engl 33(2):183-186 ( 1994).
Nikula et al., "A rapid, single vessel method for preparation of clinical grade ligand conjugated monoclonal antibodies" Nucl Med Biol 22:387-390 ( 1995).
Nikula et al., "Alpha-emitting bismuth cyclohexylbenzyl DTPA constructs of recombinant humanized anti-CD33 antibodies: Pharmacokinetics, bioactivity, toxicity and chemistry" J Nucl Med 40(1):166-176 (Jan. 1999).
Nisonoff et al., "Recombination of a mixture of univalent antibody fragments of different specificity" Arch Biochem Biophys 93:460-462 ( 1961).
Offner et al., "T cell receptor peptide therapy triggers autoregulation of experimental encephalomyelitis" Science 251:430-432 ( 1991).
Olafsen et al., "Characterization of engineered anti-p185 $^{HER-2}$ (scFv-C$_{H}$3)$_2$ antibody fragments (minibodies) for tumor targeting" Protein Eng Des Sel 17(4):315-323 ( 2004).
Parenti et al., "Nitric oxide is an upstream signal of vascular endothelial growth factor-induced extracellular signal-regulated kinase $_{1/2}$ activation in postcapillary endothelium." J Biol Chem 273(7):4220-4226 (Feb. 13, 1998).
Park et al., "The erbB2 gene is required for the development of terminally differentiated spinal cord oligodendrocytes" J Cell Biol 154(6):1245-1258 (Sep. 17, 2001).
Patel et al., "Anti-epidermal growth factor recptor monoclonal antibody cetuximab inhibits EGFR/HER-2 heterodimerization and activation" Intl J Oncol 34(1):25-32 ( 2009).
Perik et al., "Serum HER2 levels are increased in patients with chronic heart failure" Eur J Heart Fail 9:173-177 ( 2007).
Pettit et al., "Specific activities of dolastatin 10 and peptide derivatives against cryptococcus neoformans" Antimicrob Agents and Chemotherapy 42(1 1):2961-2965 (Nov. 1998).
Pietras et al., "Antibody to HER-2/neu receptor blocks DNA repair after cisplatin in human breast and ovarian cancer cells" Oncogene 9:1829-1838 ( 1994).
Plowman et al., "Heregulin induces tyrosine phosphorylation of HER4/p180 $^{erbB4}$" Nature 66:473-475 (Dec. 2, 1993).
Plowman et al., "Ligand-specific activation of HER4/p180 $^{erbB4}$, a fourth member of the epidermal growth factor receptor family" P Natl Acad Sci USA 90:1746-1750 (Mar. 1993).
Pluckthun, A. The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 ( 1994).

Pluckthun, A., "Mono- and bivalent antibody fragments produced in *Escherichia coli*: engineering, folding and antigen binding" Immunol Reviews(130):151-188 ( 1992).
Popat and Smith, "Therapy insight: anthracyclines and trastuzumab—the optimal management of cardiotoxic side effects" Nat Clin Pract Oncol 5(6):324-335 (Jun. 2008).
Popkov et al., "Instant immunity through chemically programmable vaccination and covalent self-assembly" Proc Natl Acad Sci USA 106(11):4378-4383 (Mar. 17, 2009).
Presta, L., "Antibody engineering" Curr Opin Struc Biol 2:593-596 ( 1992).
Pullarkat et al., "A phase I study of a HER2/neu bispecific antibody with granulocyte-colony-stimulating factor in patients with metastatic breast cancer that overexpresses HER2/neu" Cancer Immunol Immunother 48:9-21 ( 1999).
Rader et al., "Chemically programmed monoclonal antibodies for cancer therapy: adaptor immunotherapy based on a covalent antibody catalyst" Proc Natl Acad Sci USA 100(9):5396-5400 (Apr. 29, 2003).
Ramm and Pluckthun, "The periplasmic *Escherichia coli* peptidylprolyl cis,trans-isomerase FkpA" J. Biol. Chem. 275(22):17106-17113 (Jun. 2, 2000).
Ranson and Sliwkowski, "Perspectives on anti-HER monoclonal antibodies" Oncology 63( Suppl 1):17-24 ( 2002).
Ravetch and Kinet, "Fc receptors" Ann Rev Immunol 9:457-492 ( 1991).
Razo et al., "Intracellular targeting with low pH-triggered bispecific antibodies" J Biol Chem 272(44):27623-27628 (Oct. 31, 1997).
Remillard and Rebhun, "Antimitotic activity of the potent tumor inhibitor maytansine" Science 189:1002-1005 ( 1975).
Repp et al., "Phase I clinical trial of the bispecific antibody MDX-H210 (anti-FcγR1 x anti-HER-2/neu) in combination with Filgrastim (G-CSF) for treatment of advanced breast cancer" Br J Cancer 89:2234-2243 ( 2003).
Reusch et al., "Anti-CD3 x anti-epidermal growth factor receptor (EGFR) bispecific antibody redirects T-cell cytolytic activity to EGFR-positive cancers in vitro and in an animal model" Clin Cancer Res 12(1):183-190 (Jan. 1, 2006).
Riechmann et al., "Reshaping human antibodies for therapy" Nature 332:323-327 (Mar. 24, 1988).
Rodrigues et al., "Synthesis and β-lactamase-mediated activation of a cephalosporin-taxol prodrug" Chem Biol 2:223-227 (Apr. 1995).
Roselli et al., "In vivo comparison of CHX-DTPA ligand isomers in athymic mice bearing carcinoma xenografts" Cancer Biother Radio 14(3):209-220 ( 1999).
Roux et al., "Comparisons of the ability of human IgG3 hinge mutants, IgM, IgE, and IgA2, to form small immune complexes: a role for flexibility and geometry" J Immunol 161:4083-4090 ( 1998).
Ruegg et al., "Improved in vivo stability and tumor targeting of Bismuth-labeled antibody" Cancer Res 50:4221-4226 (Jul. 15, 1990).
Yes Sarup et al., "Characterization of an anti-P185 $^{HER2}$ monoclonal antibody that stimulates receptor function and Inhibits tumor cell growth" Growth Regulat 1:72-82 ( 1991).
Schaefer et al., "Erlotinib directly inhibits HER2 kinase activation and downstream signaling events in intact cells lacking epidermal growth receptor expression" Cancer Res 67(3):1228-1238 (Feb 1, 2007).
Schaefer et al., "γ-Heregulin: A novel heregulin isoform that is an autocrine growth factor for the human breast cancer cell line, MDA-MB-175" Oncogene 15:1385-1394 ( 1997).
Scheer et al., "Reorienting the Fab domains of trastuzumab results in potent HER2 activators" PLOS ONE 7(12 Suppl e51817):1-13 (Dec. 2012).
Schiffelers et al., "Cancer siRNA therapy by tumor selective delivery with ligand-targeted sterically stabilized nanoparticle" Nucleic Acids Res 32(19):e149 ( 2004).
Schmitz and Ferguson, "Interaction of antibodies with ErbB receptor extracellular regions" Exp Cell Res 315:659-670 ( 2009).
Schrauzer, "Nonenzymatic simulation of nitrogenase reactions and the mechanism of biological nitrogen fixation" Angew Chem Internat Edit 14(8):514-522 ( 1975).

(56) References Cited

OTHER PUBLICATIONS

Scott et al., "p185 $^{HER2}$ signal transduction in breast cancer cells" J Biol Chem 266(22):14300-14305 (Aug. 5, 1991).
Segal and Bast, "Production of bispecific antibodies" Curr Protoc Immunol Chapter 2: Unit 2 13 ( 2001).
Semba et al., "A v-erbB-related protooncogene, c-erbB-2, is distinct from the c-erbB-1/epidermal growth factor-receptor gene and is amplified in a human salivary gland adenocarcinoma" P Natl Acad Sci USA 82:6497-6501 (Oct. 1985).
Senter, P., "Potent antibody drug conjugate's cancer therapy" Curr Opin Chem Biol 13(3):235-244 ( 2009).
Shalaby et al., "Development of humanized bispecific antibodies reactive with cytotoxic lymphocytes and tumor cells overexpressing the HER2 protooncogene" J Exp Med 175:217-225 (Jan. 1992).
Shamis et al., "Bioactivation of self-immolative dendritic prodrugs by catalytic antibody 38C2" J Am Chem Soc 126:1726-1731 ( 2004).
Shan et al., "Anthracycline-induced cardiotoxicity" Ann. Interm. Med 125:47-58 ( 1996).
Shekhar, C., "Double whammy: Bispecific antibodies help immune cells attack tumors" Chem Biol 15:877-878 (Sep. 22, 2008).
Shen et al., "Single variable domain antibody as a versatile building block for the construction of IgG-like bispecific antibodies" J Immunol Methods 318:65-74 ( 2007).
Shen et al., "Single variable domain-IgG fusion. A novel recombinant approach to Fc domain-containing bispecific antibodies" J Biol Chem 281(16):10706-10714 (Apr. 21, 2006).
Shepard et al., "Monoclonal antibody therapy of human cancer: Taking the HER2 protooncogene to the clinic" J Clin Immunol 11(3):117-127 ( 1991).
Sheriff et al., "Redefining the minimal antigen-binding fragment" Nature Struct Biol 3(9):733-736 (Sep. 1996).
Simmons et al., "Expression of full-length immunoglobulins in *Escherichia coli*: Rapid and efficient production of aglycosylated antibodies" J Immunol Methods 263:133-147 ( 2062).
Skerra, A., "Bacterial expression of immunoglobulin fragments" Curr Opin Immunol 5:256-262 ( 1993).
Slamon et al., "Human breast cancer: Correlation of relapse and survival with amplification of the HER-2/neu oncogene" Science 235:177-182 (Jan. 9, 1987).
Slamon et al., "Studies of the HER-2/neu proto-oncogene in human breast and ovarian cancer" Science 244:707-712 (May 12, 1989).
Sliwkowski et al., "Coexpression of erbB2 and erbB3 Proteins Reconstitutes a High Affinity Receptor for Heregulin" J Biol Chem 269(20):14661-14665 (May 20, 1994).
Stella and Himmelstein Directed Drug Delivery "Prodrugs: A chemical approach to targeted drug delivery" Borchardt et al.,Humana Press,:247-267 ( 1985).
Storm et al., "Effect of small changes in orientation on reaction rate" J Am Chem Soc 94:5815-5825 ( 1972).
Sun et al., "Enabling ScFvs as multi-drug carriers: a dendritic approach" Bioorg Med Chem 11:1761-1768 ( 2003).
Sun et al., "Syntheses of dendritic linkers containing chlorambucil residues for the preparation of antibody-multidrug immunoconjugates" Bioorg Med Chem Lett 12:2213-2215 ( 2002).
Suter et al., "Trastuzumab-associated cardiac adverse effects in the herceptin adjuvant trial" J Clin Oncol 25(25):3859-3865 (Sep. 1, 2007).
Swartzman et al., "A homogeneous and multiplexed immunoassay for high-throughput screening using fluorometric microvolume assay technology" Anal Biochem 271:143-151 ( 1999).
Szalai et al., "Geometric disassembly of dendrimers: Dendritic amplification" J Am Chem Soc 125:15688-15689 ( 2003).
Tabrizi et al., "Elimination mechanisms of therapeutic monoclonal antibodies" Drug Discov Today 11:81-88 ( 2006).
Takai et al., "2C4, a monoclonal antibody against HER2, disrupts the HER kinase signaling pathway and inhibits ovarian carcinoma cell growth" Cancer 104:2701-2708 ( 2005).
Toki et al., "Protease-mediated fragmentation of p-amidobenzyl ethers: A new strategy for the activation of anticancer prodrugs" J Org Chem 67:1866-1872 ( 2002).
Tutt et al., "Trispecific F(ab$^1$) $_3$ derivatives that use cooperative signaling via the TCR/CD3 complex and CD2 to activate and redirect resting cytotoxic T cells" J Immunol 147(I):60-69 (Jul. 1991).
Vallette et al., "Construction of mutant and chimeric genes using the polymerase chain reaction" Nucl Acids Res 17(2):723-733 ( 1989).
Valone et al., "Clinical trials of bispecific antibody MDX-210 in women with advanced breast or ovarian cancer that overexpresses HER-2/neu" J Hematotherapy 4:471-475 ( 1995).
Verel et al., "Quantitative $^{89}$Zr immuno-PET for in vivo scouting of $^{90}$Y-labeled monoclonal antibodies in xenograft-bearing nude mice" J Nucl Med 44:1663-1670 ( 2003).
Vermes et al., "A novel assay for apoptosis. Flow cytometric detection of phosphatidylserine expression on early apoptotic cells using fluorescein labeled Annexin V" J Immunol Methods 184:39-51 ( 1995).
Vitetta and Uhr, "Monoclonal antibodies as agonists: An expanded role for their use in cancer therapy" Cancer Res 54(20):5301-5309 (Oct. 15, 1994).
Vornlocher, H, "Antibody-directed cell-type-specific delivery of siRNA" Trends Mol Med 12(1):1-3 (Jan. 2006).
Walker, M., "A high yielding synthesis of N-Alkyl maleimides using a novel modification of the Mitsunobu reaction" J Org Chem 60:5352-5355 ( 1995).
Ward et al., "Binding activities of a repertoire of single immunoglobulin variable domains secreted from *Escherichia coli*" Nature 341:544-546 (Oct. 12, 1989).
Weiner et al., "A human tumor xenograft model of therapy with a bispecific monoclonal antibody targeting c-erbB-2 and CD16" Cancer Res 53:94-100 (Jan. 1, 1993).
Wells and Lowman et al., "Rapid evolution of peptide and protein binding properties in vitro" Curr Opin Biotechnol 3:355-362 ( 1992).
Wells et al., "Cassette mutagenesis: An efficient method for generation of multiple mutations at defined sites" Gene 34:315-323 ( 1985).
Wilman, D. E. V., Prodrugs in cancer chemotherapy biochemical society transactions, 615th ; Meeting, Belfast, Ireland, pp. 375-382 (1986).
Woldeyesus et al., "Peripheral nervous system defects in erbB2 mutants following genetic rescue of heart development" Genes Dev 13(19):2538-2548 ( 1999).
Woyke et al., "In vitro activities and postantifungal effects of the potent dolastatin 10 derivative auristatin PHE" Antimicrob Agents Chemother 45(12):3580-3584 (Dec. 2001).
Wu et al., "Site-specific chemical modification of recombinant proteins produced in mammalian cells by using the genetically encoded aldehyde tag" Proc Natl Acad Sci USA 106:3000-3005 (Mar. 3, 2009).
Xu et al., "Diversity in the CDR3 region of V $_H$ is sufficient for most antibody specificities" Immunity 13:37-45 (Jul. 2000).
Yamamoto et al., "Similarity of protein encoded by the human c-erb-B-2 gene to epidermal growth factor receptor" Nature 319:230-234 (Jan. 16, 1986).
Yarden et al., "Untangling the ErbB signalling network" Nat Rev Mol Cell Biol 2:127-137 (Feb. 2001).
Yu et al., "The biosynthetic gene cluster of the maytansinoid antitumor agent ansamitocin from Actinosynnema pretiosum" P Natl Acad Sci USA 99(12):7968-7973 (Jun. 11, 2002).
Zapata et al., "Engineering linear F(ab') $_2$ fragments for efficient production in *Escherichia coli* and enhanced antiproliferative activity" Protein Eng 8(10):1057-1062 ( 1995).
Zheng et al., "Caspase-3 controls both cytoplasmic and nuclear events associated with Fas-mediated , apoptosis in vivo" p. Natl Acad Sci USA 95:13618-13623 (Nov. 1998).
Zoller and Smith, "Oligonucleotide-directed mutagenesis of DNA fragments cloned into MI3 vectors" Method Enzymol 100:468-500 ( 1983).

(56) References Cited

OTHER PUBLICATIONS

Zoller and Smith., "Oligonucleotide-directed mutagenesis using M 13-derived vectors: An efficient and eneral procedure for the production of point mutations in any fragment of DNA" Nucl Acids Res 10:6487-6500 ( 1983).
Carro et al. (Dec. 2002, e-pub. Nov. 4, 2002). "Serum insulin-like growth factor I regulates brain amyloid-β levels," *Nature Med.* 8(12):1390-1397.
Deyev et al. (Apr. 2009). "Modern Technologies for Creating Synthetic Antibodies for Clinical Application," *Acta Naturae* 1(1):32-50.
Rudikoff et al. (Mar. 1982). "Single amino acid substitution altering antigen-binding specificity," *Proc. Natl. Acad. Sci. USA* 79(6):1979-1983.
Fanger et al. "Bispecific Antibodies for Targeted Cellular Cytotoxicity", *Trends in Biotechnology* 9(1):375-380, (Nov. 1991).
Lyons et al. "Site-Specific Attachment to Recombinant Antibodies Via Introduced Surface Cysteine Residues," *Protein Engineering* 3(8):703-208, (Aug. 1990).
Schott et al. "Preparation, Characterization, and in Vivo Biodistribution Properties of Synthetically Cross-Linked Multivalent Antitumor Antibody Fragments," *Bioconjugate Chemistry* 4(2):153-165, (Mar./Apr. 1993).

Willuda et al. "Tumor Targeting of Mono-, Di-, and Tetravalent Anti-p185$^{HER2}$ Miniantibodies Multimerized by Self-Associating Peptides", *Journal of Biological Chemistry, American Society for Biochemistry and Molecular Biology US* 276(17):14385-14392, (Apr. 27, 2001).
European Search Report and Search Opinion dated Jun. 22, 2016, for European Patent Application No. 10835214.7, filed on Dec. 3, 2010, 34 pages.
International Search Report and Written Opinion dated Jun. 1, 2011 for PCT Application No. PCT/US2010/058958, filed on Dec. 3, 2010, 20 pages
Kipriyanov, S.M. et al. (1994). "Recombinant Single-Chain Fv Fragments Carrying C-Terminal Cysteine Residues: Production of Bivalent and Biotinylated Miniantibodies," *Molecular Immunology* 31(14):1047-1058.
Plückthun, A. et al. (1997). "New Protein Engineering Approaches to Multivalent and Bispecific Antibody Fragments," *Immunotechnology* 3(2):83-105.
Li, J. et al. (Feb. 2006). "Site-Specific Conjugation of Bifunctional Chelator BAT to Mouse IgG1 Fab' Fragment," *Acta Pharmacologica Sincia* 27(2):237-241.
ThermoFisher Scientific. (Apr. 16, 2018). "Thermo Scientific Pierce Protein Biology," http:/www.thermofisher.com/us/en/home/brandsthermo-scientific/pierce-protein-biology.pdf, 2 pages.

\* cited by examiner

| Cys-site Source | LC-110 E. coli | LC-205 thio-mAb | HC-118 thio-mAb | HC-Hg mAb |
| --- | --- | --- | --- | --- |
| | Cys¹¹⁰ | Cys²⁰⁵ | Cys¹¹⁸ | Cys^Hg |

| I.D. | thio-Fab-1 | thio-Fab-2 |
| --- | --- | --- |
| 1321 | HercLC$^{110Cys}$ | HercLC$^{110Cys}$ |
| 1322 | HercLC$^{110Cys}$ | HercLC$^{205Cys}$ |
| 1323 | HercLC$^{110Cys}$ | HercHC$^{118Cys}$ |
| 1324 | HercLC$^{205Cys}$ | HercLC$^{205Cys}$ |
| 1325 | HercLC$^{118Cys}$ | HercLC$^{205Cys}$ |
| 1326 | HercLC$^{118Cys}$ | HercHC$^{118Cys}$ |
| 1327 | HercLC$^{110Cys}$ | HercHC$^{Hg-Cys}$ |
| 1328 | HercLC$^{205Cys}$ | HercHC$^{Hg-Cys}$ |
| 1337 | HercLC$^{118Cys}$ | HercHC$^{Hg-Cys}$ |
| 1329 | HercLC$^{Hg-Cys}$ | HercHC$^{Hg-Cys}$ |
| 1188 | HercLC$^{110Cys}$ | HercLC$^{110Cys}$ |
| 1338 | F(ab')2 | from Herceptin |

*FIG. 3A*

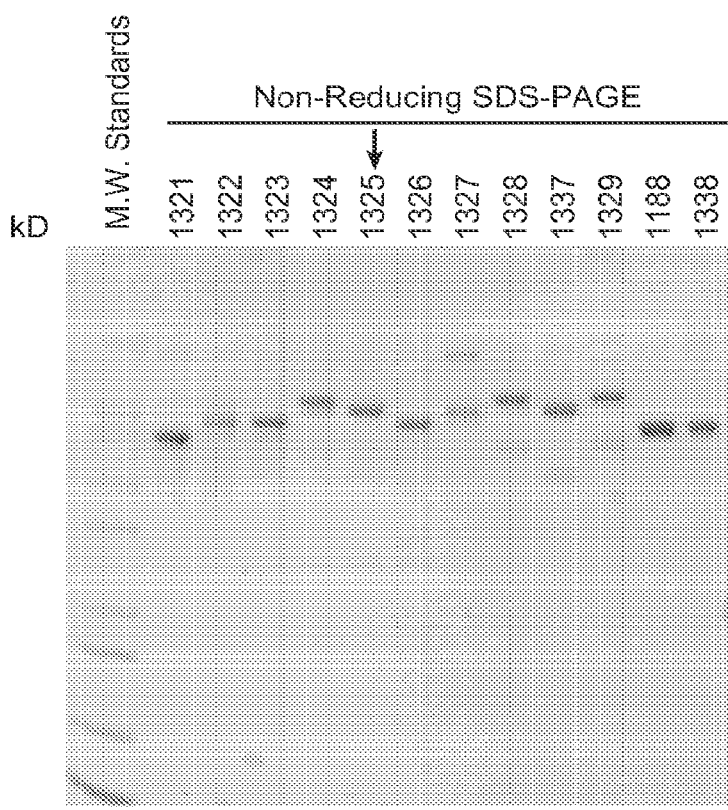

*FIG. 3B*

| Site | Peptide | Peptide Sequence | Quantitation AQUA or label free? | Basal %Phos ± SD | Herceptin %Phos ± SD | Bis-Fab %Phos ± SD | Heregulin %Phos ± SD |
|---|---|---|---|---|---|---|---|
| t701 | 690-713 | LLQETELVEPLtPSGAMPNQAQMR (SEQ ID NO.: 28) | AQUA | 54.8 ± 5.6 | 47.8 ± 4.5 | 66.3 ± 1.5 | 68.5 ± 3.4 |
| s728 | 725-736 | VLGsGAFGTVYK (SEQ ID NO.: 29) | AQUA* | 0.59 ± 0.20 | 0.65 ± 0.08 | 0.59 ± 0.11 | 0.54 ± 0.05 |
| y735 | 725-736 | VLGSGAFGTVyK (SEQ ID NO.: 29) | AQUA | 0.09 ± 0.02 | 0.09 ± 0.01 | 0.10 ± 0.01 | 0.08 ± 0.01 |
| y877 | 869-883 | LLDIDETEyHADGGK (SEQ ID NO.: 30) | AQUA | 4.4 ± 0.9 | 4.2 ± 0.2 | 6.5 ± 0.4 | 3.8 ± 0.8 |
| y1005 | 986-1006 | FVVIQNEDLGPASPLDSTFyR (SEQ ID NO.: 31) | AQUA | 29.6 ± 4.7 | 22.7 ± 5.3 | 44.9 ± 3.0 | 48.3 ± 4.1 |
| s1054 | 1054-1072 | sGGGDLTLGLEPSEEEAPR (SEQ ID NO.: 32) | AQUA | 90.8 ± 1.7 | 88.8 ± 1.5 | 91.4 ± 0.4 | 91.9 ± 0.6 |
| s1054 and s1066 | 1054-1072 | sGGGDLTLGLEPsEEEAPR (SEQ ID NO.: 32) | none | NA | NA | NA | NA |
| s1073 | 1073-1096 | sPLAPSEGAGSDVFDGDLGMGAAK (SEQ ID NO.: 33) | AQUA* | 16.9 ± 2.1 | 8.8 ± 1.7 | 31.6 ± 6.1 | 27.0 ± 5.3 |
| s1078 | 1073-1096 | SPLAPSEGAGsDVFDGDLGMGAAK (SEQ ID NO.: 33) | AQUA | 0.82 ± 0.15 | 1.01 ± 0.42 | 0.84 ± 0.10 | 1.05 ± 0.23 |
| s1083 | 1073-1096 | SPLAPSEGAGSDVFDGDLGMGAAK (SEQ ID NO.: 33) | AQUA* | 5.9 ± 0.64 | 8.6 ± 1.1 | 5.3 ± 0.5 | 5.4 ± 1.0 |
| s1073 and s1078 | 1073-1096 | sPLAPSEGAGsDVFDGDLGMGAAK (SEQ ID NO.: 33) | AQUA* | 3.9 ± 1.1 | 3.6 ± 0.7 | 6.2 ± 1.2 | 5.8 ± 0.9 |
| s1078 and s1083 | 1073-1096 | SPLAPsEGAGsDVFDGDLGMGAAK (SEQ ID NO.: 33) | AQUA | 22.7 ± 2.2 | 30.5 ± 3.5 | 28.0 ± 3.3 | 26.3 ± 2.7 |
| s1073, s1078 and s1083 | 1073-1096 | sPLAPsEGAGsDVFDGDLGMGAAK (SEQ ID NO.: 33) | AQUA* | 9.6 ± 2.8 | 8.5 ± 5.9 | 10.5 ± 2.1 | 13.2 ± 1.9 |
| s1100 | 1097-1111 | GLQsLPTHDPSPLQR (SEQ ID NO.: 34) | AQUA | 0.87 ± 0.08 | 0.92 ± 0.16 | 0.82 ± 0.05 | 0.88 ± 0.06 |
| y1139 | 1112-1153 | YSEDPTVPLPSETDGYVAPLTCSPQPEyVNQPDVRPQPPSPR (SEQ ID NO.: 35) | Label free | 76.8 ± 3.4 | 75.5 ± 3.9 | 82.4 ± 3.9 | 85.5 ± 2.4 |
| s1139 and s1151 | 1112-1153 | YSEDPTVPLPSETDGYVAPLTCSPQPEyVNQPDVRPQPPsPR (SEQ ID NO.: 35) | Label free | 6.8 ± 2.4 | 10.7 ± 2.5 | 12.1 ± 4.4 | 4.9 ± 1.9 |
| t1166 | 1154-1171 | EGPLPAARPAGAtLERPK (SEQ ID NO.: 36) | none | NA | NA | NA | NA |
| t1240/42 | 1239-1255 | GPtAENPEYLGLDVPV(one of these) (SEQ ID NO.: 37) | AQUA* | 40.6 ± 4.6 | 25.5 ± 6.1 | 18.3 ± 2.9 | 30.7 ± 5.5 |
| y1248 | 1239-1255 | GTPTAENPEyLGLDVPV (SEQ ID NO.: 38) | AQUA | 17.8 ± 1.0 | 38.8 ± 2.0 | 32.7 ± 3.0 | 13.8 ± 0.7 |

* = synthetic peptide used has another phos site on same peptide

FIG. 5C

| +13C | +15N | Add Mass | ERBB2 Synthetic Peptide | Heavy Monoisotopic MH+ | |
|---|---|---|---|---|---|
| 5 | 1 | 6.0138 | VLGSGAFGT_V_YK | 1204.6605 | (SEQ ID NO.: 29) |
| 5 | 1 | 6.0138 | VLGSGAFGT_V_yK | 1284.6268 | (SEQ ID NO.: 29) |
| 4 | 2 | 6.0075 | LLDIDETEYHAD_GG_K | 1681.7885 | (SEQ ID NO.: 30) |
| 4 | 2 | 6.0075 | LLDIDETEyHAD_GG_K | 1761.7548 | (SEQ ID NO.: 30) |
| 5 | 1 | 6.0138 | EGPLPAARPAGATLER_P_K | 1837.0323 | (SEQ ID NO.: 36) |
| 5 | 1 | 6.0138 | EGPLPAARPAGA_t_LER_P_K | 1916.9986 | (SEQ ID NO.: 36) |
| 5 | 1 | 6.0138 | SGGGDLTLGLEPSEEEA_P_R | 1919.9225 | (SEQ ID NO.: 32) |
| 5 | 1 | 6.0138 | sGGGDLTLGLEPSEEEA_P_R | 1999.8888 | (SEQ ID NO.: 32) |
| 6 | 1 | 7.0171 | GLQSLPTHDPSP_L_QR | 1652.8827 | (SEQ ID NO.: 34) |
| 6 | 1 | 7.0171 | GLQsLPTHDPSP_L_QR | 1732.8491 | (SEQ ID NO.: 34) |
| 5 | 1 | 6.0138 | GTPTAENPEYLGLDV_P_V | 1777.8887 | (SEQ ID NO.: 37) |
| 5 | 1 | 6.0138 | GTPTAENPEyLGLDV_P_V | 1857.8550 | (SEQ ID NO.: 37) |
| 5 | 1 | 6.0138 | LLQETELVEPLTPSGAM_P_NQAQMR | 2659.3462 | (SEQ ID NO.: 28) |
| 5 | 1 | 6.0138 | LLQETELVEPL_t_PSGAM_P_NQAQMR | 2739.3125 | (SEQ ID NO.: 28) |
| 6 | 1 | 7.0171 | FVVIQNEDLGPASP_L_DSTFYR | 2375.1991 | (SEQ ID NO.: 31) |
| 6 | 1 | 7.0171 | FVVIQNEDLGPASP_L_DSTFyR | 2455.1654 | (SEQ ID NO.: 31) |
| 6 | 1 | 7.0171 | SPLAPSEGAGSDVFDGD_L_GMGAAK | 2256.0562 | (SEQ ID NO.: 33) |
| 6 | 1 | 7.0171 | SPLAPsEGAGSDVFDGD_L_GMGAAK | 2336.0225 | (SEQ ID NO.: 33) |
| 6 | 1 | 7.0171 | SPLAPsEGAGsDVFDGD_L_GMGAAK | 2415.9888 | (SEQ ID NO.: 33) |

*FIG. 5D*

SEQUENCE LISTING

```
<160> NUMBER OF SEQ ID NOS: 38

<210> SEQ ID NO 1
<211> LENGTH: 214
<212> TYPE: PRT
<213> ORGANISM: Unknown
<220> FEATURE:
<223> OTHER INFORMATION: Description of Unknown: HercLC wild-type
      polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

```
Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Cys Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
    210

<210> SEQ ID NO 4
<211> LENGTH: 450
<212> TYPE: PRT
<213> ORGANISM: Unknown
<220> FEATURE:
<223> OTHER INFORMATION: Description of Unknown: HercHC wild-type
      polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 5
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Cys Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 6
<211> LENGTH: 214
<212> TYPE: PRT
<213> ORGANISM: Unknown
<220> FEATURE:
<223> OTHER INFORMATION: Description of Unknown: 2C4LC wild-type
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
```

```
                    100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 7
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Cys Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 8
<211> LENGTH: 227

```
<212> TYPE: PRT
<213> ORGANISM: Unknown
<220> FEATURE:
<223> OTHER INFORMATION: Description of Unknown: 2C4HC (VH-CH1)
      wild-type polypeptide

<400> SEQUENCE: 8
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

```
<210> SEQ ID NO 9
<211> LENGTH: 222
<212> TYPE: PRT
<213> ORGANISM: Unknown
<220> FEATURE:
<223> OTHER INFORMATION: Description of Unknown: 5A6HC (VH-CH1)
      wild-type polypeptide

<400> SEQUENCE: 9
```

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Arg Gly Leu Glu Trp Val
        35                  40                  45

Ala Glu Ile Arg Ser Lys Pro Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

```
Val Tyr Leu Gln Met Thr Ser Leu Arg Pro Glu Asp Thr Gly Ile Tyr
                85                  90                  95

Tyr Cys Thr His Phe Asp Tyr Trp Gly Gln Gly Thr Leu Thr Val
            100                 105                 110

Ser Ser Ala Lys Thr Thr Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr
210                 215                 220

<210> SEQ ID NO 10
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Arg Gly Leu Glu Trp Val
        35                  40                  45

Ala Glu Ile Arg Ser Lys Pro Asn Asn His Ala Thr Tyr Tyr Ala Glu
50                  55                  60

Ser Val Lys Gly Arg Phe Thr Ile Ser Arg Asp Asp Ser Lys Ser Ser
65                  70                  75                  80

Val Tyr Leu Gln Met Thr Ser Leu Arg Pro Glu Asp Thr Gly Ile Tyr
                85                  90                  95

Tyr Cys Thr His Phe Asp Tyr Trp Gly Gln Gly Thr Leu Thr Val
            100                 105                 110

Ser Ser Cys Lys Thr Thr Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Gln Thr Tyr Ile Cys Asn Val Asn His Lys Pro Ser Asn Thr Lys Val
                195                 200                 205

Asp Lys Lys Val Glu Pro Lys Ser Cys Asp Lys Thr His Thr
210                 215                 220
```

<210> SEQ ID NO 11
<211> LENGTH: 214
<212> TYPE: PRT
<213> ORGANISM: Unknown
<220> FEATURE:
<223> OTHER INFORMATION: Description of Unknown: 5A6LC wild-type
     polypeptide

<400> SEQUENCE: 11

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Phe Gln Gln Lys Pro Asp Gly Thr Ile Lys Arg Leu Ile
        35                  40                  45

Tyr Ala Ala Ser Ala Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Leu
                85                  90                  95

Thr Phe Gly Ala Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 12

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Phe Gln Gln Lys Pro Asp Gly Thr Ile Lys Arg Leu Ile
        35                  40                  45

Tyr Ala Ala Ser Ala Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

```
Glu Asp Phe Ala Asp Tyr Tyr Cys Leu Gln Tyr Val Ser Tyr Pro Leu
                85                  90                  95

Thr Phe Gly Ala Gly Thr Lys Val Glu Ile Lys Arg Thr Cys Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 13
<211> LENGTH: 226
<212> TYPE: PRT
<213> ORGANISM: Unknown
<220> FEATURE:
<223> OTHER INFORMATION: Description of Unknown: 22E7HC (VH-CH1)
      wild-type polypeptide

<400> SEQUENCE: 13

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Asn Asn Tyr Thr Phe Tyr Pro Asp Asn Leu
50                  55                  60

Lys Gly Arg Phe Thr Ile Ser Arg Asp Asn Ala Lys Asn Ile Leu Tyr
65                  70                  75                  80

Leu Gln Ile Ser Ser Leu Arg Ser Val Asp Thr Ala Leu Tyr Tyr Cys
                85                  90                  95

Ala Ser Leu Trp Tyr Arg Ala Ser Phe Ala Tyr Trp Gly Gln Gly Thr
            100                 105                 110

Leu Val Thr Val Ser Ser Ala Lys Thr Thr Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
```

His Thr
225

<210> SEQ ID NO 14
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Asn Asn Tyr Thr Phe Tyr Pro Asp Asn Leu
    50                  55                  60

Lys Gly Arg Phe Thr Ile Ser Arg Asp Asn Ala Lys Asn Ile Leu Tyr
65                  70                  75                  80

Leu Gln Ile Ser Ser Leu Arg Ser Val Asp Thr Ala Leu Tyr Tyr Cys
                85                  90                  95

Ala Ser Leu Trp Tyr Arg Ala Ser Phe Ala Tyr Trp Gly Gln Gly Thr
            100                 105                 110

Leu Val Thr Val Ser Ser Cys Lys Thr Thr Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225

<210> SEQ ID NO 15
<211> LENGTH: 214
<212> TYPE: PRT
<213> ORGANISM: Unknown
<220> FEATURE:
<223> OTHER INFORMATION: Description of Unknown: 22E7LC wild-type
      polypeptide

<400> SEQUENCE: 15

Asp Ile Met Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile

```
                35                  40                  45
Ser Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Asp Phe Pro Phe
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Met Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Ser Tyr
                 20                  25                  30

Leu Ser Trp Phe Gln Gln Lys Pro Gly Lys Ser Pro Lys Thr Leu Ile
            35                  40                  45

Ser Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Asp Phe Pro Phe
                 85                  90                  95

Thr Phe Gly Gly Gly Thr Lys Val Glu Ile Lys Arg Thr Cys Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 228
<212> TYPE: PRT
<213> ORGANISM: Unknown
<220> FEATURE:
<223> OTHER INFORMATION: Description of Unknown: D1-5HC (VH-CH1)
      wild-type polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Ile His Trp Val Arg Gln Ala Pro Gly Lys Gly Leu Glu Trp Val
        35                  40                  45

Gly Glu Ile Ser Pro Ser Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Tyr Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His
225

<210> SEQ ID NO 18
<211> LENGTH: 214
<212> TYPE: PRT
<213> ORGANISM: Unknown
<220> FEATURE:
<223> OTHER INFORMATION: Description of Unknown: D1-5LC wild-type
      polypeptide

<400> SEQUENCE: 18

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Thr Pro Tyr
                85                  90                  95

Thr Phe Gly Gln Gly Thr Lys Val Glu Ile Lys Arg Thr Cys Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 229
<212> TYPE: PRT
<213> ORGANISM: Unknown
<220> FEATURE:
<223> OTHER INFORMATION: Description of Unknown: C3-101HC (VH-CH1)
      wild-type polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Gly Thr Ile Asn Pro Tyr Ser Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Ala Val Gly Val Phe Ala Asn Arg Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His
225

<210> SEQ ID NO 21
<211> LENGTH: 214
<212> TYPE: PRT
<213> ORGANISM: Unknown
<220> FEATURE:
<223> OTHER INFORMATION: Description of Unknown: C3-101LC wild-type
      polypeptide

<400> SEQUENCE: 21
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Arg
                85                  90                  95

Thr Phe Gly Gln Gly Thr Lys Val Glu Ile Lys Arg Thr Cys Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Cys Asp Lys Thr His Thr Gly Gly Gly Ser Gln Arg Leu Met Glu Asp
1               5                   10                  15

Ile Cys Leu Pro Arg Trp Gly Cys Leu Trp Glu Asp Asp Phe
            20                  25                  30

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Arg Leu Met Glu Asp Ile Cys Leu Pro Arg Trp Gly Cys Leu Trp
1               5                   10                  15

Glu Asp Asp Phe
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Arg Leu Ile Glu Asp Ile Cys Leu Pro Arg Trp Gly Cys Leu Trp
1               5                   10                  15

Glu Asp Asp Phe
            20

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Arg Leu Ile Glu Asp Ile Cys Leu Pro Arg Trp Gly Cys Leu Trp Glu
1               5                   10                  15
Asp Asp

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Ile Cys Leu Pro Arg Trp Gly Cys Leu Trp
1               5                   10

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Leu Gln Glu Thr Glu Leu Val Glu Pro Leu Thr Pro Ser Gly Ala
1               5                   10                  15

Met Pro Asn Gln Ala Gln Met Arg
            20

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Leu Gly Ser Gly Ala Phe Gly Thr Val Tyr Lys
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Asp Ile Asp Glu Thr Glu Tyr His Ala Asp Gly Gly Lys
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Val Val Ile Gln Asn Glu Asp Leu Gly Pro Ala Ser Pro Leu Asp
1               5                   10                  15

Ser Thr Phe Tyr Arg
```

```
<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Gly Gly Asp Leu Thr Leu Gly Leu Glu Pro Ser Glu Glu Glu
1               5                   10                  15

Ala Pro Arg

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Pro Leu Ala Pro Ser Glu Gly Ala Gly Ser Asp Val Phe Asp Gly
1               5                   10                  15

Asp Leu Gly Met Gly Ala Ala Lys
            20

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Leu Gln Ser Leu Pro Thr His Asp Pro Ser Pro Leu Gln Arg
1               5                   10                  15

<210> SEQ ID NO 35
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Tyr Ser Glu Asp Pro Thr Val Pro Leu Pro Ser Glu Thr Asp Gly Tyr
1               5                   10                  15

Val Ala Pro Leu Thr Cys Ser Pro Gln Pro Glu Tyr Val Asn Gln Pro
            20                  25                  30

Asp Val Arg Pro Gln Pro Pro Ser Pro Arg
        35                  40

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Glu Gly Pro Leu Pro Ala Ala Arg Pro Ala Gly Ala Thr Leu Glu Arg
1               5                   10                  15

Pro Lys

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Thr Pro Thr Ala Glu Asn Pro Glu Tyr Leu Gly Leu Asp Val Pro
1               5                   10                  15

Val

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Thr Pro Thr Ala Glu Asn Pro Glu Tyr Leu Gly Leu Asp Val Pro
1               5                   10                  15

Val
```

METHODS OF MAKING AND USING MULTISPECIFIC ANTIBODY PANELS AND ANTIBODY ANALOG PANELS

CROSS REFERENCE TO RELATED APPLICATIONS

This application is made under 35 U.S.C. § 371 based on International Application PCT/US2010/058958 filed on Dec. 3, 2010, claims the benefit of priority of provisional U.S. Application No. 61/267,006 filed Dec. 4, 2009 and provisional U.S. Application No. 61/346,566 filed May 20, 2010, all of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 30, 2010, is named P4377R1WO.txt and is 53,549 bytes in size.

FIELD

Multispecific antibodies that specifically bind at least two different epitopes are provided. Structural variants of native antibodies (antibody analogs) are also provided. Also provided are multispecific antibodies and antibody analogs having a range of biological activities. Agonist and antagonist multispecific antibodies and agonist and antagonist antibody analogs are provided. Multispecific antibodies and antibody analogs conjugated with therapeutic and/or diagnostic agents are also provided, as are multispecific antibodies and antibody analogs conjugated with agents to increase in vivo half-life compared to multispecific antibodies and antibody analogs lacking such agents. In addition, methods of making multispecific antibodies and antibody analogs and compositions comprising multispecific antibodies and antibody analogs are provided. Therapeutic, research, and diagnostic uses of multispecific antibodies and antibody analogs are also provided.

BACKGROUND

Monoclonal antibodies have provided new therapies for the treatment of various disorders including cancer, immunological and neurological disorders and also infectious diseases. Newsome, B. W. et al., *Br J Clin Pharmacol* 66(1):6-19 (2008); Chames, P., et al., *Br J Pharmacol* 157(2):220-33 (2009); Dimitrov, D. S. et al., *Methods Mol Biol* 525:1-27, xiii (2009). These therapies have been successful, at least in part, because of the robust and strong interaction with target proteins and the singular specificity that monoclonal antibodies provide. The relatively long half-life and stability of monoclonal antibodies in vivo allow for desirable dosing regimens and cell-mediated toxicity can be engaged by the Fc region of the antibody (Tabrizi, M. A., et al., *Drug Discov Today* 11(1-2):81-8 [2006]). In certain instances, therapeutic antibodies have been used to block cellular signals by binding to and neutralizing important functional regions of secreted and cell-surface proteins. Such basic properties of monoclonal antibodies are currently being used to design molecular therapies with different mechanisms of action compared to traditional antibodies (Dimitrov, D. S. et al., *Methods Mol Biol* 525:1-27, xiii [2009]). Certain such technologies are currently in clinical development and show signs of promise (Chames, P., et al., *Br J Pharmacol* 157(2):220-33 [2009]).

For example, one approach involves cell-specific targeting using antibodies to deliver cytotoxic drugs to tumors. Carter, P. J. et al., *Cancer J* 14(3):154-69 (2008); Junutula, J. R., et al., *Nat Biotechnol* 26(8):925-32 (2008); Senter, P. D., *Curr Opin Chem Biol* 13(3):235-44 (2009). In this case, monoclonal antibody specificity directs the cytotoxic molecules to target cells thereby concentrating the high toxicity of the cytotoxic moiety where it is needed while minimizing the impact to nontarget cells. Such antibody-drug conjugates allow for increasing the potency in killing tumor cells while maintaining a window of dosing that minimizes off-target toxicity.

Another example is the delivery of functional complexes such as nanoparticles containing agents such as siRNAs and that include monoclonal antibodies on the surface of the particles for targeting. Schiffelers, R. M., et al., *Nucleic Acids Res* 32(19):e149 (2004); Vornlocher, H. P., *Trends Mol Med* 12(1):1-3 (2006); Davis, M. E., *Mol Pharm* 6(3):659-68 (2009).

Yet another approach uses the bivalent structure of antibodies to construct bispecific molecules that bind to two targets simultaneously (Fischer, N. et al., *Pathobiology* 74(1):3-14 [2007]). Bispecific antibodies offer opportunities for increasing specificity, broadening potency, and utilizing novel mechanisms of action that cannot be achieved with a traditional monoclonal antibody. Drakeman, D. L., *Expert Opin Investig Drugs* 6(9):1169-78 (1997); Kontermann, R. E., *Acta Pharmacol Sin* 26(1):1-9 (2005); Marvin, J. S. et al., *Acta Pharmacol Sin* 26(6):649-58 (2005); Marvin, J. S., et al., *Curr Opin Drug Discov Devel* 9(2):184-93 (2006); Shen, J., et al., *J Biol Chem* 281(16):10706-14 (2006); Chames, P. et al., *Curr Opin Drug Discov Devel* 12(2):276-83 (2009). Cross-linking two different receptors using a bispecific antibody to inhibit a singling pathway has shown utility in a number of applications. In one example, a cell-surface tyrosine phosphatase was recruited into an IgE receptor complex to decrease activity of the phosphorylated IgE receptor (Jackman, et al., *J. Biol. Chem.* 285:20850-20859 (2010)). This approach was more effective than blocking the ligand binding site because inhibition of signaling by the bispecific antibody occurred even in the presence of high concentrations of ligand. Id.

The use of bispecific antibodies to recruit cytotoxic T-cells has also shown clinical opportunities where T-cell activation was achieved in proximity to tumor cells by the bispecific antibody binding receptors simultaneously on the two different cell types. Bargou, R., E., et al., *Science* 321(5891):974-7 (2008); Shekhar, C., *Chem Biol* 15(9): 877-8 (2008); Baeucrle, P. A., et al., *Cancer Res* 69(12): 4941-4 (2009). In one approach, a bispecific antibody having one arm which bound FcγRIII and another which bound to the HER2 receptor was developed for therapy of ovarian and breast tumors that overexpress the HER2 antigen. (Hseih-Ma et al. *Cancer Research* 52:6832-6839 [1992] and Weiner et al. *Cancer Research* 53:94-100 [1993]). Bispecific antibodies can also mediate killing by T cells. Typically, the bispecific antibodies link the CD3 complex on T cells to a tumor-associated antigen. A fully humanized F(ab)$_2$ bispecific antibody consisting of anti-CD3 linked to anti-p185$^{HER2}$ was used to target T cells to kill tumor cells overexpressing the HER2 receptor. Shalaby et al., *J. Exp. Med.* 175(1):217 (1992). Bispecific antibodies have been tested in several early phase clinical trials with encouraging results. In one trial, 12 patients with lung, ovarian or breast cancer were treated with infusions of activated T-lymphocytes targeted with an anti-CD3/anti-tumor (MOC31) bispecific antibody. deLeij et al. *Bispecific Antibodies and Targeted Cellular Cytotoxicity*, Romet-Lemonne, Fanger and Segal Eds., Lienhart (1991) p. 249. The targeted cells induced considerable local lysis of tumor cells, a mild inflammatory reaction, but no toxic side effects or anti-mouse antibody responses.

In addition, bispecific antibodies may be used in the treatment of infectious diseases (e.g. for targeting of effector cells to virally infected cells such as HIV or influenza virus or protozoa such as *Toxoplasma gondii*), used to deliver immunotoxins to tumor cells, or target immune complexes to cell surface receptors. See, e.g., Fanger et al., *Crit. Rev. Immunol.* 12:101-124 (1992). For example, with respect to HIV infection, Berg et al., *PNAS (USA)* 88:4723-4727 (1991) made a bispecific antibody-immunoadhesin chimera which was derived from murine CD4-IgG. These workers constructed a tetrameric molecule having two arms. One arm was composed of CD4 fused with an antibody heavy-chain constant domain along with a CD4 fusion with an antibody light-chain constant domain. The other arm was composed of a complete heavy-chain of an anti-CD3 antibody along with a complete light-chain of the same antibody. By virtue of the CD4-IgG arm, this bispecific molecule binds to CD3 on the surface of cytotoxic T cells. The juxtaposition of the cytotoxic cells and HIV-infected cells results in specific killing of the latter cells.

A number of methods have been described for the synthesis of multispecific antibodies, including bispecific antibodies. Methods for the synthesis of divalent antibody fragments have been described in WO 99/64460. Many of these approaches, however, present a variety of problems. For example, difficulties with protein expression and large scale production, stability and in vivo half-life, folding and aggregation have all been reported. Morimoto, K., et al., *J Immunol Methods* 224(1-2):43-50 (1999); Kriangkum, J., et al., *Biomol Eng* 18(2):31-40 (2001); Segal, D. M. and B. J. Bast (2001). "Production of bispecific antibodies." *Curr Protoc Immunol* Chapter 2:Unit 2 13; Graziano, R. F., et al., *Methods Mol Biol* 283:71-85 (2004); Kontermann, R. E., et al., *Methods Mol Biol* 248:227-42 (2004); Das, D., et al., *Methods Mol Med* 109:329-46 (2005); Fischer, N. et al., *Pathobiology* 74(1):3-14 (2007); Shen, J., et al., *J Immunol Methods* 318(1-2):65-74 (2007). In addition, many of these methods are cumbersome and time-consuming thus limiting the number and variety of molecules that can be constructed and screened for desired activities. The methods described herein address these problems and the methods, compositions, multispecific antibodies and antibody analogs described herein provide additional benefits.

All references cited herein, including patent applications and publications, are incorporated by reference in their entirety for any purpose.

SUMMARY

The methods and compositions of the invention are based, at least in part, on the development of processes for the reliable and reproducible production of high purity multi-specific antibodies and antibody analogs. In certain embodiments, large numbers of multispecific or monospecific combinations can be easily prepared and screened for desired activities. In one aspect, new methods of engineering antibody function are provided based on the surprising and unexpected finding that structural variants of native antibodies can possess a wide spectrum of biological activities ranging from strong antagonist to strong agonist with varying levels of activity in between. In another aspect, using the methods described herein, multispecific antibodies and antibody analogs obtained from pre-existing parent antibodies are provided that possess novel functions not associated with the parent antibodies. The methods and multispecific antibodies and antibody analogs described herein provide, at least in part, novel approaches for the production, screening, identification and development of new therapeutic and diagnostic agents and research tools.

In one aspect, methods of synthesizing a multispecific antibody are provided, wherein a first antibody fragment obtained from a first parent antibody having a first monospecificity and a free sulfhydryl group is reacted with a thio-reactive crosslinker to produce an antibody fragment-crosslinker moiety, and wherein the antibody fragment-crosslinker moiety is reacted with a second antibody fragment obtained from a second parent antibody having a second monospecificity and a free sulfhydryl group to produce the multispecific antibody, and wherein the first monospecificity is different from the second monospecificity. In certain embodiments, the first parent antibody is selected from anti-Her1 and anti-Her2. In certain embodiments, the first parent antibody is anti-Her2 and the second parent antibody is anti-Her1 or the first parent antibody is anti-Her1 and the second parent antibody is anti-Her2. In certain embodiments, the anti-Her2 is selected from Herceptin® (trastuzumab) and 2C4 (pertuzumab). In certain embodiments, the first parent antibody is anti-Her2 and the first antibody fragment comprises a light chain sequence selected from SEQ ID NOs.: 1, 2, 3, 6, and 7 and/or a heavy chain sequence selected from SEQ ID NOs.: 4, 5, and 8. In certain embodiments, the anti-Her1 is selected from D1-5 and C3-101. In certain embodiments, the first parent antibody is anti-Her1 and the first antibody fragment comprises a light chain sequence selected from SEQ ID NOs.: 18, 19, 21, and 22 and/or a heavy chain sequence selected from SEQ ID NOs.: 17 and 20. In certain embodiments, the anti-Her2 is selected from trastuzumab and pertuzumab and the anti-Her1 is selected from D1-5 and C3-101. In certain embodiments, the antibody fragment obtained from anti-Her2 comprises a light chain sequence selected from SEQ ID NOs.: 1, 2, 3, 6, and 7 and/or a heavy chain sequence selected from SEQ ID NOs.: 4, 5, and 8; and the antibody fragment obtained from anti-Her1 comprises a light chain sequence selected from SEQ ID NOs.: 18, 19, 21, and 22 and/or a heavy chain sequence selected from SEQ ID NOs.: 17 and 20.

In a further aspect of the methods described above, the first parent antibody is selected from anti-FcγRIIb and anti-FcεRIα. In certain embodiments, the first parent antibody is anti-FcγRIIb and the second parent antibody is anti-FcεRIα or the first parent antibody is anti-FcεRIα and the second parent antibody is anti-FcγRIIb. In certain embodiments, the anti-FcγRIIb is 5A6. In certain embodiments, the first parent antibody is anti-FcγRIIb and the first antibody fragment comprises a light chain sequence selected from SEQ ID NOs.: 11 and 12 and/or a heavy chain sequence selected from SEQ ID NOs.: 9 and 10. In certain embodiments, the anti-FcεRIα is 22E7. In certain embodiments, the first parent antibody is anti-FcεRIα and the first antibody fragment comprises a light chain sequence selected from SEQ ID NOs.: 15 and 16 and/or a heavy chain sequence selected from SEQ ID NOs.: 13 and 14. In certain embodiments, the antibody fragment obtained from anti-FcγRIIb comprises a light chain sequence selected from SEQ ID NOs.: 11 and 12 and/or a heavy chain sequence selected from SEQ TD NOs.: 9 and 10; and the antibody fragment obtained from anti-FcεRIα comprises a light chain sequence selected from SEQ ID NOs.: 15 and 16 and/or a heavy chain sequence selected from SEQ ID NOs.: 13 and 14.

In yet another aspect, the thio-reactive crosslinker is selected from bis-maleimido halides, bis-alkyl halides, pyridyl disulfides, bis-mercurial salts, 5-thio-2-nitrobenzoic acid-mediated crosslinking, and bis-thiosulfonates. In one embodiment, the crosslinker is bis-maleimide. In certain embodiments, the first antibody fragment and/or the second antibody fragment are obtained from a cysteine-engineered antibody. In certain such embodiments, the first antibody fragment and/or the second antibody fragments is a thio-Fab. In certain embodiments, the cysteine-engineered antibody comprises a cysteine substitution at position 110 or at position 205 of the light chain, wherein the numbering of the residues is according to the EU numbering system. In certain embodiments, the cysteine-engineered antibody comprises a cysteine substitution at position 118 or at position 121 of the heavy chain, wherein the numbering of the residues is according to the EU numbering system. In certain embodiments, the first antibody fragment and/or the second antibody fragment is obtained from a native antibody, wherein the native antibody is digested with pepsin to produce an F(ab')$_2$ fragment, wherein the F(ab')$_2$ fragment is purified and treated with a reducing agent followed by an oxidizing agent under conditions wherein the disulfide between the heavy chain and the light chain of Fab is reformed and cysteine residues in the hinge region remain unoxidized.

In another aspect, methods of synthesizing an antibody analog are provided, wherein a first antibody fragment having a free sulfhydryl group is reacted with a thio-reactive crosslinker to produce an antibody fragment-crosslinker moiety, and wherein the antibody fragment-crosslinker moiety is reacted with a second antibody fragment having a free sulfhydryl group to produce the antibody analog, and wherein the first antibody fragment and the second antibody fragment are obtained from a single parent antibody. In certain embodiments, the antibody analog has an antigen binding region that differs structurally from the antigen binding region of the parent antibody. In certain embodiments, the parent antibody is selected from anti-Her1, anti-Her2, anti-FcεRIα, and anti-FcγRIIb. In certain embodiments, the anti-Her2 is selected from Herceptin® (trastuzumab) and 2C4 (pertuzumab). In certain embodiments, the parent antibody is anti-Her2 and the first antibody fragment and the second antibody fragment comprise the same light chain sequence, wherein the light chain sequence is selected from SEQ ID NOs.: 1, 2, 3, 6, and 7 and/or the same heavy chain sequence, wherein the heavy chain sequence is selected from SEQ ID NOs.: 4, 5, and 8. In certain embodiments, the anti-Her1 is selected from D1-5 and C3-101. In certain embodiments, the parent antibody is anti-Her1 and the first antibody fragment and the second antibody fragment comprise the same light chain sequence, wherein the light chain sequence is selected from SEQ ID NOs.: 18, 19, 21, and 22 and/or the same heavy chain sequence, wherein the heavy chain sequence is selected from SEQ ID NOs.: 17 and 20. In certain embodiments, the anti-FcγRIIb is 5A6. In certain embodiments, the parent antibody is anti-FcγRIIb and the first antibody fragment and the second antibody fragment comprise the same light chain sequence, wherein the light chain sequence is selected from SEQ ID NOs.: 11 and 12 and/or the same heavy chain sequence, wherein the heavy chain sequence is selected from SEQ ID NO.: 9 and 10. In certain embodiments, the anti-FcεRIα is 22E7. In certain embodiments, the parent antibody is anti-FcεRIα and the first antibody fragment and the second antibody fragment comprise the same light chain sequence, wherein the light chain sequence is selected from SEQ ID NOs.: 15 and 16 and/or the same heavy chain sequence, wherein the heavy chain sequence is selected from SEQ ID NO.: 13 and 14. In certain embodiments, the parent antibody is a cysteine-engineered antibody. In certain embodiments, the parent antibody is a native antibody.

In a further aspect, methods of synthesizing a multispecific antibody or antibody analog are provided as above, wherein the crosslinker is a modified crosslinker comprising a protected SH group. In one embodiment, the modified crosslinker is bis-maleimido-acetylacetate (BMata). In certain embodiments, the multispecific antibody or antibody analog comprising the modified crosslinker is further reacted with an agent comprising a functional group. In certain embodiments, the agent is selected from polyethylene glycol (PEG), albumin-binding peptide (ABP), a fluorescent tag, a radioimaging agent, a cytotoxic agent, and siRNA. In certain embodiments, the multispecific antibody or antibody analog comprising the modified crosslinker is further reacted with PEG. In certain embodiments, the PEG is 2000 mw (2K) PEG, 12,000 mw (12K) PEG, or 20,000 mw (20K) PEG.

In yet another aspect, methods of synthesizing a panel of multispecific antibodies are provided, wherein a first antibody fragment obtained from a first parent antibody having a first monospecificity and a free sulfhydryl group is reacted with a thio-reactive crosslinker to produce an antibody fragment-crosslinker moiety, and wherein the antibody fragment-crosslinker moiety is reacted pairwise with each of two or more additional antibody fragments obtained from one or more parent antibodies of different monospecificity from the first parent antibody, each having a free sulfhydryl group, to produce a panel of multispecific antibodies. In certain embodiments, the antibody fragment-crosslinker moiety is reacted pairwise with each of three or more additional antibody fragments, or each of four or more additional antibody fragments, or each of five or more additional antibody fragments, or each of ten or more additional antibody fragments, or each of 15 or more additional antibody fragments, or each of 20 or more additional antibody fragments, or each of 25 or more additional antibody fragments, or each of 50 or more additional antibody fragments, or each of 100 or more additional antibody fragments, in each case obtained from one or more parent antibodies, or two or more parent antibodies, or three or more parent antibodies, or four or more parent antibodies, or five or more parent antibodies, or ten or more parent antibodies, or or more parent antibodies, or 20 or more parent antibodies, or 25 or more parent antibodies, or 50 or more parent antibodies, or 100 or more parent antibodies, in each case of different monospecificity from the first parent antibody. In certain embodiments, the first parent antibody is selected from anti-Her1, anti-Her2, anti-FcεRIα and anti-FcγRIIb. In certain embodiments, the first antibody fragment is obtained from anti-Her2 and each of the two or more additional antibody fragments is obtained from anti-Her1, or the first antibody fragment is obtained from anti-Her1 and each of the two more additional antibody fragments is obtained from anti-Her2, or the first antibody fragment is obtained from anti-FcεRIα and each of the two or more additional antibody fragments is obtained from anti-FcγRIIb, or the first antibody fragment is obtained from anti-FcγRIIb and each of the two or more additional antibody fragments is obtained from anti-FcεRIα. In certain embodiments, the anti-Her2 is selected from Herceptin® (trastuzumab) and 2C4 (pertuzumab). In certain embodiments, the anti-Her1 is selected from D1-5 and C3-101. In certain embodiments, the anti-Her2 is selected from trastuzumab and pertuzumab and the anti-Her1 is selected from D1-5 and C3-101. In certain embodiments, the anti-FcγRIIb is 5A6. In certain embodiments, the anti-FcεRIα is 22E7. In certain embodiments, the anti-FcγRIIb is 5A6 and the anti-FcεRIα is 22E7. In certain embodiments, the thio-reactive crosslinker is selected from bis-maleimido halides, bis-alkyl halides, pyridyl disulfides, bis-mercurial salts, 5-thio-2-nitrobenzoic acid-mediated crosslinking, and bis-thiosulfonates. In one embodiment, the thio-reactive crosslinker is bis-maleimide. In certain embodiments, the first antibody fragment and/or each of the two or more additional antibody fragments are obtained from a cysteine-engineered antibody. In certain such embodiments, the cysteine-engineered antibody comprises a substitution at position 110 or at position 205 of the light chain, wherein the numbering of the residues is according to the EU numbering system, and wherein the substitution is cysteine. In certain embodiments, the cysteine-engineered antibody comprises a substitution at position 118 or at position 121 of the heavy chain, wherein the numbering of the residues is according to the EU numbering system, and wherein the substitution is cysteine.

In still yet another aspect, methods of synthesizing a panel of antibody analogs are provided, wherein a first antibody fragment having a free sulthydryl group is reacted with a thio-reactive crosslinker to produce an antibody fragment-crosslinker moiety, and wherein the antibody fragment-crosslinker moiety is reacted pairwise with each of two or more additional antibody fragments, each having a free sulfhydryl group, to produce the panel of antibody analogs, wherein each of the antibody fragments are obtained from a single parent antibody. In certain embodiments, the antibody fragment-crosslinker moiety is reacted pairwise with each of three or more additional antibody fragments, or each of four or more additional antibody fragments, or each of five or more additional antibody fragments, or each of ten or more additional antibody fragments, or each of 15 or more additional antibody fragments, or each of 20 or more additional antibody fragments, or each of 25 or more additional antibody fragments, or each of 50 or more additional antibody fragments, wherein each of the antibody fragments are obtained from a single parent antibody. In certain embodiments, one or more of the antibody analogs of the panel has an antigen binding region that differs structurally from the antigen binding region of the parent antibody. In certain embodiments, the parent antibody is selected from anti-Her1, anti-Her2, anti-FcεRIα and anti-FcγRIIb. In certain embodiments, the anti-Her2 is selected from trastuzumab and pertuzumab. In certain embodiments, the anti-Her1 is selected from D1-5 and C3-101. In certain embodiments, the anti-FcγRIIb is 5A6. In certain embodiments, the anti-FcεRIα, is 22E7. In certain embodiments, the thio-reactive crosslinker is selected from bis-maleimido halides, bis-alkyl halides, pyridyl disulfides, bis-mercurial salts, 5-thio-2-nitrobenzoic acid-mediated crosslinking, and bis-thiosulfonates. In one embodiment, the thio-reactive crosslinker is bis-maleimide. In certain embodiments, the parent antibody is a cysteine-engineered antibody. In certain such embodiments, the cysteine-engineered antibody comprises a substitution at position 110 or at position 205 of the light chain, wherein the numbering of the residues is according to the EU numbering system, and wherein the substitution is cysteine. In certain embodiments, the cysteine-engineered antibody comprises a substitution at position 118 or at position 121 of the heavy chain, wherein the numbering of the residues is according to the EU numbering system, and wherein the substitution is cysteine.

In a further aspect, a multispecific antibody is provided, synthesized by a process comprising reacting a first antibody fragment obtained from a first parent antibody having a first monospecificity and a free sulfhydryl group with a thio-reactive crosslinker to produce an antibody fragment-crosslinker moiety, and then reacting the antibody fragment-crosslinker moiety with a second antibody fragment obtained from a second parent antibody having a second monospecificity and a free sulfhydryl group to produce the multispecific antibody, and wherein the first monospecificity is different from the second monospecificity. In certain embodiments, the first parent antibody is selected from anti-Her1 and anti-Her2. In certain embodiments, the first parent antibody is anti-Her2 and the second parent antibody is anti-Her1 or the first parent antibody is anti-Her1 and the second parent antibody is anti-Her2. In certain embodiments, the anti-Her2 is selected from Herceptin® (trastuzumab) and 2C4 (pertuzumab). In certain embodiments, the first parent antibody is anti-Her2 and the first antibody fragment comprises a light chain sequence selected from SEQ ID NOs.: 1, 2, 3, 6, and 7 and/or a heavy chain sequence selected from SEQ ID NOs.: 4, 5, and 8. In certain embodiments, the anti-Her1 is selected from D1-5 and C3-101. In certain embodiments, the first parent antibody is anti-Her1 and the first antibody fragment comprises a light chain sequence selected from SEQ ID NOs.: 18, 19, 21, and 22 and/or a heavy chain sequence selected from SEQ ID NOs.: 17 and 20. In certain embodiments, the anti-Her2 is selected from trastuzumab and pertuzumab and the anti-Her1 is selected from D1-5 and C3-101. In certain embodiments, the antibody fragment obtained from anti-Her2 comprises a light chain sequence selected from SEQ ID NOs.: 1, 2, 3, 6, and 7 and/or a heavy chain sequence selected from SEQ ID NOs.: 4, 5, and 8; and the antibody fragment obtained from anti-Her1 comprises a light chain sequence selected from SEQ ID NOs.: 18, 19, 21, and 22 and/or a heavy chain sequence selected from SEQ ID NOs.: 17 and 20.

In a further aspect of the multispecific antibodies described above, the first parent antibody is selected from anti-FcγRIIb and anti-FcεRIα. In certain embodiments, the first parent antibody is anti-FcγRIIb and the second parent antibody is anti-FcεRIα or the first parent antibody is anti-FcεRIα and the second parent antibody is anti-FcγRIIb. In certain embodiments, the anti-FcγRIIb is 5A6. In certain embodiments, the first parent antibody is anti-FcγRIIb and the first antibody fragment comprises a light chain sequence selected from SEQ ID NOs.: 11 and 12 and/or a heavy chain sequence selected from SEQ ID NOs.: 9 and 10. In certain embodiments, the anti-FcεRIα is 22E7. In certain embodiments, the first parent antibody is anti-FcεRIα and the first antibody fragment comprises a light chain sequence selected from SEQ ID NOs.: 15 and 16 and/or a heavy chain sequence selected from SEQ ID NOs.: 13 and 14. In certain embodiments, the antibody fragment obtained from anti-FcγRIIb comprises a light chain sequence selected from SEQ ID NOs.: 11 and 12 and/or a heavy chain sequence selected from SEQ TD NOs.: 9 and 10; and the antibody fragment obtained from anti-FcεRIα comprises a light chain sequence selected from SEQ ID NOs.: 15 and 16 and/or a heavy chain sequence selected from SEQ ID NOs.: 13 and 14.

In yet a further aspect, a multispecific antibody is provided, synthesized by a process as described above, wherein the first parent antibody specifically binds a target on a T cell and the second parent antibody specifically binds a target on a tumor cell. In certain embodiments, the first parent antibody is anti-CD3 and the second parent antibody is selected from anti-BLR1, anti-BR3, anti-CD19, anti-CD20, anti-CD22, anti-CD72, anti-CD79A, anti-CD79B, anti-CD180, anti-CR2, anti-FCER2, anti-FcRH1, anti-FcRH2, anti-FcRH5, anti-FCRL4, anti-Her2, anti-HLA-DOB, and anti-NAG14. In one embodiment, the first parent antibody is anti-CD3 and the second parent antibody is anti-CD19. In one embodiment, the first parent antibody is anti-CD3 and the second parent antibody is anti-CD20. In one embodiment, the first parent antibody is anti-CD3 and the second parent antibody is anti-CD22. In one embodiment, the first parent antibody is anti-CD3 and the second parent antibody is anti-FcRH5. In one embodiment, the first parent antibody is anti-CD3 and the second parent antibody is anti-Hcr2. In certain embodiments, the multispecific antibody demonstrates polyepitopic specificity. In certain embodiments, the multispecific antibody demonstrates one or more biological activities indistinguishable from each of the parent antibodies. In certain embodiments, the multispecific antibody demonstrates one or more biological activities distinguishable from at least one of the parent antibodies.

In another aspect, an antibody analog is provided, synthesized by a process comprising reacting a first antibody fragment having a free sulfhydryl group with a thio-reactive crosslinker to produce an antibody fragment-crosslinker moiety, and then reacting the antibody fragment-crosslinker moiety with a second antibody fragment having a free sulfhydryl group to produce the antibody analog, and wherein the first antibody fragment and the second antibody fragment are obtained from a single parent antibody. In certain embodiments, the parent antibody is selected from anti-Her1, anti-Her2, anti-FcεRIα, and anti-FcγRIIb. In certain embodiments, the anti-Her2 is selected from Herceptin® (trastuzumab) and 2C4 (pertuzumab). In certain embodiments, the parent antibody is anti-Her2 and the first antibody fragment and the second antibody fragment comprise the same light chain sequence, wherein the light chain sequence is selected from SEQ ID NOs.: 1, 2, 3, 6, and 7 and/or the same heavy chain sequence, wherein the heavy chain sequence is selected from SEQ ID NOs.: 4, 5, and 8. In certain embodiments, the anti-Her1 is selected from D1-5 and C3-101. In certain embodiments, the parent antibody is anti-Her1 and the first antibody fragment and the second antibody fragment comprise the same light chain sequence, wherein the light chain sequence is selected from SEQ ID NOs.: 18, 19, 21, and 22 and/or the same heavy chain sequence, wherein the heavy chain sequence is selected from SEQ ID NOs.: 17 and 20. In certain embodiments, the anti-FcγRIIb is 5A6. In certain embodiments, the parent antibody is anti-FcγRIIb and the first antibody fragment and the second antibody fragment comprise the same light chain sequence, wherein the light chain sequence is selected from SEQ ID NOs.: 11 and 12 and/or the same heavy chain sequence, wherein the heavy chain sequence is selected from SEQ ID NO.: 9 and 10. In certain embodiments, the anti-FcεRIα is 22E7. In certain embodiments, the parent antibody is anti-FcεRIα and the first antibody fragment and the second antibody fragment comprise the same light chain sequence, wherein the light chain sequence is selected from SEQ ID NOs.: 15 and 16 and/or the same heavy chain sequence, wherein the heavy chain sequence is selected from SEQ ID NO.: 13 and 14. In certain embodiments, the parent antibody is a cysteine-engineered antibody. In certain embodiments, the parent antibody is a native antibody. In certain embodiments, the antibody analog demonstrates one or more biological activities indistinguishable from the parent antibody. In certain embodiments, the antibody analog demonstrates one or more biological activities distinguishable from the parent antibody. In certain embodiments, the biological activity is cell proliferation. In certain embodiments, the antibody analog is an antagonist of Her2-expressing cells and the parent antibody is Herceptin® (trastuzumab). In certain such embodiments, the antibody analog is selected from bis-Fab 1324, bis-Fab 1328, and bis-Fab 1329. In certain embodiments, the biological activity of the antibody analog is antagonistic and the biological activity of the parent antibody is agonistic. In certain embodiments, the biological activity of the antibody analog is agonistic and the biological activity of the parent antibody is antagonistic. In certain embodiments, the antibody analog is an agonist of Her2-expressing cells and the parent antibody is Herceptin® (trastuzumab). In certain such embodiments, the antibody analog is selected from bis-Fab 1188, bis-Fab 1321, bis-Fab 1322, bis-Fab 1323, and bis-Fab 1325.

In another aspect, compositions comprising one or more multispecific antibodies are provided. In certain embodiments, the one or more multispecific antibodies are selected from bis-Fab 1187, bis-Fab 1189, bis-Fab 1190, bis-Fab 1191, bis-Fab 1192, bis-Fab 1193, bis-Fab 1299, bis-Fab 1300, bis-Fab 1301, bis-Fab 1302, bis-Fab1303, bis-Fab 1304, bis-Fab 1305, bis-Fab 1306, and bis-Fab 1307.

In yet another aspect, compositions comprising one or more antibody analogs are provided. In certain embodiments, the one or more antibody analogs are selected from bis-Fab 1188, bis-Fab 1204, bis-Fab 1321, bis-Fab 1322, bis-Fab 1323, bis-Fab 1324, bis-Fab 1325, bis-Fab 1326, bis-Fab 1327, bis-Fab 1328, bis-Fab 1329, bis-Fab 1400, and bis-Fab 1401.

In yet still another aspect, methods of treating cancer are provided, wherein a therapeutically effective amount of a multispecific antibody as described above is administered to a subject in need of treatment. In certain embodiments, the first antibody fragment is anti-Her2 and the second antibody fragment is anti-Her1. In certain embodiments, the anti-Her2 is selected from Herceptin® (trastuzumab) and 2C4 (pertuzumab). In certain embodiments, the anti-Her1 is selected from D1-5 and C3-101. In certain embodiments, the first antibody fragment is anti-CD3 and the second antibody fragment is selected from anti-BLR1, anti-BR3, anti-CD19, anti-CD20, anti-CD22, anti-CD72, anti-CD79A, anti-CD79B, anti-CD180, anti-CR2, anti-FCER2, anti-FcRH1, anti-FcRH2, anti-FcRH5, anti-FCRL4, anti-Her2, anti-HLA-DOB, and anti-NAG14. In one embodiment, the first antibody fragment is anti-CD3 and the second antibody fragment is anti-CD19. In one embodiment, the first antibody fragment is anti-CD3 and the second antibody fragment is anti-CD20. In one embodiment, the first antibody fragment is anti-CD3 and the second antibody fragment is anti-CD22. In one embodiment, the first antibody fragment is anti-CD3 and the second antibody fragment is anti-FcRH5. In one embodiment, the first antibody fragment is anti-CD3 and the second antibody fragment is anti-Her2.

In another aspect, methods for killing or inhibiting the proliferation of tumor cells or cancer cells are provided comprising treating the cells with an amount of a multispecific antibody as described above, or a pharmaceutically acceptable salt or solvate thereof, the amount being effective to kill or inhibit the proliferation of the tumor cells or cancer cells.

Yet further aspects are provided which include methods for treating: an autoimmune disease; or an infectious disease

DETAILED DESCRIPTION OF CERTAIN EMBODIMENTS

Figure 1:
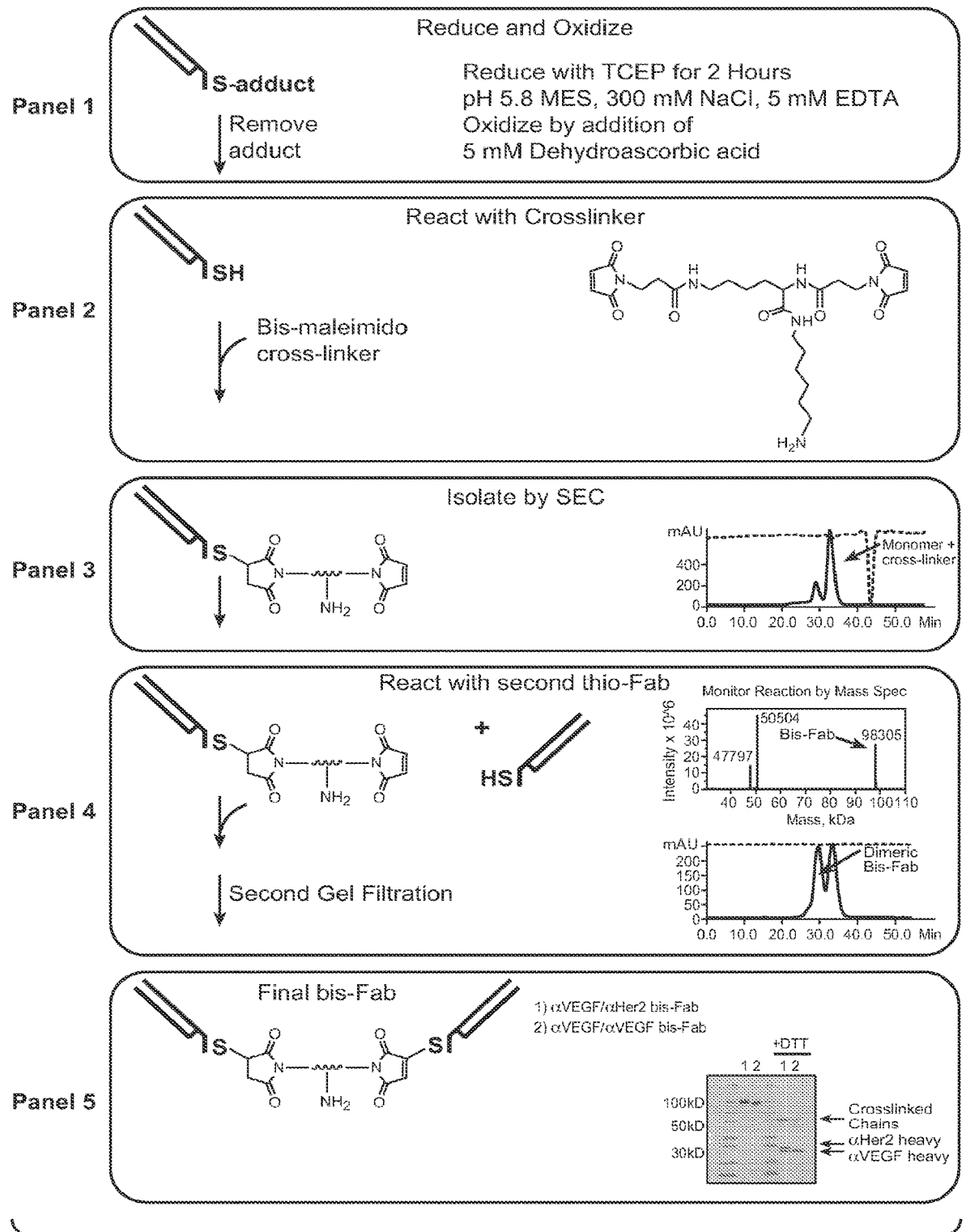
FIG. 1 shows the process for synthesis of bis-Fabs as described in Example 1. Panel 1, removal of thio-adducts by reduction and oxidation; Panel 2, reaction of the first thio-Fab or hinge-cys-Fab with bis-maleimido crosslinker; Panel 3, isolation of the monomeric species containing crosslinker by size exclusion chromatography (SEC), panel inset; Panel 4, reaction of the monomeric crosslinked species with the second thio-Fab or hingc-cys-Fab, upper panel inset showing mass spectrometry results and isolation of the 100 kD bis-Fab product, lower panel inset showing isolation of the dimeric bis-Fab by SEC; Panel 5, schematic drawing of the final bis-Fab product, SDS-PAGE analysis of two different bis-Fabs, αVEGF/αHer2 (1) and αVEGF/αVEGF (2) under nonreducing and reducing (+DTT) conditions.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994); March, Advanced Organic Chemistry Reactions, Mechanisms and Structure 4th ed., John Wiley & Sons (New York, N.Y. 1992); and Janeway, C., Travers, P., Walport, M., Shlomchik (2001) Immunobiology, 5th Ed., Garland Publishing, New York provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

When trade names are used herein, applicants intend to independently include the trade name product formulation, the generic drug, and the active pharmaceutical ingredient(s) of the trade name product.

The term "antibody" is used herein in the broadest sense and refers to any immunoglobulin (Ig) molecule comprising two heavy chains and two light chains, and any fragment, mutant, variant or derivation thereof which so long as they exhibit the desired biological activity (e.g., epitope binding activity). See, e.g., Miller et al. *Jour. of Immunology* 170: 4854-4861 (2003). Examples of antibodies include, but are not limited to, monoclonal antibodies, polyclonal antibodies, multispecific antibodies, antibody analogs, and antibody fragments. Antibodies may be murine, human, humanized, chimeric, or derived from other species.

Antibody residues herein are numbered according to the Kabat numbering system and the EU number system. The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system.

The term "multispecific antibody" is used herein in the broadest sense and specifically covers an antibody that has polyepitopic specificity. Multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains where each $V_H V_L$ unit binds to a different epitope, antibodies having two or more single variable domains with each single variable domain binding to a different epitope, full length antibodies, and antibodies comprising one or more antibody fragments as well as antibodies comprising antibody fragments that have been linked covalently or non-covalently. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

The term "polyepitopic specificity" refers to the ability of a multispecific antibody to specifically bind to two or more different epitopes on the same target or on different targets.

The terms "monospecific" and "monospecificity" refer to the ability of an antibody to bind only one epitope and specifically cover a molecule that specifically binds a target molecule.

The term "antibody analog" is used herein in the broadest sense and specifically covers a molecule that specifically binds a target molecule with monospecificity and that is structurally different from a native antibody. Antibody analogs may comprise one or more antibody fragments from a native antibody. Antibody analogs include, but are not limited to, an antibody analog comprising a heavy chain variable domain ($V_H$) and a light chain variable domain ($V_L$), where the $V_H V_L$ unit is monospecific, antibody analogs having two or more $V_L$ and $V_H$ domains where each $V_H V_L$ unit is monospecific for the same epitope, antibody analogs having two or more single variable domains with each single variable domain binding to the same epitope, antibody analogs comprising one or more antibody fragments, antibody analogs comprising antibody fragments that have been linked covalently or non-covalently, and antibody analogs where the $V_H V_L$ units, single variable domains, and/or antibody fragments are in a configuration different from that of native antibodies.

"Antibody fragments" comprise a portion of an intact antibody, typically the antigen binding region or a variable region of the intact antibody. Examples of antibody fragments include, but are not limited to, Fab, Fab', F(ab')₂, Fv, diabodies (Db); tandem diabodies (taDb), linear antibodies (see U.S. Pat. No. 5,641,870, Example 2; Zapata et al., Protein Eng. 8(10):1057-1062 (1995)); one-armed antibodies, single variable domain antibodies, minibodies (Olafsen et al (2004) Protein Eng. Design & Sel. 17(4):315-323), single-chain antibody molecules, fragments produced by a Fab expression library, anti-idiotypic (anti-Id) antibodies, CDR (complementary determining region), and epitope-binding fragments.

The term "Fab" refers to an antibody fragment that consists of an entire L chain ($V_L$ and $C_L$) along with the variable region domain of the H chain ($V_H$), and the first constant domain of one heavy chain ($C_H1$). Papain digestion of an intact antibody can be used to produce two Fab fragments, each of which contains a single antigen-binding site. Typically, the L chain and H chain fragment of the Fab produced by papain digestion are linked by an interchain disulfide bond.

The term "Fc" refers to an antibody fragment that comprises the carboxy-terminal portions of both H chains ($C_H2$ and $C_H3$) and a portion of the hinge region held together by disulfide bonds. The effector functions of antibodies are determined by sequences in the Fc region; this region is also the part recognized by Fc receptors (FcR) found on certain types of cells. One Fc fragment can be obtained by papain digestion of an intact antibody.

The term "F(ab')$_2$" refers to an antibody fragment produced by pepsin digestion of an intact antibody. F(ab')$_2$ fragments contain two Fab fragments and a portion of the hinge region held together by disulfide bonds. F(ab')$_2$ fragments have divalent antigen-binding activity and are capable of cross-linking antigen.

The term Fab' refers to an antibody fragment that is the product of reduction of an F(ab')$_2$ fragment. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group.

The term "hinge region" refers to the portion of an antibody stretching from Glu216 to Pro230 of human IgG1 (Burton, Molec. Immunol. 22:161-206 (1985)). Hinge regions of other IgG isotypes may be aligned with the IgG1 sequence by placing the first and last cysteine residues forming inter-heavy chain S—S bonds in the same positions.

The term "Fv" refers to an antibody fragment that consists of a dimer of one heavy-chain variable region and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

The term "Single-chain Fv" also abbreviated as "sFv" or "scFv" refer to antibody fragments that comprise the $V_H$ and $V_L$ antibody domains connected into a single polypeptide chain. Typically, the scFv polypeptide further comprises a polypeptide linker between the $V_H$ and $V_L$ domains, which enables the scFv to form the desired structure for antigen binding. For a review of scFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing scFv fragments with short linkers (typically about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Exemplary diabodies are described in, for example, EP 404,097; WO 93/11161; and Hollinger et al., Proc. Natl. Acad. Sci. USA 90:6444-6448 (1993).

The term "one-armed antibody" refers to an antibody that comprises (1) a variable domain joined by a peptide bond to a polypeptide comprising a CH2 domain, a CH3 domain or a CH2-CH3 domain and (2) a second CH2, CH3 or CH2-CH3 domain lacking a variable domain. One-armed antibodies may comprise 3 polypeptides (1) a first polypeptide comprising a variable domain (e.g., VH), CH1, CH2 and CH3, (2) a second polypeptide comprising a variable domain (e.g., VL) and a CL domain, and (3) a third polypeptide comprising a CH2 and CH3 domain. One-aimed antibodies may have a partial hinge region containing the two cysteine residues which form disulphide bonds linking the constant heavy chains. Typically, the variable domains of the one armed antibody form an antigen binding region. In certain instances, the variable domains of the one armed antibody are single variable domains, wherein each single variable domain is an antigen binding region.

The term "single domain antibodies" (sdAbs) or "single variable domain (SVD) antibodies" refers to antibodies in which a single variable domain (VH or VL) confers antigen binding. In other words, the single variable domain does not need to interact with another variable domain to recognize and bind the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dcv Comp Immunol (2006) 30:43-56; Trend Biochem Sci (2001) 26:230-235; Trends Biotechnol (2003):21:484-490; WO 2005/035572; WO 03/035694; Febs Lett (1994) 339:285-290; WO00/29004; WO 02/051870).

The term "linear antibodies" refers to the antibodies described in Zapata et al., Protein Eng. 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

The term "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see for example: U.S. Pat. Nos. 4,816,567; 5,807, 715). The monoclonal antibodies may also be isolated from phage antibody libraries using the techniques described in Clackson et al (1991) Nature, 352:624-628; Marks et al (1991) J. Mol. Biol., 222:581-597; for example.

An "intact antibody" refers to an antibody comprising VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; and down regulation of cell surface receptors such as B cell receptor.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310).

An "ErbB receptor" is a receptor protein tyrosine kinase which belongs to the ErbB receptor family whose members are important mediators of cell growth, differentiation and survival. The ErbB receptor family includes four distinct members including epidermal growth factor receptor (EGFR, ErbB1, HER1), HER2 (ErbB2 or p185neu), HER3 (ErbB3) and HER4 (ErbB4 or tyro2). A panel of anti-ErbB2 antibodies has been characterized using the human breast tumor cell line SKBR3 (Hudziak et al (1989) Mol. Cell. Biol. 9(3):1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al. are further characterized in Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2): 979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20):14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Several members of the ErbB receptor family are known and include EGFR (ErbB1, HER1), ErbB2 (HER2), ErbB3 (HER3), and ErbB4 (HER4).

The terms "ErbB1", "epidermal growth factor receptor", "EGFR" and "HER1" are used interchangeably herein and refer to EGFR as disclosed, for example, in Carpenter et al (1987) *Ann. Rev. Biochem.*, 56:881-914, including naturally occurring mutant forms thereof (e.g., a deletion mutant EGFR as in Humphrey et al (1990) Proc. Nat. Acad. Sci. (USA) 87:4207-4211). The term erbB1 refers to the gene encoding the EGFR protein product. Antibodies against HER1 are described, for example, in Murthy et al (1987) Arch. Biochem. Biophys., 252:549-560 and in WO 95/25167.

The term "ERRP", "EGF-Receptor Related Protein", "EGFR Related Protein" and "epidermal growth factor receptor related protein" are used interchangeably herein and refer to ERRP as disclosed, for example in U.S. Pat. No. 6,399,743 and U.S. Publication No. 2003/0096373.

The terms "ErbB2" and "HER2" are used interchangeably herein and refer to human HER2 protein described, for example, in Semba et al (1985) Proc. Nat. Acad. Sci. (USA) 82:6497-6501 and Yamamoto et al (1986) Nature, 319:230-234 (Genebank accession number X03363). The term "erbB2" refers to the gene encoding human ErbB2 and "neu" refers to the gene encoding rat p185neu.

The terms "ErbB3" and "HER3" are used interchangeably herein and refer to the receptor polypeptide as disclosed, for example, in U.S. Pat. Nos. 5,183,884 and 5,480,968 as well as in Kraus et al (1989) Proc. Nat. Acad. Sci. (USA) 86:9193-9197. Antibodies against ErbB3 are known in the art and are described, for example, in U.S. Pat. Nos. 5,183,884, 5,480,968 and in WO 97/35885.

The terms "ErbB4" and "HER4" are used interchangeably herein and refer to the receptor polypeptide as disclosed, for example, in EP Pat Application No 599,274; Plowman et al (1993) Proc. Natl. Acad. Sci. USA 90:1746-1750; and Plowman et al (1993) Nature 366:473-475, including isoforms thereof, e.g., as disclosed in WO 99/19488. Antibodies against HER4 are described, for example, in WO 02/18444.

Antibodies to ErbB receptors are available commercially from a number of sources, including, for example, Santa Cruz Biotechnology, Inc., California, USA.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native ErbB ligand or with at least one ligand binding domain of a native ErbB receptor, or they will be at least about 80%, or at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinct, (1991) "Annu Rev. Immunol." 9:457-92. To assess ADCC activity of a molecule of interest, an in vitro ADCC assay, such as that described in U.S. Pat. Nos. 5,500,362 and 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *Proc. Natl. Acad. Sci. USA* 95:652-656 (1998).

"Human effector cells" are leukocytes which express one or more constant region receptors (FcRs) and perform effector functions. Typically, effector cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source thereof, e.g., from blood or PBMCs.

The terms "Fc receptor" or "FcR" are used to describe a receptor that binds to the Fc constant region of an antibody. Typically, FcR is one which binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See review M. in *Daëron*, "Annu Rev. Immunol." 15:203-234 (1997)). FcRs are reviewed in Ravetch and Kinet, "Annu Rev. Immunol"., 9:457-92 (1991); Capel et al (1994) Immunomethods 4:25-34; and de Haas et al (1995) J. Lab. Clin. Med. 126:330-41. Other FcRs are encompassed by the term "FcR" herein. The term also includes the neonatal receptor, FcRn, which is responsible for the transfer of maternal IgGs to the fetus (Guyer et al (1976) J. Immunol., 117:587 and Kim et al (1994) J. Immunol. 24:249).

"Complement dependent cytotoxicity" or "CDC" refers to the ability of a molecule to lyse a target in the presence of complement. The complement activation pathway is initiated by the binding of the first component of the complement system (Clq) to a molecule (e.g., an antibody) complexed with a cognate antigen. To assess complement activation, a CDC assay, e.g., as described in Gazzano-Santoro et al *J. Immunol. Methods,* 202:163 (1996), may be performed.

The term "native antibody" refers to a naturally occurring basic 4-chain antibody unit that is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for μ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region," "HVR," or "HV," refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software.

The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In certain instances, for the VL, the subgroup is subgroup kappa I as in Kabat. In certain instances, for the VH, the subgroup is subgroup III as in Kabat.

"Chimeric antibodies" refers to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Complex" or "complexed" as used here in refers to the association of two or more molecules that interact with each other through bonds and/or forces (e.g., van der waals, hydrophobic, hydrophilic forces) that are not peptide bonds. In certain instances, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin, crosslinker, or a detection agent).

The term "heteromultimer" or "heteromultimeric" as used herein describes two or more polypeptides that interact with each other by a non-peptidic, covalent bond (e.g., disulfide bond) and/or a non-covalent interaction (e.g., hydrogen bonds, ionic bonds, Van der Waals forces, and hydrophobic interactions), wherein at least two of the polypeptides have different amino acid sequences from each other.

An antibody "which binds" a molecular target or an antigen of interest is one capable of binding that antigen with sufficient affinity such that the antibody is useful in targeting a protein or a cell or tissue expressing the antigen, and does not significantly cross-react with other proteins. Such antibodies are useful, for example, as diagnostic and/or therapeutic agents and/or research tools. Typically, the extent of binding of the antibody to a "non-target" protein will be less than about 10% of the binding of the antibody to its particular target protein as determined by typical measurement methods, e.g., fluorescence activated cell sorting (FACS) analysis or radioimmunoprecipitation (RIA) or ELISA.

The term "specific binding" or "specifically binds to" or is "specific for" refers to the binding of an antibody to a target molecule, e.g., a particular polypeptide or an epitope on a particular polypeptide target, and means binding that is measurably different from a non-specific interaction (e.g., a non-specific interaction may be binding to bovine serum albumin or casein). Specific binding can be measured, for example, by determining binding of a target molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope. Examples of target molecules include, but are not limited to, serum soluble proteins and their receptors, such as cytokines and cytokine receptors, adhesins, growth factors and their receptors, hormones, viral particles (e.g., RSV F protein, CMV, StaphA, influenza, hepatitis C virus), microorganisms (e.g., bacterial cell proteins, fungal cells), adhesins, CD proteins and their receptors.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by using surface plasmon resonance assays, for example, using a BIAcore™-2000 or a BIAcore™-3000 (BIAcore, Inc., Piscataway, N.J.) at 25° C. with immobilized antigen CM5 chips at ~10 response units (RU). Briefly, this method uses carboxymethylated dextran biosensor chips (CM5, BIAcore Inc.) activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

A "free cysteine amino acid" refers to a cysteine amino acid residue in a polypeptide, e.g., an antibody or antibody fragment, which has a thiol functional group (—SH) and is not paired as an intramolecular or intermolecular disulfide bridge. In certain instances, a free cysteine amino acid residue has been engineered into a parent antibody as described, for example, in U.S. Patent Pub. No. 2007/0092940 and Junutula, J. R., et al., *J Immunol Methods* 332(1-2):41-52 (2008).

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labeled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests.

A "parent antibody" is an antibody that is a source of one or more antibody fragments. The parent antibody may comprise a native or wild type sequence. The parent antibody may comprise an amino acid sequence from which one or more amino acid residues are replaced by one or more cysteine residues. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. A parent antibody may be directed against nonpolypeptide antigens (such as tumor-associated glycolipid antigens; see, e.g., U.S. Pat. No. 5,091,178. Exemplary parent antibodies include, but are not limited to, antibodies having affinity and selectivity for cell surface and transmembrane receptors and tumor-associated antigens (TAA).

An "isolated" antibody or polypeptide is one which has been identified and separated and/or recovered from a component of its natural environment. Contaminant components of its natural environment are materials which would interfere with, e.g., diagnostic or therapeutic uses, and may include enzymes, hormones, and other proteinaceous or nonproteinaceous solutes. Typically, the antibody or polypeptide will be purified (1) to greater than 95% by weight of protein as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody or polypeptide includes the antibody or polypeptide in situ within recombinant cells since at least one component of the antibody's or polypeptide's natural environment will not be present. Ordinarily, however, isolated antibody or polypeptide will be prepared by at least one purification step.

The phrases "substantially homogeneous", "substantially homogeneous form" and "substantial homogeneity" are used to indicate that the product is substantially devoid of by-products originated from undesired polypeptide combinations (e.g. homomultimers). Expressed in terms of purity, substantial homogeneity means that the amount of by-products does not exceed 10%, 9%, 8%, 7%, 6%, 4%, 3%, 2% or 1% by weight or is less than 1% by weight. Typically, the by-product is below 5%.

A "Lys-C endopeptidase cleavage site" as used herein is a lysine residue in an amino acid sequence that can be cleaved at the C-terminal side by Lys-C endopeptidase. Lys-C endopeptidase cleaves at the C-terminal side of a Lysine residue.

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (trastuzumab, HERCEPTIN®) as in U.S. Pat. No. 5,821,337.

The terms "treat" or "treatment" refer to both therapeutic treatment and prophylactic or preventative measures, wherein the object is to prevent or slow down (lessen) an undesired physiological change or disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival (e.g., as in cancer treatment) as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of an antibody, antibody fragment, or derivative, e.g., multispecific antibody or antibody analog, to treat a disease or disorder in a subject. In the case of tumor (e.g., a cancerous tumor), the therapeutically effective amount of the antibody or antibody fragment (e.g., a multispecific antibody or antibody analog) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment (e.g., multispecific antibody or antibody analog) may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease of 20% or greater, or 50% or greater, or 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth/proliferation. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" an antigenic receptor is one which has significantly higher levels of the receptor, such as ErbB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative PCR (RT-PCR).

The tumors overexpressing ErbB2 (HER2) are rated by immunohistochemical scores corresponding to the number of copies of HER2 molecules expressed per cell, and can been determined biochemically: 0=0-10,000 copies/cell, 1+=at least about 200,000 copies/cell, 2+=at least about 500,000 copies/cell, 3+=about $1$-$2 \times 10^6$ copies/cell. Overexpression of HER2 at the 3+level, which leads to ligand-independent activation of the tyrosine kinase (Hudziak et al (1987) *Proc. Natl. Acad. Sci. USA*, 84:7159-7163), occurs in approximately 30% of breast cancers, and in these patients, relapse-free survival and overall survival are diminished (Slamon et al (1989) *Science,* 244:707-712; Slamon et al (1987) *Science,* 235:177-182).

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

An "allergic or inflammatory disorder" herein is a disease or disorder that results from a hyper-activation of the immune system of an individual. Exemplary allergic or inflammatory disorders include, but are not limited to, asthma, psoriasis, rheumatoid arthritis, atopic dermatitis, multiple sclerosis, systemic lupus, erythematosus, eczema, organ transplantation, age-related macular degeneration, Crohn's disease, ulcerative colitis, eosinophilic esophagitis, and autoimmune diseases associated with inflammation.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases. An autoimmune disease can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.).

The term "cytostatic" refers to the effect of limiting the function of cells, such as limiting cellular growth or proliferation of cells.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, Astrazeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as Thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozcicsin, carzcicsin and bizcicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosinc; arabinoside ("Ara-C"); cyclophosphamide; thiotcpa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum;

etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine velimogene aliplasmid (Vical); LEUVECTIN® vaccine, a plasmid DNA expression vector encoding interleukin-2(IL-2) complexed with a lipid delivery vehicle (Vical); and VAXID® vaccine a naked DNA plasmid that encodes a patient specific idiotype of the B cell tumor immunoglobulin used as a vaccine for low-grade, non-Hodgkin's, B-Cell lymphoma (Vical); PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophcnolatc mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-$\gamma$, -$\beta$, or -$\alpha$ antibodies, anti-tumor necrosis factor-$\alpha$ antibodies (infliximab or adalimumab), anti-TNF$\alpha$ immunoadhesin (ENBREL®, etanercept), anti-tumor necrosis factor-$\beta$ antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-$\beta$; streptodomase; RNA or DNA from the host; FK506; RS-61443; deoxyspergualin; rapamycin; T-cell receptor (Cohen et al., U.S. Pat. No. 5,114,721); T-cell receptor fragments (Offhcr et al. Science 251: 430-432 (1991); WO 90/11294; Ianeway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®)), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®)), carbamazepine (TEGRETOL®)), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu).

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433, Abgenix). The anti-EGFR antibody may be conjugated with a cytotoxic agent, thus generating an immunoconjugate (see, e.g., EP 659,439A2, Merck Patent GmbH). Examples of small molecules that bind to EGFR include ZD1839 or Gefitinib (IRESSA™; Astra Zeneca), Erlotinib HCl (CP-358774, TARCEVA™; Genentech/OSI) and AG1478, AG1571 (SU 5271; Sugen).

Protein kinase inhibitors include tyrosine kinase inhibitors which inhibits to some extent tyrosine kinase activity of a tyrosine kinase such as an ErbB receptor. Examples of such inhibitors include the EGFR-targeted drugs noted in the preceding paragraph as well as quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevec; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. In certain instances, an anti-angiogenic factor herein is an antibody that binds to Vascular Endothelial Growth Factor (VEGF).

An "anti-emetic" is a compound that reduces or prevents nausea in a subject. Anti-emetic compounds include, for example, neurokinin-1 receptor antagonists, 5HT3 receptor antagonists (such as ondansetron, granisetron, tropisetron, and zatisetron), GABAB receptor agonists, such as baclofen, a corticosteroid such as dexamethasone, KENALOG® triamcinolone, ARISTOCORT® triamcinolone acetonide, or NASALIDE® flunisolide, an antidopaminergic, phenothiazines (for example prochlorperazine, fluphenazine, thioridazine and mesoridazine), dronabinol, metroclopramide, domperidone, haloperidol, cyclizine, lorazepam, prochlorperazine, and levomepromazine.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used herein refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al "Prodrugs: A Chemical Approach to Targeted Drug Delivery," *Directed Drug Delivery*, Borchardt et al (ed.), pp. 247-267, Humana Press (1985). Exemplary prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either pIII or pVIII of filamentous phage (Wells and Lowman, (1992) Curr. Opin. Struct. Biol., 3:355-362, and references cited therein). In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991). Phage display includes techniques for producing antibody-like molecules (Janeway, C., Travers, P., Walport, M., Shlomchik (2001) *Immunobiology, 5th Ed.*, Garland Publishing, New York, p627-628; Lee et al).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The terms "linker," "linker unit," "link," "crosslinker," and "crosslink," used interchangeably herein, means a chemical moiety comprising a covalent bond or a chain of atoms that covalently attaches an antibody or antibody fragment to another antibody, antibody fragment, or to a drug moiety. Linkers include a divalent radical such as an alkyldiyl, an arylene, a heteroarylene, moieties such as: —($CR_2$)$_n$O($CR_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. Additional linkers or crosslinkers include bis-maleimido and bis-alkyl halides, pyridyl disulfides, bis-mercurial salts, 5-thio-2-nitrobenzoic acid-mediated crosslinking, and bis-thiosulfonates. Exemplary commercially available crosslinkers include, but are not limited to 1,4-bis(maleimido)butane, (1,4-bismaleimidyl-2, 3-dihydroxybutane), bis(maleimido)hexane, bis(maleimido) ethane, 1,4-Di-[3'-(2'-pyridyldithio)propionamido]butane, 1,6-Hexane-bis-vinylsulfone, Dithio-bismaleimidoethane, 1,8-Bis-maleimido-diethyleneglycol, and 1,11-Bis-maleimido-triethyleneglycol. In certain instances, a homo-trifunctional reagent may be used as a crosslinkcr, for example, Tris[2-maleimidoethyl]amine.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an antibody. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: BME is beta-mercaptoethanol, Boc is N-(t-butoxycarbonyl), cit is citrulline (2-amino-5-ureidopentanoic acid), dap is dolaproine, DCC is 1,3-dicyclohexylcarbodiimide, DCM is dichloromethane, DEA is diethylamine, DEAD is diethylazodiearboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EMI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN(CH$_3$CN) is acetonitrile, MeOH is methanol, Mtr is 4-anisyldiphenylmethyl (or 4-methoxytrityl), nor is (1S,2R)-(+)-norephedrine, PAB is p-aminobenzylcarbamoyl, PBS is phosphate-buffered saline (pH 7), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

A "subject" is a vertebrate, such as a mammal, e.g., a human. Mammals include, but are not limited to, farm animals (such as cows), sport animals, pets (such as cats, dogs and horses), primates, mice, and rats.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubcl et al., Current Protocols in Molecular Biology (Green Publishing Associates and Wiley Interscience, NY, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

A variety of additional terms are defined or otherwise characterized herein.

Compositions and Methods

Multispecific Antibodies and Antibody Analogs

To construct multispecific antibodies, including bispecific antibodies, and antibody analogs as described herein, antibody fragments having at least one free sulfhydryl group is obtained. The antibody fragments may be obtained from parent antibodies, as defined above, including cysteine engineered antibodies. Parent antibodies may be digested enzymatically to produce antibody fragments. Exemplary enzymatic digestion methods include, but are not limited to, pepsin, papain and Lys-C. Exemplary antibody fragments include, but are not limited to, Fab, Fab', F(ab')$_2$, Fv, diabodies (Db); tandem diabodies (taDb), linear antibodies (see U.S. Pat. No. 5,641,870, Example 2; Zapata et al., Protein Eng. 8(10):1057-1062 (1995)); one-armed antibodies, single variable domain antibodies, minibodies (Olafsen et al (2004) Protein Eng. Design & Sel. 17(4):315-323), single-chain antibody molecules, fragments produced by a Fab expression library, anti-idiotypic (anti-Id) antibodies, CDR (complementary determining region), and epitope-binding fragments. Antibody fragments may also be cloned, as DNA fragments encoding said antibody fragments, into plasmid expression vectors or phagemid vectors and expressed directly in E. coli. Antibody enzymatic digestion methods, DNA cloning and recombinant protein expression methods are well known to those skilled in the art, and exemplary methods are provided herein.

Antibody fragments may be purified using conventional techniques and are subjected to reduction to generate a free thiol group. Antibody fragments having a free thiol group are reacted with a crosslinker, for example, bis-maleimide. Such crosslinked antibody fragments are purified and then reacted with a second antibody fragment having a free thiol group. The final product in which two antibody fragments are crosslinked is purified. In certain embodiments, each antibody fragment is a Fab and the final product, in which the two Fabs are linked through bis-maleimide, is referred to herein as bismaleimido-(thio-Fab)$_2$, or bis-Fab.

Such multispecific antibodies and antibody analogs, including bis-Fabs, can be exploited to quickly synthesize a large number of antibody fragment combinations, or structural variants of native antibodies or particular antibody fragment combinations, and to screen those in biological assays for desired activities.

Cysteine Engineered Antibodies

Cysteine engineered antibodies have been described previously. U.S. Patent Pub. No. 2007/0092940 and Junutula, J. R., et al., *J Immunol Methods* 332(1-2):41-52 (2008). Cysteine engineered antibodies can be parent antibodies. These are useful for generating antibody fragments having a free cysteine in a particular location, typically in a constant region, e.g, $C_L$ or $C_H 1$. A parent antibody engineered to contain a cysteine are referred to herein as a "ThioMab" and Fab fragments produced from such cysteine engineered antibodies, regardless of the method of production, are referred to herein as "ThioFabs." As described previously (U.S. Patent Pub. No. 2007/0092940 and Junutula, J. R., et al., *J Immunol Methods* 332(1-2):41-52 [2008]), mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. In addition to having a reactive thiol group, ThioMabs should be selected such that they retain antigen binding capability. The design, selection, and preparation of cysteine engineered antibodies were described in detail previously. U.S. Patent Pub. No. 2007/0092940 and Junutula, J. R., et al., *J Immunol Methods* 332(1-2):41-52 (2008).

Amino acid sequences of certain exemplary light chains (LC) and heavy chains (HC) of such cysteine engineered antibodies and the corresponding wild-type sequences are listed below (the location of the engineered cysteine is shown in bold italics and underlined). Because the engineered cysteines are introduced into the constant regions of heavy or light chains, it is understood that the locations provided below for the introduction of cysteine into those specified antibodies could be used for any antibody containing those, or substantially similar, constant regions.

```
1. HercLC (wild-type)
                                                  (SEQ ID NO.: 1)
DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC
```

```
1. HercLC110Cys
                                                  (SEQ ID NO.: 2)
DIQMTQSPSSLSASVGDRVTITCRASQDVNTAVAWYQQKPGKAPKLLIYSASFLYSGVPS
RFSGSRSGIDFTLIISSLQPEDFATYYCQQHYTTPPTFGQGTKVEIKRTCAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC
```

```
2. HercLC205Cys
                                                  (SEQ ID NO.: 3)
DIQMTQSPSSLSASVGDRVTITCRASQDVNTAVAWYQQKPGKAPKLLIYSASFLYSGVPS
RFSGSRSGIDFTLIISSLQPEDFATYYCQQHYTTPPTFGQGTKVEIKRIVAAPSVFIFPP
SDEQLKSGTASVVCLLNNFYPREAKVQWKVDNALQSGNSQESVTEQDSKDSTYSLSSTLT
LSKADYEKHKVYACEVIHQGLSSPCTKSENRGEC
```

```
4. HercHC (wild-type)
                                                  (SEQ ID NO.: 4)
EVQLVESGGGLVQPGGSLRLSCAASGFNIKDTYIHWVRQAPGKGLEWVARIYPTNGYTRY
ADSVKGRFTISADISKNTAYLQMNSLRAEDTAVYYCSRWGGDGFYAMDYWGQGILVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVICVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

```
5. HercHC118Cys
                                                  (SEQ ID NO.: 5)
EVQLVESGGGLVQPGGSLRLSCAASGFNIKDTYIHWVRQAPGKGLEWVARIYPTNGYTRY
ADSVKGRFTISADISKNTAYLQMNSLRAEDTAVYYCSRWGGDGFYAMDYWGQGILVTCSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK
```

```
6. 2C4LC (wild-type)
                                                  (SEQ ID NO.: 6)
DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC
```

-continued 7. 2C4LC<sup>110Cys</sup>

(SEQ ID NO.: 7)
DIQMTQSPSSLSASVGDRVTITCKASQDVSIGVAWYQQKPGKAPKLLIYSASYRYTGVPS
RFSGSGSGTDFTLTISSLQPEDFATYYCQQYYIYPYTFGQGTKVEIKRT*C*AAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC 8. 2C4HC (VH-CH1) (wild-type)

(SEQ ID NO.: 8)
EVQLVESGGGLVQPGGSLRLSCAASGFTFTDYTMDWVRQAPGKGLEWVADVNPNSGGSIY
NQRFKGRFTLSVDRSKNTLYLQMNSLRAEDTAVYYCARNLGPSFYFDYWGQGTLVTVSSA
STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHT 9. 5A6HC (VH-CH1) (wild-type)

(SEQ ID NO.: 9)
EVKLEESGGGLVQPGGSMKLSCVASGFTFSDAWMDWVRQSPERGLEWVAEIRSKPNNHAT
YYAESVKGRFTISRDDSKSSVYLQMTSLRPEDTGIYYCTHFDYWGQGTTLTVSSAKTTGP
SVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHT 10. 5A6HC<sup>121C</sup>

(SEQ ID NO.: 10)
EVKLEESGGGLVQPGGSMKLSCVASGFTFSDAWMDWVRQSPERGLEWVAEIRSKPNNHAT
YYAESVKGRFTISRDDSKSSVYLQMTSLRPEDTGIYYCTHFDYWGQGTTLTVSS*C*KTIGP
SVFPLAPSSKSTSGGTAALGCLVKDYFPEPVIVSWNSGALTSGVHTFPAVLQSSGLYSLS
SVVTVPSSSLGTQTYICNVNHKPSNTKVDKKVEPKSCDKTHT 11. 5A6LC (wild-type)

(SEQ ID NO.: 11)
DIQMTQSPSSLSASLGERVSLTCRASQEISGYLSWFQQKPDGTIKRLIYAASALDSGVPK
RFSGSWSGSDYSLTISSLESEDFADYYCLQYVSYPLTFGAGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC 12. 5A6LC<sup>110Cys</sup>

(SEQ ID NO.: 12)
DIQMTQSPSSLSASLGERVSLTCRASQEISGYLSWFQQKPDGTIKRLIYAASALDSGVPK
RFSGSWSGSDYSLTISSLESEDFADYYCLQYVSYPLTFGAGTKVEIKRT*C*AAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC 13. 22E7HC (VH-CH1) (wild-type)

(SEQ ID NO.: 13)
EVKLVESGGGLVKPGGSLKLSCAASGFTFSSYGMSWVRQTPEKRLEWVATISGGNNYTFY
PDNLKGRFTISRDNAKNILYLQISSLRSVDTALYYCASLWYRASFAYWGQGTLVTVSSAK
TTGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHT 14. 22E7HC<sup>121C</sup>

(SEQ ID NO.: 14)
EVKLVESGGGLVKPGGSLKLSCAASGFTFSSYGMSWVRQTPEKRLEWVATISGGNNYTFY
PDNLKGRFTISRDNAKNILYLQISSLRSVDTALYYCASLWYRASFAYWGQGTLVTVSS*C*K
TTGPSVFPLAPSSKSTSGGTAALGCLVKDYFPEPVTVSWNSGALTSGVHTFPAVLQSSGL
YSLSSVVTVPSSSLGTQTYICNVNHKPSNIKVDKKVEPKSCDKIHT 15. 22E7LC (wild-type)

(SEQ ID NO.: 15)
DIMMTQSPSSMYASLGERVTITCKASQDINSYLSWFQQKPGKSPKTLISRANRLVDGVPS
RFSGSGSGQDYSLTISSLEYEDMGIYYCLQYDDFPFTFGGGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC 16. 22E7LC<sup>110Cys</sup>

(SEQ ID NO.: 16)
DIMMTQSPSSMYASLGERVTITCKASQDINSYLSWFQQKPGKSPKTLISRANRLVDGVPS
RFSGSGSGQDYSLTISSLEYEDMGIYYCLQYDDFPFTFGGGTKVEIKRT*C*AAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

17. D1-5HC (VH-CH1) (wild-type)

(SEQ ID NO.: 17)
EVQLVESGGGLVQPGGSLRLSCAASGFTFTGNWIHWVRQAPGKGLEWVGEISPSGGYTDY
ADSVKGRFTISADTSKNTAYLQMNSLRAEDTAVYYCARESRVSYEAAMDYWGQGTLVTVS
SASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTH

-continued

18. D1-5LC (wild-type)

(SEQ ID NO.: 18)

DIQMTQSPSSLSASVGDRVTITCRASQDVSTAVAWYQQKPGKAPKLLIYSASFLYSGVPS
RFSGSGSGTDFTLTISSLQPEDFATYYCQQSYPTPYTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

19. D1-5LC$^{110Cys}$ (SEQ ID NO.: 19)

DIQMTQSPSSLSASVGDRVTITCRASQDVSTAVAWYQQKPGKAPKLLIYSASFLYSGVPS
RFSGSGSGTDFTLTISSLQPEDFATYYCQQSYPTPYTFGQGTKVEIKRT$\underline{C}$AAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC 20. C3-101HC (VH-CH1) (wild-type)

(SEQ ID NO.: 20)

EVQLVESGGGLVQPGGSLRLSCAASGFTFSNYWISWVRQAPGKGLEWVGTINPYSGATDY
ADSVKGRFTISADTSKNTAYLQMNSLRAEDTAVYYCARLAVGVFANRYFDYWGQGTLVTV
SSASTKGPSVFPLAPSSKSTSGGTAALGCLVKDYFPEPVTVSWNSGALTSGVHTFPAVLQ
SSGLYSLSSVVIVPSSSLGTQTYICNVNHKPSNIKVDKKVEPKSCDKTH

21. C3-101LC (wild-type)

(SEQ ID NO.: 21)

DIQMTQSPSSLSASVGDRVTITCRASQDVSTAVAWYQQKPGKAPKLLIYSASFLYSGVPS
RFSGSGSGTDFILTISSLQPEDFATYYCQQSYTTPRTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC

22. C3-101LC$^{110Cys}$ (SEQ ID NO.: 22)

DIQMTQSPSSLSASVGDRVTITCRASQDVSTAVAWYQQKPGKAPKLLIYSASFLYSGVPS
RFSGSGSGTDFTLTISSLQPEDFATYYCQQSYTTPRTFGQGTKVEIKRT$\underline{C}$AAPSVFIFPP
SDEQLKSGTASVVCLLNNFYPREAKVQWKVDNALQSGNSQESVIEQDSKDSTYSLSSTLT
LSKADYEKHKVYACEVTHQGLSSPVTKSFNRGEC Because cysteine engineered antibodies are selected to retain the antigen binding capability of their wild type, parent antibody counterparts, they are capable of binding specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The parent antibody may also be a humanized antibody selected from huMAb4D5-1, huMAb4D5-2, huMAb4D5-3, huMAb4D5-4, huMAb4D5-5, huMAb4D5-6, huMAb4-D5-7 and huMAb4D5-8 (Trastuzumab, HERCEPTIN®) as described in Table 3 of U.S. Pat. No. 5,821,337, expressly incorporated herein by reference; humanized 520C9 (WO 93/21319) and humanized 2C4 antibodies.

Multifunctional Multispecific Antibodies and Antibody Analogs

Multispecific antibodies and antibody analogs can be synthesized with modified crosslinkers such that additional functional moieties may be attached to the multispecific antibody or antibody analog. Modified crosslinkers allow for the attachment of any sulfhydryl-reactive moiety. In one embodiment, N-succinimidyl-S-acetylthioacetate (SATA) is attached to bis-maleimide to form bis-maleimido-acetylthioacetate (BMata). After deprotection of the masked thiol group, any functional group having a sulfhydryl-reactive (or thiol-reactive) moiety may be attached.

Exemplary thiol-reactive reagents include a multifunctional linker reagent, a capture, i.e. affinity, label reagent (e.g. a biotin-linker reagent), a detection label (e.g. a fluorophore reagent), a solid phase immobilization reagent (e.g. SEPHAROSE™ (GE Healthcare) a crosslinked, beaded-form of agarose polystyrene, or glass), or a drug-linker intermediate. One example of a thiol-reactive reagent is N-ethyl maleimide (NEM). Such multispecific antibodies or antibody analogs having modified crosslinkers may be further reacted with a drug moiety reagent or other label. Reaction of a multispecific antibody or antibody analog with a drug-linker intermediate provides a multispecific antibody drug conjugate or antibody analog drug conjugate, respectively.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

An albumin-binding peptide (ABP) sequence (Dennis et al. (2002) "Albumin Binding As A General Strategy For Improving The Pharmacokinetics Of Proteins" J Biol. Chem. 277:35035-35043; WO 01/45746) may also be reacted with multispecific antibodies or antibody analogs having modified crosslinkers. Exemplary ABP sequences are described in: (i) Dennis et al (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14.

Mutagenesis

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e. mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed of protocols and formats, including those commercially available, e.g. QuikChange®) Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

Oligonucleotides are prepared by the phosphoramidite synthesis method (U.S. Pat. Nos. 4,415,732; 4,458,066; Beaucage, S, and Iyer, R. (1992) "Advances in the synthesis of oligonucleotides by the phosphoramidite approach", Tetrahedron 48:2223-2311). The phosphoramidite method entails cyclical addition of nucleotide monomer units with a reactive 3' phosphoramidite moiety to an oligonucleotide chain growing on a solid-support comprised of controlled-pore glass or highly crosslinked polystyrene, and most commonly in the 3' to 5' direction in which the 3' terminus nucleoside is attached to the solid-support at the beginning of synthesis (U.S. Pat. Nos. 5,047,524; 5,262,530). The method is usually practiced using automated, commercially available synthesizers (Applied Biosystems, Foster City, Calif.). Oligonucleotides can be chemically labeled with non-isotopic moieties for detection, capture, stabilization, or other purposes (Andrus, A. "Chemical methods for 5' non-isotopic labeling of PCR probes and primers" (1995) in PCR 2: A Practical Approach, Oxford University Press, Oxford, pp. 39-54; Hermanson, G. in Bioconjugate Techniques (1996) Academic Press, San Diego, pp. 40-55, 643-671; Keller, G. and Manak, M. in DNA Probes Second Edition (1993), Stockton Press, New York, pp. 121-23).

The detection of reactive cysteine groups in antibodies can be carried out using an ELISA phage format (The PHESELECTOR [Phage ELISA for Selection of Reactive Thiols]) as described in U.S. Patent Pub. No. 2007/0092940 and Junutula, J. R., et al., *J Immunol Methods* 332(1-2):41-52 (2008).

Protein Expression and Purification

DNA encoding antibodies or antibody fragments is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells such as *E. coli* cells, simian COS cells, Chinese Hamster Ovary (CHO) cells, or other mammalian host cells, such as myeloma cells (U.S. Pat. No. 5,807,715;

U.S. Pub. Nos. 2005/0048572 and 2004/0229310) that do not otherwise produce the antibody protein, to obtain the synthesis of monoclonal antibodies in the recombinant host cells. Review articles on recombinant expression in bacteria of DNA encoding the antibody include Skerra et al (1993) Curr. Opinion in Immunol. 5:256-262 and Plückthun (1992) Immunol. Revs. 130:151-188.

Cysteine engineered antibodies, e.g. ThioFabs, with highly reactive unpaired Cys residues, may be produced by: (i) expression in a bacterial, e.g. *E. coli*, system or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

Exemplary purification procedures include: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from *Staphylococcus aureus* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. The antibody of interest may be recovered from the solid phase by elution into a solution containing a chaotropic agent or mild detergent. Exemplary chaotropic agents and mild detergents include, but are not limited to, Guanidine-HCl, urea, lithium perchlorate, Arginine, Histidine, SDS (sodium dodecyl sulfate), Tween, Triton, and NP-40, all of which are commercially available. Diluting the antibody into a solution containing a chaotropic agent or mild detergent after elution from the column (e.g., mAbSure column) maintains the stability of the antibody post elution and allows for further manipulations as described herein.

Labeled Multispecific Antibodies and Antibody Analogs

Multispecific antibodies and antibody analogs of the invention, particularly those synthesized with modified crosslinkers having a free sulfhydryl group, may be conjugated with any label moiety which can be covalently attached to the antibody through a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labeled multispecific antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

(a) Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xc, $^{177}$Lu, $^{211}$At, or $^{213}$Bi. Radioisotope labeled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in *Current Protocols in Immunology*, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9):1137-1146).

Metal-chelate complexes suitable as antibody labels for imaging experiments are disclosed: U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg ct al (1990) Cancer Res. 50:4221-4226; Vcrcl ct al (2003) J. Nucl. Med. 44:1663-1670; Lee et al (2001) Cancer Res. 61:4474-4482; Mitchell, et al (2003) J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in *Current Protocols in Immunology*, supra, for example. Fluorescent dyes and fluorescent label reagents include those which are commercially available from Invitrogen/Molecular Probes (Eugene, Oreg.) and Pierce Biotechnology, Inc. (Rockford, Ill.).

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in *Methods in Enzym.* (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. Nos. 4,275,149 and 4,318,980.

A label may be indirectly conjugated with a multispecific antibody or antibody analog. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in *Bioconjugate Techniques* Academic Press, San Diego).

Such labeled multispecific antibodies or labeled antibody analogs may be employed in any known assay method, such as ELISA, competitive binding assays, direct and indirect sandwich assays, and immunoprecipitation assays (Zola, (1987) *Monoclonal Antibodies: A Manual of Techniques*, pp. 147-158, CRC Press, Inc.).

A detection label may be useful for localizing, visualizing, and quantitating a binding or recognition event. The labeled multispecific antibodies and labeled antibody analogs of the invention can detect cell-surface receptors. Another use for detectably labeled antibodies is a method of bead-based immunocapture comprising conjugating a bead with a fluorescent labeled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labeling antibodies, typically with the following properties: (i) the labeled antibody should produce a very high signal with low background so that small quantities of antibodies can be sensitively detected in both cell-free and cell-based assays; and (ii) the labeled antibody should be photostable so that the fluorescent signal may be observed, monitored and recorded without significant photo bleaching. For applications involving cell surface binding of labeled antibody to membranes or cell surfaces, especially live cells, the labels typically (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labeled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labeled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372,907), apoptosis (Vermes, "A novel assay for apoptosis. Flow cytometric detection of phosphatidylserine expression on early apoptotic cells using fluorescein labeled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labeled multispecific antibodies and labeled antibody analogs of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Radionuclide imaging labels include radionuclides such as $^3$H, $^{11}$C, $^{14}$C, $^{18}$F, $^{32}$P, $^{32}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. The radionuclide metal ion can be complexed with a chelating linker such as DOTA. Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free sulfhydryl of the modified crosslinker of the multispecific antibodies or antibody analogs of the invention and provide a metal complexing ligand on the antibody (Lewis et al (1998) Bioconj. Chem. 9:72-86). Chelating linker labeling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labeled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Peptide labeling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labelling: A Practical Approach*, Academic Press, London; Means (1990) Bioconjugate Chem. 1:2; Glazer et al (1975) *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) *Chemical Reagents for Protein Modification*, Vols. I and II, CRC Press, New York; Pfleiderer, G. (1985) "Chemical Modification of Proteins", *Modern Methods in Protein Chemistry*, H. Tscheshe, Ed., Walter DeGryter, Berlin and New York; and Wong (1991) *Chemistry of Protein Conjugation and Crosslinking*, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labeled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labeled multispecific antibodies and labeled antibody analogs of the invention may also be used as an affinity purification agent. In this process, the labeled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labeling reagents typically bear reactive functionality which may react (i) directly with the free sulfhydryl of the modified crosslinker to form the labeled multispecific antibody or labeled antibody analog or (ii) with a linker antibody to form the labeled antibody. Reactive functionality of labeling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O-(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Albumin Binding Peptide (Abp)-containing Multispecific Antibodies and Antibody Analogs Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (U.S. Pat. Pub. No. 20040001827). A series of albumin binding peptides were identified by phage display screening (Dennis et al. (2002) "Albumin Binding As A General Strategy For Improving The Pharmacokinetics Of Proteins" J Biol. Chem. 277:35035-35043; WO 01/45746). Compounds of the invention include ABP sequences taught by: (i) Dennis et al (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14.

Albumin Binding (ABP)-containing multispecific antibodies were synthesized by reacting a maleimido-ABP with a multispecific antibody or antibody analog containing a modified crosslinker bearing a free sulfhydryl group.

Exemplary albumin binding peptide sequences include, but are not limited to the amino acid sequences listed in SEQ ID NOS: 23-27:

```
                                          SEQ ID NO: 23
CDKTHTGGGSQRLMEDICLPRWGCLWEDDF

SEQ ID NO: 24
QRLMEDICLPRWGCLWEDDF

SEQ ID NO: 25
QRLIEDICLPRWGCLWEDDF

SEQ ID NO: 26
RLIEDICLPRWGCLWEDD

SEQ ID NO: 27
DICLPRWGCLW
```

The albumin binding peptide (ABP) sequences bind albumin from multiple species (mouse, rat, rabbit, bovine, rhesus, baboon, and human) with Kd (rabbit)=0.3 μM. The albumin binding peptide does not compete with ligands known to bind albumin and has a half life (T½) in rabbit of 2.3 hr.

Drug Conjugates

The multispecific antibodies and antibody analogs of the invention, particularly those synthesized with modified crosslinkers having a free sulfhydryl group, may be conjugated with any therapeutic agent, i.e. drug moiety, which can be covalently attached to the antibody through a reactive sulfhydryl group.

An exemplary embodiment of an antibody-drug conjugate (ADC) compound comprises a multispecific antibody or antibody analog (each referred to in the following discussion as Ab), and a drug moiety (D) wherein the multispecific antibody or antibody analog has been synthesized with a modified crosslinker having a free sulfhydryl group (L) and the antibody is attached through the free sulfhydryl group to D; the composition having Formula I:

where p is 1, 2, 3, or 4. The number of drug moieties which may be conjugated via a thiol reactive linker moiety to a multispecific antibody or antibody analog is limited by the number of reactive thiols which are introduced by the methods described herein.

Another exemplary embodiment of an antibody-drug conjugate compound (ADC) comprises a multispecific antibody or antibody analog (Ab), an albumin-binding peptide (ABP) and a drug moiety (D) wherein the antibody is attached to the drug moiety by a linker moiety (L) and the antibody is attached to the albumin-binding peptide by an amide bond or a second linker moiety; the composition having Formula Ia:

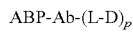

where p is 1, 2, 3, or 4.

The ADC compounds of the invention include those with utility for anticancer activity. In particular, the compounds include an antibody conjugated, i.e. covalently attached by a linker, to a drug moiety, i.e. toxin. When the drug is not conjugated to an antibody, the drug has a cytotoxic or cytostatic effect. The biological activity of the drug moiety is thus modulated by conjugation to an antibody. The multispecific antibody-drug conjugates and antibody analog-drug conjugates (ADC) of the invention selectively deliver an effective dose of a cytotoxic agent to tumor tissue whereby greater selectivity, i.e. a lower efficacious dose, may be achieved.

In one embodiment, the bioavailability of the ADC of the invention, or an intracellular metabolite of the ADC, is improved in a mammal when compared to a drug compound comprising the drug moiety of the ADC and lacking the antibody component. Also, the bioavailability of the ADC, or an intracellular metabolite of the ADC is improved in a mammal when compared to the antibody component of the ADC lacking the drug moiety.

Drug Moieties

The drug moiety (D) of the antibody-drug conjugates (ADC) includes any compound, moiety or group which has a cytotoxic or cytostatic effect. Drug moieties include: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/–C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/–dechloro (U.S. Pat. No. 4,294,757) (prepared by acylation using acyl chlorides). and those having modifications at other positions Exemplary maytansinoid drug moieties also include those having modifications such as: C-9-SH (U.S. Pat. No. 4,424,219) (prepared by the reaction of maytansinol with H$_2$S or P$_2$S$_5$); C-14-alkoxymethyl(demethoxy/CH$_2$OR)(U.S. Pat. No. 4,331,598); C-14-hydroxymethyl or acyloxymethyl (CH$_2$OH or CH$_2$OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

The drug moiety (D) of the antibody-drug conjugates (ADC) of Formula I include maytansinoids having the structure:

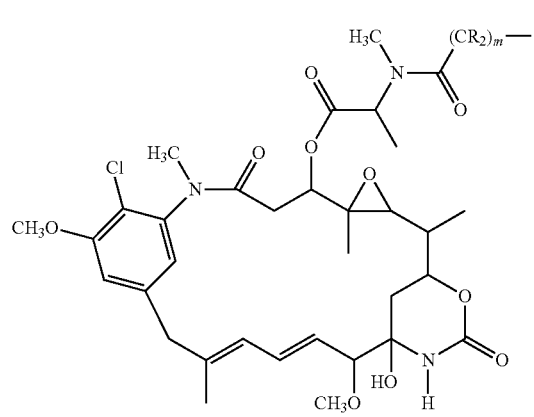

where the wavy line indicates the covalent attachment of the sulfur atom of D to a linker (L) of an antibody-drug conjugate (ADC). R may independently be H or a $C_1$-$C_6$ alkyl selected from methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207).

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines (US 2005/0169933; WO 2005/037992; U.S. Pat. No. 5,208,020).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

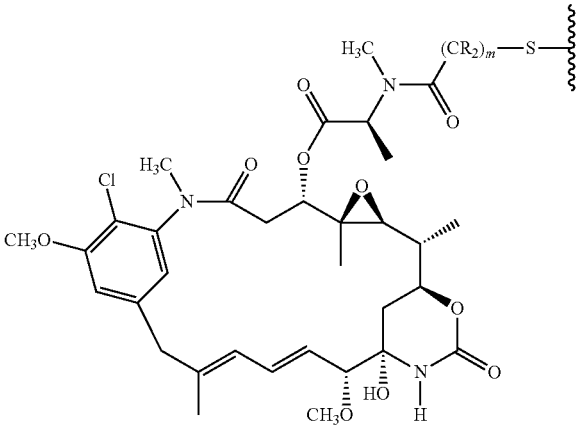

Exemplary embodiments of maytansinoid drug moieties include: DM1, $(CR_2)_m$=$CH_2CH_2$; DM3, $(CR_2)_m$=$CH_2CH_2CH(CH_3)$; and DM4, $(CR_2)_m$=$CH_2CH_2C(CH_3)_2$, having the structures:

DM1

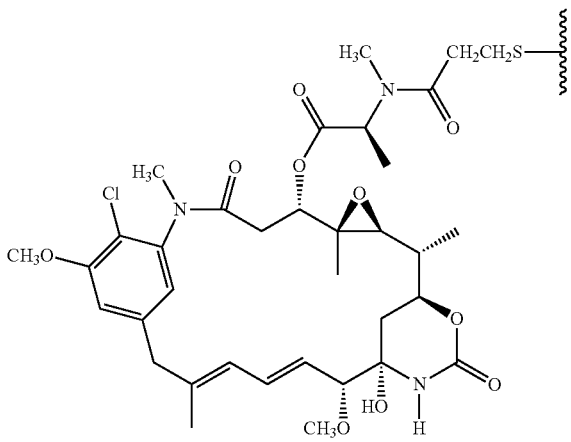

DM3

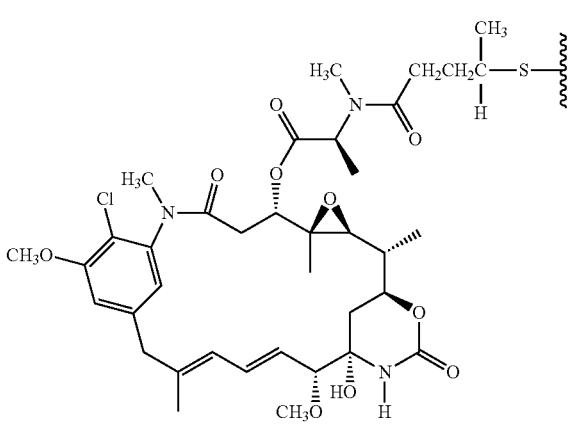

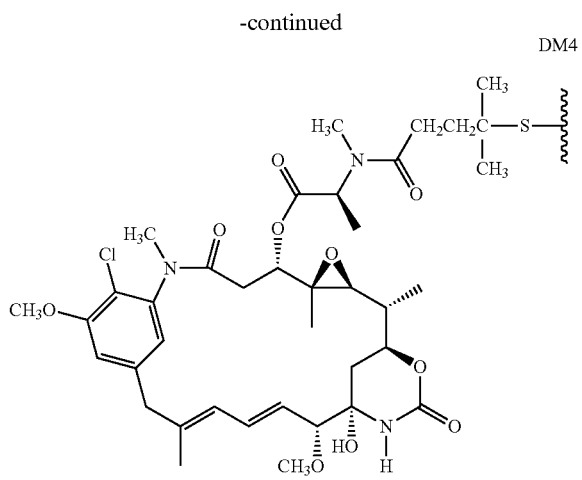

DM4 logs and derivatives thereof. Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in: WO 2005/081711; Senter et al, Proceedings of the American Association for Cancer Research, Volume 45, Abstract Number 623, presented Mar. 28, 2004.

The drug moiety (D) of the antibody-drug conjugates (ADC) of Formula I include the monomethylauristatin drug moieties MMAE and MMAF linked through the N-terminus to the antibody, and having the structures:

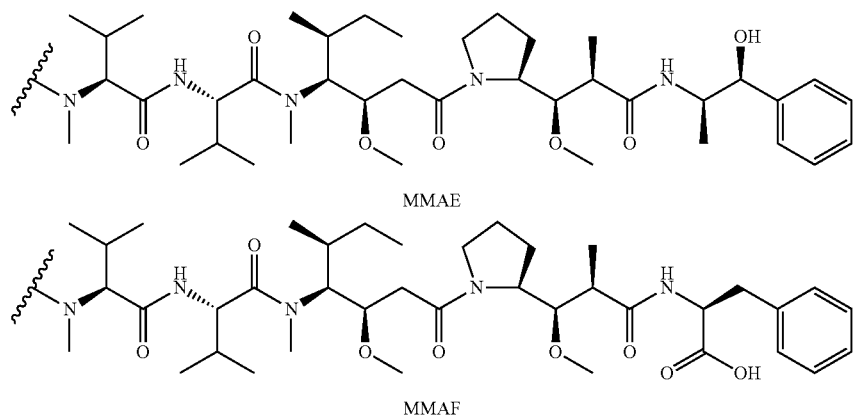

MMAE

MMAF

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

The drug moiety (D) of the antibody-drug conjugates (ADC) of Formula I also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102(4):1458-1465).

Drug moieties include dolastatins, auristatins (U.S. Pat. Nos. 5,635,483; 5,780,588; 5,767,237; 6,124,431), and ana- Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al Cancer Research 53:3336-3342 (1993), Lode et al Cancer Research 58:2925-2928 (1998).

Protein toxins include: diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sap aonaria officinalis inhibitor, gelonin, mitogellin, restrictocin, phenomycin, enomycin, and the tricothecenes (WO 93/21232).

Therapeutic radioisotopes include: $^{32}P$, $^{33}P$ $^{90}Y$, $^{125}I$, $^{131}I$, $^{131}In$, $^{153}Sm$, $^{186}Re$, $^{188}Re$, $^{211}At$, $^{212}Bi$, $^{212}Pb$, and radioactive isotopes of Lu.

The radioisotope or other labels may be incorporated in the conjugate in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triaminepentaacetic acid (MX-DTPA) is an exemplary chelating agent for conjugation of a radionuclide to the antibody (WO 94/11026).

Linkers

A "Linker" (L) is a bifunctional or multifunctional moiety which can be used to link one or more Drug moieties (D) and an antibody unit (Ab) to form multispecific antibody-drug conjugates or antibody analog-drug conjugates (ADC) of Formula I. ADC can be conveniently prepared using a Linker having reactive functionality for binding to the Drug and to the Ab. An Ab can form a bond with a functional group of a linker reagent, a drug moiety or drug-linker intermediate.

In one aspect, a Linker has a reactive site which has an electrophilic group that is reactive to a nucleophilic cysteine present on an antibody or antibody fragment. The cysteine thiol of the antibody or antibody fragment is reactive with an electrophilic group on a Linker and forms a covalent bond to a Linker. Useful electrophilic groups include, but are not limited to, maleimide and haloacetamide groups.

Cysteine engineered antibodies or antibody fragments react with linker reagents or drug-linker intermediates, with electrophilic functional groups such as maleimide or α-halo carbonyl, according to the conjugation method at page 766 of Klussman, et al (2004), Bioconjugate Chemistry 15(4): 765-773, and according to methods described in the Examples.

In one embodiment, linker L of an ADC has the formula:

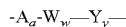

wherein:
-A- is a Stretcher unit covalently attached to a cysteine thiol of the antibody (Ab);
a is 0 or 1;
each —W— is independently an Amino Acid unit;
w is independently an integer ranging from 0 to 12;
—Y— is a Spacer unit covalently attached to the drug moiety; and
y is 0, 1 or 2.

Stretcher Unit

The Stretcher unit (-A-), when present, is capable of linking an antibody unit to an amino acid unit (—W—). In this regard an antibody (Ab) has a free cysteine thiol group or other free thiol group that can form a bond with an electrophilic functional group of a Stretcher Unit. Representative Stretcher units of this embodiment are depicted within the square brackets of Formulas IIIa and IIIb, wherein Ab-, —W—, —Y—, -D, w and y are as defined above, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_1$-$C_8$ heterocyclyl), —$(C_3$-$C_8$ heterocyclyl)-$(CH_2)_r$—, —$(CH_2)_r$C(O)NR$^b$(CH_2)_r$—, —$(CH_2CH_2O)_r$—, —$(CH_2CH_2O)_r$—$CH_2$—, —$(CH_2)_r$C(O)NR$^b$(CH_2CH_2O)_r$—, —$(CH_2)_r$C(O)NR$^b$(CH_2CH_2O)_r$—CH_2$—, —$(CH_2CH_2O)_r$C(O)NR$^b$(CH_2CH_2O)_r$—, —$(CH_2CH_2O)_r$C(O)NR$^b$(CH_2CH_2O)_r$—$CH_2$—, and —$(CH_2CH_2O)_r$C(O)NR$^b$(CH_2)_r$—; where $R^b$ is H, $C_1$-$C_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from a parent aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as III-VI, that even where not denoted expressly, from 1 to 4 drug moieties are linked to an antibody (p=1-4), depending on the number of reactive thiol groups.

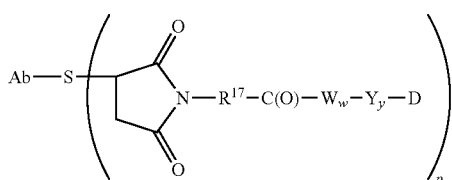

IIIa

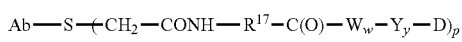

IIIb

An illustrative Stretcher unit is that of Formula IIIa, and is derived from maleimido-caproyl (MC) wherein $R^{17}$ is —$(CH_2)_5$—:

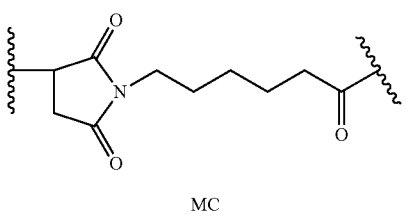 [SMILES: *C(=O)CCCCCN1C(=O)CC(*)C1=O]

MC

An illustrative Stretcher unit is that of Formula IIIa, and is derived from maleimido-propanoyl (MP) wherein $R^{17}$ is —$(CH_2)_2$—:

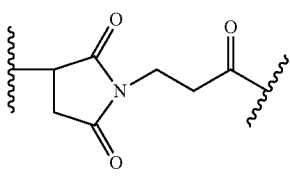

MP

Another illustrative Stretcher unit is that of Formula IIIa wherein $R^{17}$ is —$(CH_2CH_2O)_r$—$CH_2$— and r is 2:

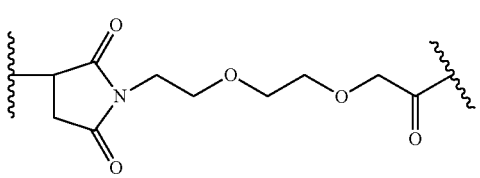 [SMILES: *C(=O)COCCOCCN1C(=O)CC(*)C1=O]

Another illustrative Stretcher unit is that of Formula IIIa wherein $R^{17}$ is —$(CH_2)_rC(O)NR^b(CH_2CH_2O)_r$—$CH_2$— where $R^b$ is H and each r is 2:

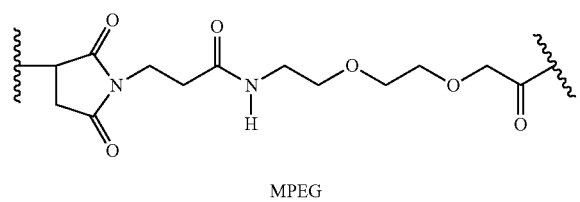 [SMILES: *C(=O)COCCOCCNC(=O)CCN1C(=O)CC(*)C1=O]

MPEG

Another illustrative Stretcher unit is that of Formula IIIb wherein $R^{17}$ is —$(CH_2)_5$—:

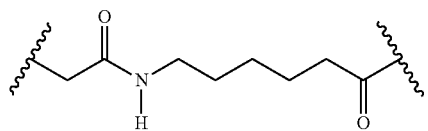 [SMILES: *CC(=O)NCCCCCC(*)=O]

In another embodiment, the Stretcher unit is linked to the antibody unit via a disulfide bond between a sulfur atom of the antibody unit and a sulfur atom of the Stretcher unit. A representative Stretcher unit of this embodiment is depicted within the square brackets of Formula IV, wherein $R^{17}$, Ab-, —W—, —Y—, -D, w and y are as defined above.

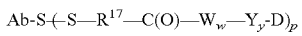

IV

In yet another embodiment, the reactive group of the Stretcher contains a thiol-reactive functional group that can form a bond with a free cysteine thiol or other free thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, Ab-, —W—, —Y—, -D, w and y are as defined above;

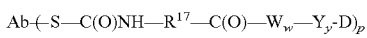

Va

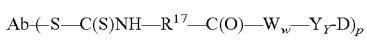

Vb

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

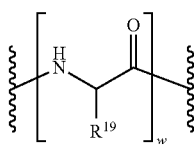

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3$ NHCHO, —$(CH_2)_4NHC(=NH)NH_2$, —$(CH_2)_4$ NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

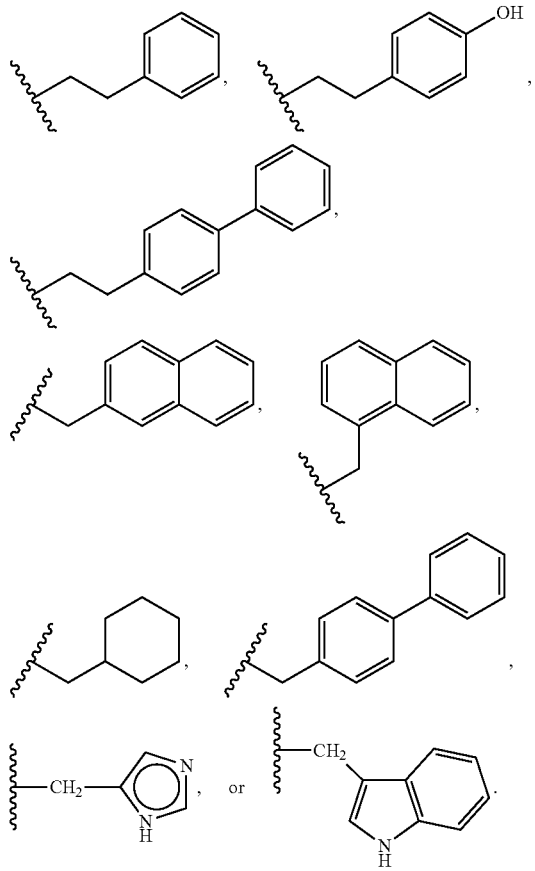

The Amino Acid unit can be enzymatically cleaved by one or more enzymes, including a tumor-associated protease, to liberate the Drug moiety (-D), which in one embodiment is protonated in vivo upon release to provide a Drug (D).

Useful —W$_w$— units can be designed and optimized in their selectivity for enzymatic cleavage by a particular enzymes, for example, a tumor-associated protease. In one embodiment, a —W$_w$— unit is that whose cleavage is catalyzed by cathepsin B, C and D, or a plasmin protease.

Exemplary —W$_w$— Amino Acid units include a dipeptide, a tripeptide, a tetrapeptide or a pentapeptide. Exemplary dipeptides include: valine-citrulline (ve or val-cit), alanine-phenylalanine (af or ala-phe). Exemplary tripeptides include: glycine-valine-citrulline (gly-val-cit) and glycine-glycine-glycine (gly-gly-gly).

When R$^{19}$ is other than hydrogen, the carbon atom to which R$^{19}$ is attached is chiral. Each carbon atom to which R$^{19}$ is attached is independently in the (S) or (R) configuration, or a racemic mixture. Amino acid units may thus be enantiomerically pure, racemic, or diastereomeric.

Spacer Unit

The Spacer unit (—Y$_y$—), when present (y=1 or 2), links an Amino Acid unit (—W$_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-A$_a$-Ww-. In one embodiment, an independent hydrolysis reaction takes place within the target cell, cleaving the glycine-Drug moiety bond and liberating the Drug.

In another embodiment, —Y$_y$— is a p-aminobenzylcarbamoyl (PAB) unit (see Schemes 2 and 3) whose phenylene portion is substituted with Q$_m$ wherein Q is —C$_1$-C$_8$ alkyl, —O—(C$_1$-C$_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —W$_w$— via the amino nitrogen atom of the PAB group, and connected directly to -D via a carbonate, carbamate or ether group, where the ADC has the exemplary structure:

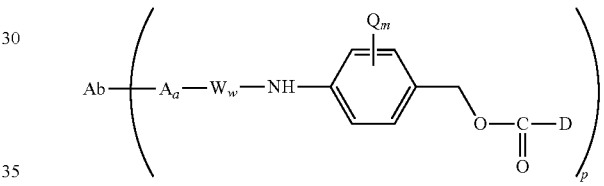

wherein Q is —C$_1$-C$_8$ alkyl, —O—(C$_1$-C$_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

In one embodiment, the Spacer unit is a branched bis (hydroxymethyl)styrene (BHMS), which can be used to incorporate and release multiple drugs, having the structure:

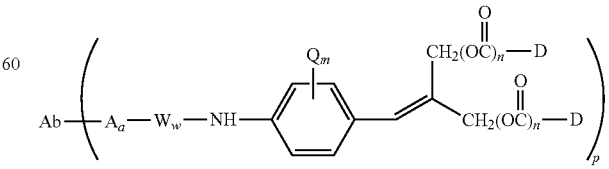

comprising a 2-(4-aminobenzylidene)propane-1,3-diol dendrimer unit (WO 2004/043493; de Groot et al (2003)

Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

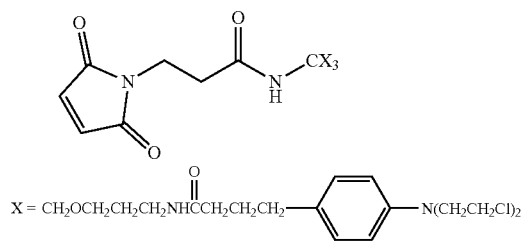

X = $CH_2OCH_2CH_2CH_2NHCCH_2CH_2CH_2$—⟨phenyl⟩—$N(CH_2CH_2Cl)_2$

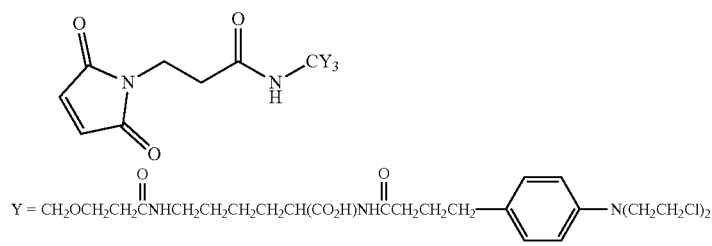

Y = $CH_2OCH_2CH_2CNHCH_2CH_2CH_2CH_2CH(CO_2H)NHCCH_2CH_2CH_2$—⟨phenyl⟩—$N(CH_2CH_2Cl)_2$

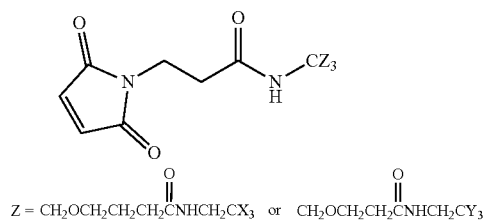

Z = $CH_2OCH_2CH_2CH_2CNHCH_2CX_3$ or $CH_2OCH_2CH_2CNHCH_2CY_3$

In another embodiment of a Spacer unit, branched, dendritic linkers with self-immolative 2,6-bis(hydroxymethyl)-p-cresol and 2,4,6-tris(hydroxymethyl)-phenol dendrimer units (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499) may be employed as linkers in the compounds of the invention.

In another embodiment, the D moieties are the same.

In yet another embodiment, the D moieties are different.

In one aspect, Spacer units (—$Y_y$—) are represented by Formulas (X)-(XII):

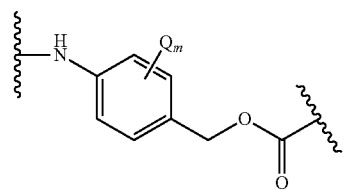

X wherein Q is —$C_1$-$C_8$ alkyl, —O—($C_1$-$C_8$ alkyl), -halogen, -nitro or -cyano; and m is an integer ranging from 0-4;

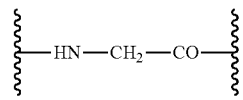

XI

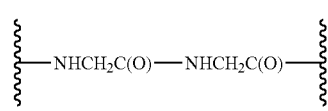

XII

Embodiments of the Formula I antibody-drug conjugate compounds include XIIIa (val-cit), XIIIb (MC-val-cit), XIIIc (MC-val-cit-PAB):

XIIIa

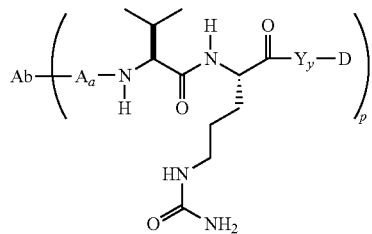

XIIIb

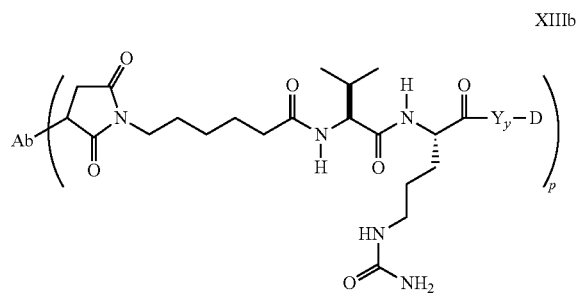

XIIIc

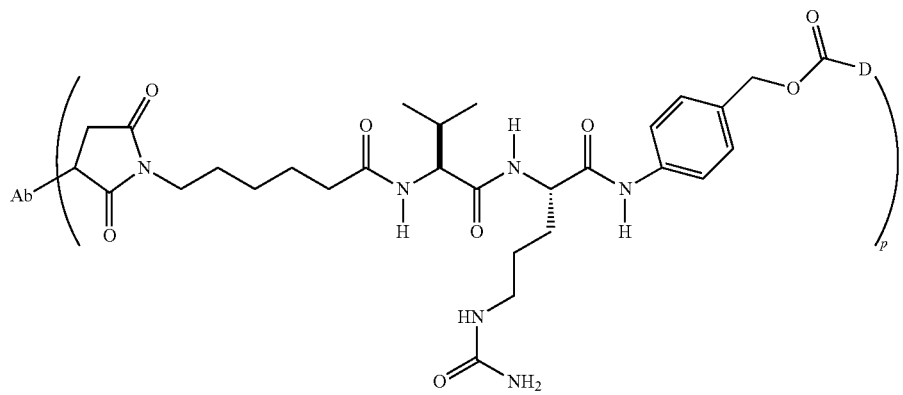

Other exemplary embodiments of the Formula Ia antibody-drug conjugate compounds include XIVa-e:

XIVa

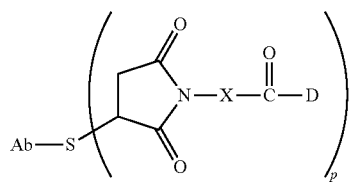

XIVb

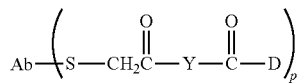

XIVc

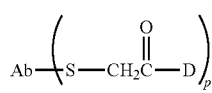

XIVd

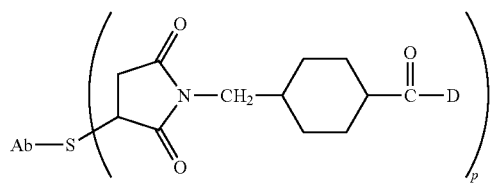

XIVe

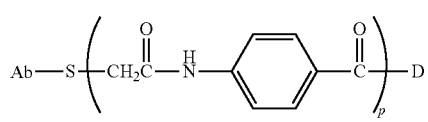

where X is:

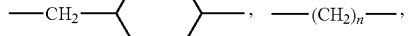

Y is:

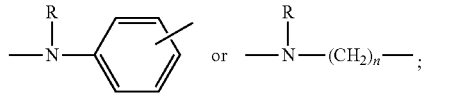

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schroder and K. Liibke (1965) "The Peptides", volume 1, pp 76-136, Academic Press) which is well known in the field of peptide chemistry.

Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to:

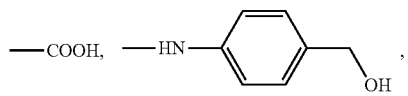

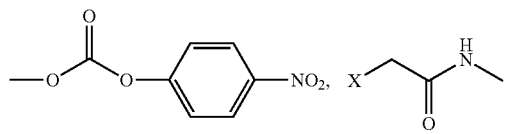

where X is a leaving group, e.g. O-mesyl, O-tosyl, —Cl, —Br, —I; or maleimide.

In another embodiment, the Linker may be substituted with groups which modulated solubility or reactivity. For example, a charged substituent such as sulfonate (—SO$_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

The compounds of the invention expressly contemplate, but are not limited to, ADC prepared with linker reagents: BMPEO, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 U.S.A, U.S.A 1-800-874-3723, International +815-968-0747. See pages 467-498, 2003-2004 Applications Handbook and Catalog. Bis-maleimide reagents allow the attachment of the thiol group of a cysteine engineered antibody or antibody fragment, to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

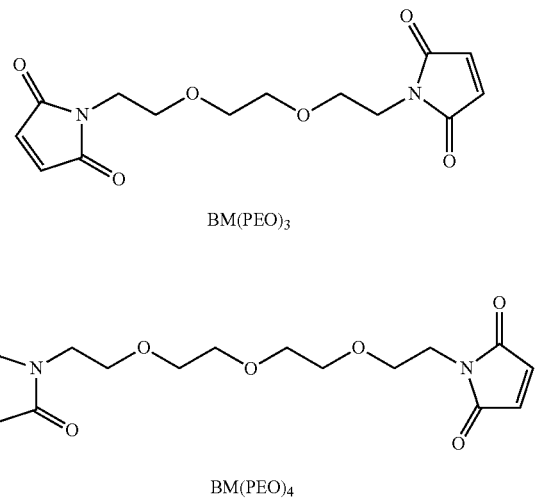

BM(PEO)$_3$

BM(PEO)$_4$

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Stretchers of formula (IIIa) can be introduced into a Linker by reacting the following linker reagents with the N-terminus of an Amino Acid unit:

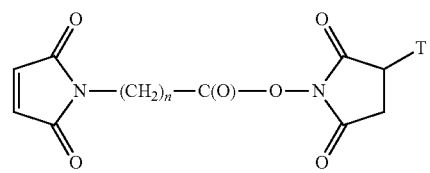

where n is an integer ranging from 1-10 and T is —H or —SO$_3$Na;

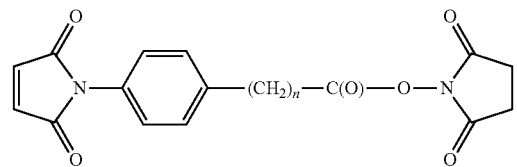

where n is an integer ranging from 0-3;

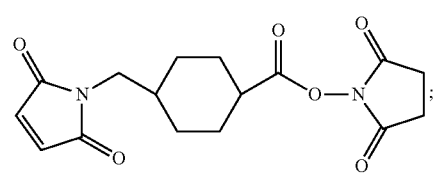

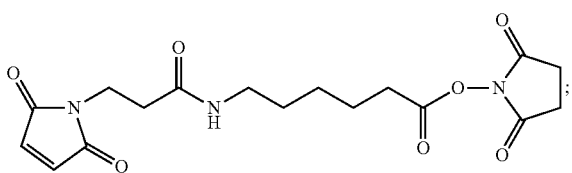

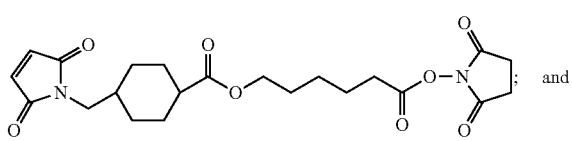

and

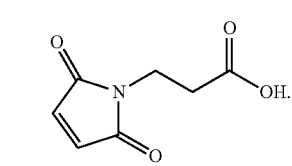

Stretcher units of can be introduced into a Linker by reacting the following bifunctional reagents with the N-terminus of an Amino Acid unit:

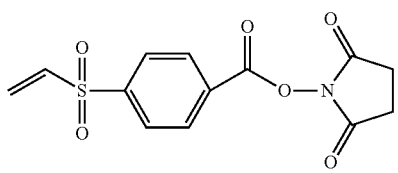

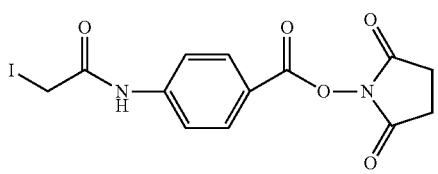

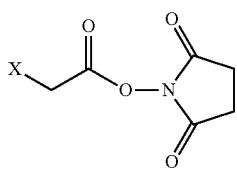

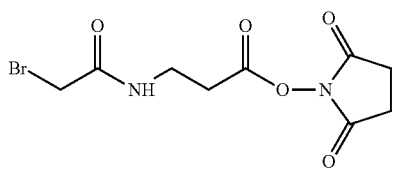

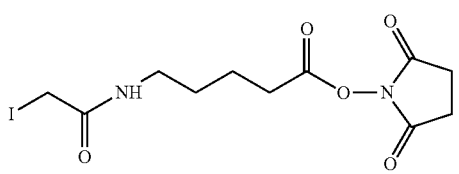

where X is Br or I. Stretcher units of formula can also be introduced into a Linker by reacting the following bifunctional reagents with the N-terminus of an Amino Acid unit:

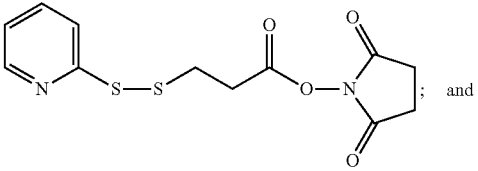

and

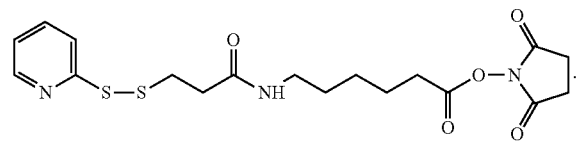

Stretcher units of formula (Va) can be introduced into a Linker by reacting the following intermediates with the N-terminus of an Amino Acid unit:

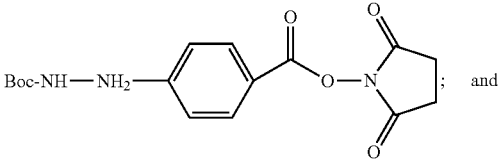

and

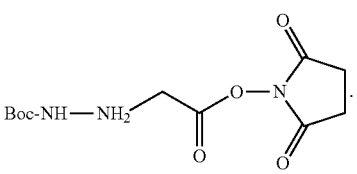

Isothiocyanate Stretchers of the formula shown below may be prepared from isothiocyanatocarboxylic acid chlorides as described in Angew. Chem., (1975) 87(14), 517.

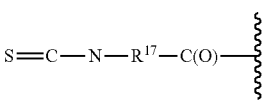

wherein —$R^{17}$— is as described herein.

An exemplary valine-citrulline (val-cit or vc) dipeptide linker reagent having a maleimide Stretcher and a para-aminobenzylcarbamoyl (PAB) self-immolative Spacer has the structure:

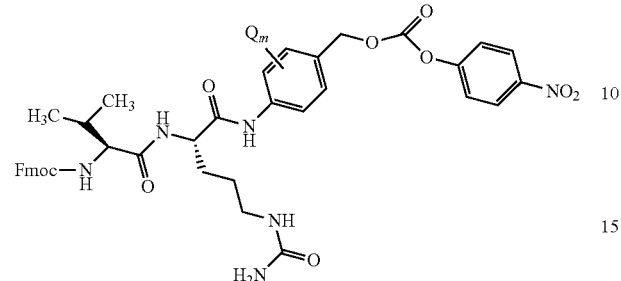

where Q is —$C_1$-$C_8$ alkyl, —O—($C_1$-$C_8$ alkyl), -halogen, -nitro or -cyano; and m is an integer ranging from 0-4.

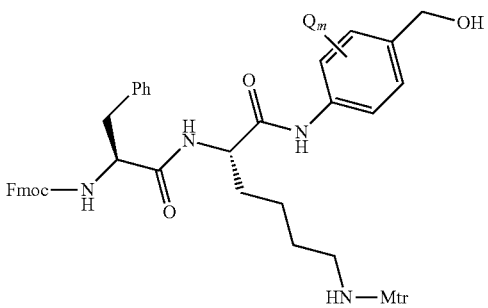

where Mtr is mono-4-methoxytrityl, Q is —$C_1$-$C_8$ alkyl, —O—($C_1$-$C_8$ alkyl), -halogen, -nitro or -cyano; and m is an integer ranging from 0-4.

Exemplary antibody-drug conjugate compounds of the invention include:

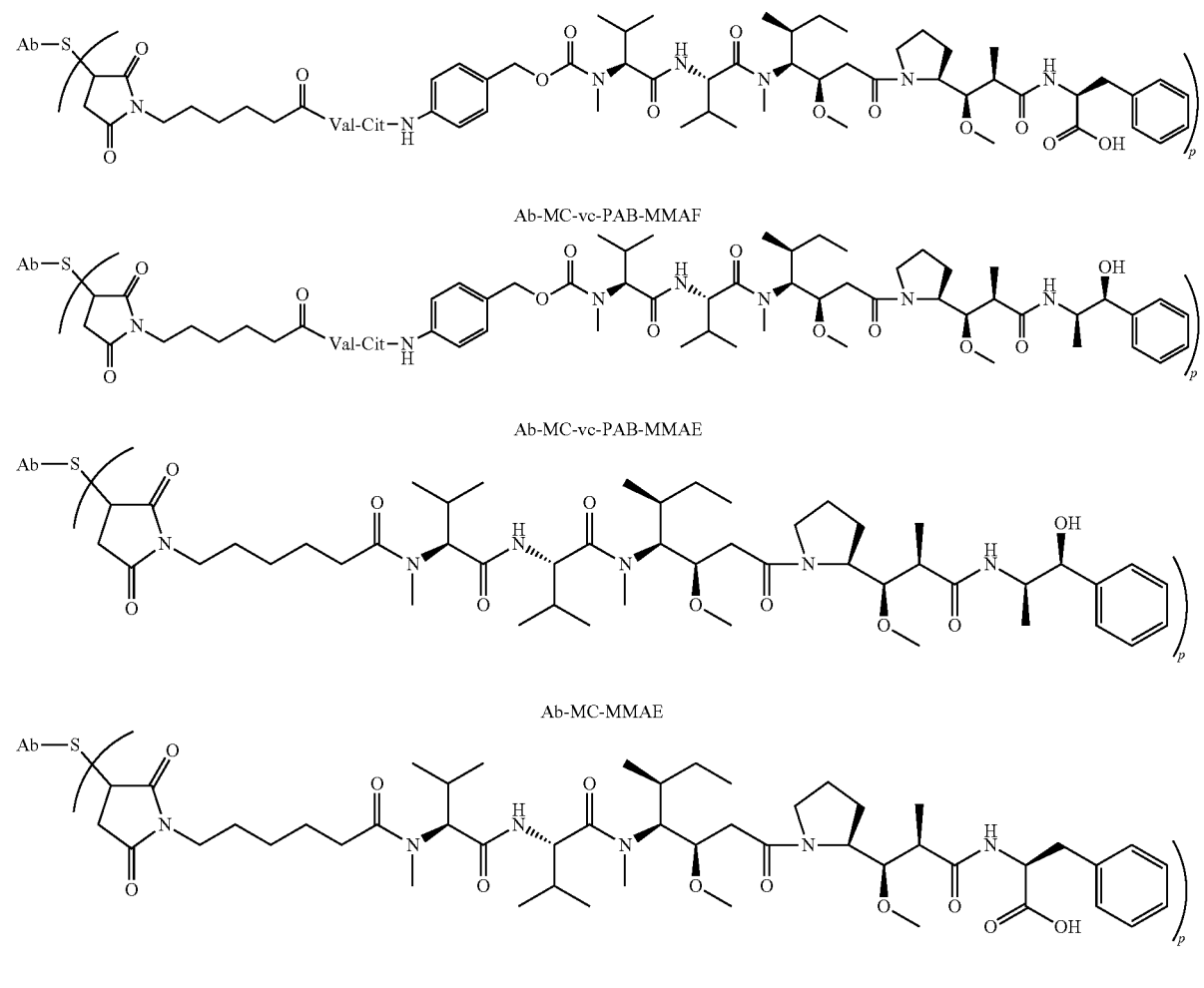

An exemplary phe-lys(Mtr) dipeptide linker reagent having a maleimide Stretcher unit and a p-aminobenzyl self-immolative Spacer unit can be prepared according to Dubowchik, et al. (1997) Tetrahedron Letters, 38:5257-60, and has the structure:

where Val is valine; Cit is citrulline; p is 1, 2, 3, or 4; and Ab is a multispecific antibody or antibody analog. Other exemplary antibody drug conjugates where maytansinoid drug moiety DM1 is linked through a BMPEO linker to a thiol group of trastuzumab have the structure:

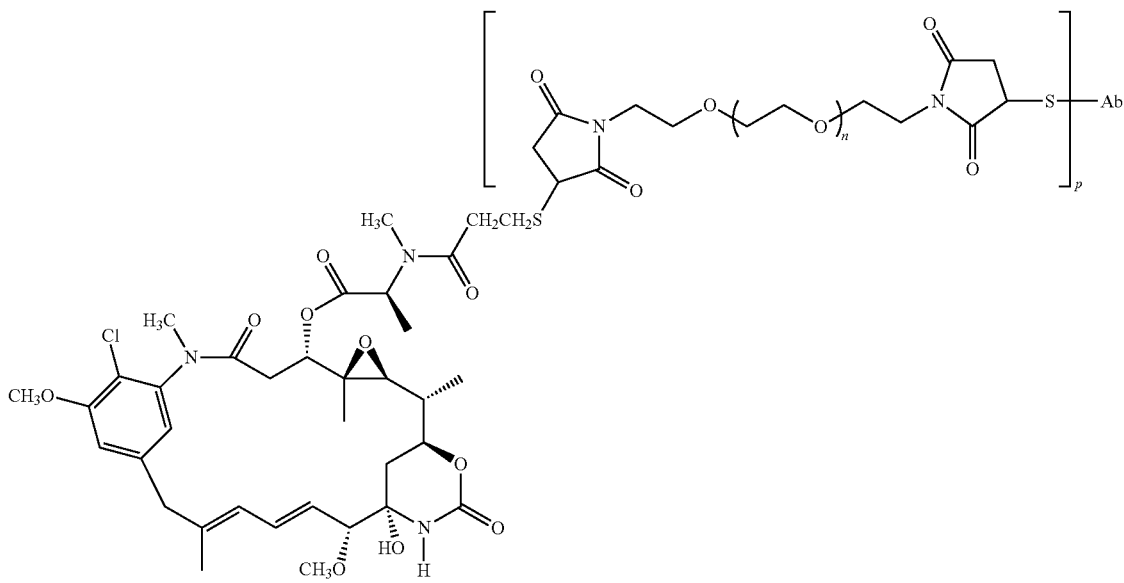

where Ab is an antibody; n is 0, 1, or 2; and p is 1, 2, 3, or 4.

Preparation of Antibody-drug Conjugates

The ADC of Formula I may be prepared by several routes, employing organic chemistry reactions, conditions, and reagents known to those skilled in the art, including: (1) reaction of a cysteine group of a cysteine engineered antibody or antibody fragment with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Maytansine may, for example, be converted to May-SSCH$_3$, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163, 5,208,020, 5,416,064; WO 01/024763). The disulfide linker SPP is constructed with linker reagent N-succinimidyl 4-(2-pyridylthio) pentanoate.

Under certain conditions, the cysteine engineered antibodies or antibody fragments may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies or Fabs (ThioMabs; ThioFabs) expressed in CHO cells can be reduced with about a 50 fold excess of TCEP for 3 hrs at 37° C. to reduce disulfide bonds which may form between the newly introduced cysteine residues and the cysteine present in the culture media. The reduced ThioMabs or ThioFabs can be diluted and loaded onto HiTrap S column in 10 mM sodium acetate, pH 5, and eluted with PBS containing 0.3M sodium chloride. Disulfide bonds can be reestablished between cysteine residues present in the parent Mab with dilute (200 nM) aqueous copper sulfate (CuSO$_4$) at room temperature, overnight. Other oxidants, i.e. oxidizing agents, and oxidizing conditions, which are known in the art may be used. Ambient air oxidation is also effective. This mild, partial reoxidation step forms intrachain disulfides efficiently with high fidelity. An approximate 10 fold excess of drug-linker intermediate, e.g. BM(PEO)$_4$-DM1 can be added, mixed, and let stand for about an hour at room temperature to effect conjugation and form the antibody-drug conjugate. The conjugation mixture can be gel filtered and loaded and eluted through a HiTrap S column to remove excess drug-linker intermediate and other impurities.

In Vitro Cell Proliferation Assays

Generally, the cytotoxic or cytostatic activity of an antibody, e.g., a multispecific antibody or antibody analog of the invention, or antibody-drug conjugate of the invention (ADC) is measured by: exposing mammalian cells having receptor proteins, e.g. HER2, to the antibody or the ADC in a cell culture medium; culturing the cells for a period from about 6 hours to about 5 days; and measuring cell viability. Cell-based in vitro assays are used to measure viability (proliferation), cytotoxicity, and induction of apoptosis (caspase activation) by the multispecific antibodies, antibody analogs and ADC of the invention.

The in vitro potency of multispecific antibodies, antibody analogs, and ADC are measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay can be conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with multispecific antibody, antibody analog or ADC, or they may be treated and separated from antibodies or ADC. Generally, cells treated briefly, i.e. 3 hours, show the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time. Alternatively, photons from luminescence can be counted in a scintillation counter in the presence of a scintillant. The light units can be represented then as CPS—counts per second.

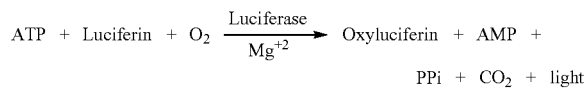

In Vivo Administration

The multispecific antibodies, antibody analogs and antibody-drug conjugates (ADC) of the invention may be administered by any route appropriate to the condition to be treated. Such antibodies will typically be administered parenterally, i.e. infusion, subcutaneous, intramuscular, intravenous, intradermal, intrathecal and epidural.

Pharmaceutical Formulations

Pharmaceutical formulations of therapeutic multispecific antibodies, antibody analogs, and antibody-drug conjugates (ADC) of the invention are typically prepared for parenteral administration, i.e. bolus, intravenous, intratumor injection with a pharmaceutically acceptable parenteral vehicle and in a unit dosage injectable form. A multispecific antibody, antibody analog, or antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ polysorbate surfactant, PLURONICS™ (BASF Corp.) block copolymers based on ethylene oxide and propylene oxide, or polyethylene glycol (PEG). For example, lyophilized anti-ErbB2 antibody formulations are described in WO 97/04801, expressly incorporated herein by reference.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations of multispecific antibodies, antibody analogs or ADC suitable for oral administration may be prepared as discrete units such as capsules, cachets or tablets each containing a predetermined amount of the antibody or ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Certain unit dosage formulations are those containing a daily dose or unit daily sub-dose, as herein above recited, or an appropriate fraction thereof, of the active ingredient.

Veterinary compositions comprising at least one active ingredient as above defined together with a veterinary carrier therefore are also provided. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Therapeutic Uses

The multispecific antibodies, antibody analogs and ADC described herein may be used for therapeutic applications. For example, such antibodies and antibody fragments and antibody-drug conjugates can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific antibodies, antibody analogs, and ADC can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sjogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Examples of allergic or inflammatory disorders or autoimmune diseases or disorders that may be treated using a multispecific antibody, antibody analog, a bis-Fab, an ADC, or any other antibody made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spinooptical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus crythcmatosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, *ascariasis*, aspergillosis, Samptcr's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency vim s (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoncural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T-cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectansis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pncumonocirrhosis, diabetic retinopathy, diabetic large-artery disorder, cndartcrial hyperplasia, peptic ulcer, valvulitis, and endometriosis.

In addition to therapeutic uses, the antibodies of the invention can be used for other purposes, including diagnostic methods, such as diagnostic methods for the diseases and conditions described herein.

Combination Therapy

A multispecific antibody, antibody analog, or antibody-drug conjugate (ADC) of the invention may be combined in a pharmaceutical combination formulation, or dosing regimen as combination therapy, with a second compound having e.g., anti-cancer properties. The second compound of the pharmaceutical combination formulation or dosing regimen preferably has complementary activities to the antibody or ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing a multispecific antibody, antibody analog or ADC of the invention may also have a therapeutically effective amount of a chemotherapeutic agent such as a tubulin-forming inhibitor, a topoisomerase inhibitor, or a DNA binder.

Other therapeutic regimens may be combined with the administration of an anticancer agent. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with a multispecific antibody, antibody analog or ADC involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

The multispecific antibody, antibody analog or ADC may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the antibody or ADC (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Certain Exemplary Target Molecules

Examples of molecules that may be targeted by multispecific antibodies and antibody analogs of this invention include, but are not limited to, soluble serum proteins and their receptors and other membrane bound proteins (e.g., adhesins).

In other embodiments, an antibody analog of the invention is capable of binding one, and a multispecific antibody of the invention is capable of binding one, two or more cytokines, cytokine-related proteins, and cytokine receptors selected from BMP1, BMP2, BMP3B (GDFlO), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FEL1, FEL1 (EPSELON), FEL1 (ZETA), ILIA, IL1B, 1L2, IL3, IL4, IL5, IL6, IL7, IL8, IL9, IL10ILl1, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6

(FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, LL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, 1L1HY1, IL1RAP, IL1RAPL1, IL1RAPL2, IL1RN, 1L6ST, 1L18BP, IL18RAP, 1L22RA2, AIF1, HGF, LEP (leptin), PTN, and THPO.

In another embodiment, a target molecule is a chemokine, chemokine receptor, or a chemokine-related protein selected from CCL1 (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GR03), CXCL5 (ENA-78), CXCL6 (GCP-2), CXCL9 (MIG), CXCL1O (IP 10), CXCLI1 (I-TAC), CXCL12 (SDF1), CXCL13, CXCL14, CXCL16, PF4 (CXCL4), PPBP (CXCL7), CX3CL1 (SCYD1), SCYE1, XCL1(lymphotactin), XCL2 (SCM-Ib), BLR1(MDR15), CCBP2 (D6/JAB61), CCR1(CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1(RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10(C10), EPO, FY (DARC), GDF5, HDF1A, DL8, PRL, RGS3, RGS13, SDF2, SLIT2, TLR2, TLR4, TREM1, TREM2, and VHL.

In other embodiments, an antibody analog of the invention is capable of binding one, and a multispecific antibody of the invention is capable of binding one or more targets selected from ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF (BLys); BAG1; BAI1; BCL2; BCL6; BDNF; BLNK; BLR1 (MDR15); BMP1; BMP2; BMP3B (GDF1O); BMP4; BMP6; BMP8; BMPR1A; BMPR1B; BMPR2; BPAG1(plectin); BR3; BRCA1; C19orflO (IL27w); C3; C4A; C5; C5R1; CANT1; CASP1; CASP4; CAV1; CCBP2 (D6/JAB61); CCL1 (1-309); CCLI1(eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Ia); CCL4 (MDP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBI1); CCR8 (CMKBR8/TER1/CKR-L1); CCR9 (GPR-9-6); CCRL1 (VSHK1); CCRL2 (L-CCR); CD164; CD19; CD1C; CD20; CD180 (RP105); CD200; CD307 (FcRH5); CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1(E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wapl/Cipl); CDKN1B (p27Kipl); CDKN1C; CDKN2A (P161NK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COLIA1; COL4A3; COL6A1; CR2; CRP; CSF1 (M-CSF); CSF2 (GM-CSF); CSF3 (GCSF); CTLA4; CTNNB1(b-catenin); CTSB (cathepsin B); CX3CL1 (SCYD1); CX3CR1 (V28); CXCL1 (GRO1); CXCL10 (IP-10); CXCLI1(1-TAC/IP-9); CXCL12 (SDF1); CXCL13; CXCL14; CXCL16; CXCL2 (GRO2); CXCL3 (GRO3); CXCL5 (ENA-78/L1X); CXCL6 (GCP-2); CXCL9 (M1G); CXCR3 (GPR9/CKR-L2); CXCR4; CXCR6 (TYMSTR/STRL33/Bonzo); CYB5; CYC1; CYSLTR1; DAB21P; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCERIA; FCER2; FCGR3A; FcRH1; FcRH2; FCRL4; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FEL1 (EPSILON); FIL1 (ZETA); FLJ12584; FLJ25530; FLRT1 (fibronectin); FLT1; FOS; FOSL1(FRA-I); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10(C10); GRP; GSN (Gelsolin); GSTP1; HAVCR2; HDAC4; HDAC5; HDAC7A; HDAC9; HGF; HIF1A; HDP1; histamine and histamine receptors; HLA-A; HLA-DOB; HLA-DRA; HM74; HMOX1; HUMCYT2A; ICE-BERG; ICOSL; 1D2; IFN-a; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; ILIA; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAl; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK1O; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS;

MAG or Omgp; MAP2K7 (c-Jun); MDK; MIB1; midkine; MEF; MIP-2; MKI67; (Ki-67); MMP2; MMP9; MS4A1; MSMB; MT3 (metallothionectin-III); MTSS1; MUC1 (mucin); MYC; MYD88; NAG14; NCK2; neurocan; NFKB1; NFKB2; NGFB (NGF); NGFR; NgR-Lingo; NgR-Nogo66 (Nogo); NgR-p75; NgR-Troy; NME1 (NM23A); N0X5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX5; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGSI; RGS13; RGS3; RNFIIO (ZNF144); ROBO2; S100A2; SCGB1D2 (lipophilin B); SCGB2A1 (mammaglobin2); SCGB2A2 (mammaglobin 1); SCYE1 (endothelial Monocyte-activating cytokine); SDF2; SERPINA1; SERPINA3; SERP1NB5 (maspin); SERPINE1(PAI-I); SERPDMF1; SHBG; SLA2; SLC2A2; SLC33A1; SLC43A1; SLIT2; SPP1; SPRR1B (Spr1); ST6GAL1; STAB1; STATE; STEAP; STEAP2; TB4R2; TBX21; TCP10; TDGF1; TEK; TGFA; TGFB1; TGFB1I1; TGFB2; TGFB3; TGFB1; TGFBR1; TGFBR2; TGFBR3; TH1L; THBS1 (thrombospondin-1); THBS2; THBS4; THPO; TIE (Tie-1); TMP3; tissue factor; TLR1O; TLR2; TLR3; TLR4; TLR5; TLR6; TLR7; TLR8; TLR9; TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSF10 (TRAIL); TNFSF1 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Ea); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-Ib); XCR1(GPR5/CCXCR1); YY1; and ZFPM2.

In certain embodiments, one or more molecular target molecules for antibodies encompassed by the present invention include CD proteins selected from CD3, CD4, CD8, CD16, CD19, CD20, CD34, CD64, CD79A, CD79B, CD180 (RP105), CD200, and CD307 (FcRH5); members of the ErbB receptor family selected from the EGF receptor (HER1), HER2, HER3 or HER4 receptor; cell adhesion molecules selected from LFA-1, Mac1, p150.95, VLA-4, ICAM-1, VCAM, alpha4/beta7 integrin, and alphav/beta3 integrin including either alpha or beta subunits thereof (e.g. anti-CD11a, anti-CD18 or anti-CD11b antibodies); growth factors selected from VEGF-A, VEGF-C; tissue factor (TF); alpha interferon (alphaIFN); TNFalpha, an interleukin selected from TL-1beta, IL-3, IL-4, IL-5, IL-8, IL-9, IL-13, IL17A/F, IL-18, IL-13Ralpha1, ILl3Ralpha2, IL-4R, IL-5R, IL-9R, IgE; blood group antigens; flk2/flt3 receptor; obesity (OB) receptor; mpl receptor; CTLA-4; RANKL, RANK, RSV F protein, protein C.

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. Nos. 5,821,337 and 6,407,213 teach bispecific anti-ErbB2/ anti-CD3 antibodies. Additional bispecific antibodies that bind an epitope on the CD3 antigen and a second epitope have been described. See, for example, U.S. Pat. Nos. 5,078,998 (anti-CD3/tumor cell antigen); 5,601,819 (anti-CD3/IL-2R; anti-CD3/CD28; anti-CD3/CD45); 6,129,914 (anti-CD3/malignant B cell antigen); 7,112,324 (anti-CD3/CD19); 6,723,538 (anti-CD3/CCR5); 7,235,641 (anti-CD3/EpCAM); 7,262,276 (anti-CD3/ovarian tumor antigen); and 5,731,168 (anti-CD3/CD4IgG).

In one embodiment, a multispecific antibody of this invention binds to at least two target molecules selected from IL-1alpha and IL-1beta, IL-12 and IL-18; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-13; IL-13 and LHR agonist; IL-12 and TWEAK, IL-13 and CL25; IL-13 and SPRR2a; TL-13 and SPRR2b; IL-13 and ADAMS8, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

In one embodiment, a multispecific antibody of this invention binds to CD3 and at least one additional target molecule selected from BLR1, BR3, CD19, CD20, CD22, CD72, CD79A, CD79B, CD180 (RP105), CR2, FcRH1, FcRH2, FcRH5, FCER2, FCRL4, HLA-DOB, and NAG14.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabeled (e.g. $^{14}$C or $^{3}$H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Imaging Methods

In other embodiments, multispecific antibodies or antibody analogs may be labeled through the reactive thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labeled multispecific antibody or labeled antibody analog, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture

In another embodiment, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds a multispecific antibody, antibody analog or ADC composition which is effective for treating the condition and may have a sterile access port (for example the container may be an intravenous solution bag or a vial having a stopper pierceable by a hypodermic injection needle). At least one active agent in the composition is a multispecific antibody, antibody analog or ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of the methods and compositions of the invention. It is understood that various other embodiments may be practiced, given the general description provided above.

Example 1

Preparation of Thio-Fabs and Hinge-cys-Fabs, Protein Production, and Synthesis of Bispecific Bis-Fabs Preparation of Thio-Fabs and Hinge-cys-Fabs Several approaches were used to create antibody fragments with free sulfhydryl groups for use in subsequent reactions. In one approach, cysteine substitutions were introduced into antibody constructs at various positions in the constant domains of light chains or heavy chains by site-directed mutagenesis to create thio-Mabs as described previously in Junutula, et al. *J Immunol Methods* 332(1-2): 41-52 (2008). Thio-Fabs were generated enzymatically from thio-Mabs by diluting thio-Mabs to 1 mg/mL in 25 mM Tris, pH 8.0, and enzymatically digesting at 37° C. for 1 hr using Lys-C (Wako Chemicals USA, Inc., Richmond, Va.) at a 1:1000 (wt:wt) ratio of enzyme to antibody. The Lys-C digestion was stopped with 5 µM of the protease inhibitor tosyl-L-lysine chloromethyl ketone (TLCK) (Bachem, Torrence, Calif.) and purified by cation ion exchange chromatography on a 5 mL Hi-Trap SP FF column (GE Healthcare, Piscataway, N.J.) using a 50 mM sodium acetate buffer and a 0-300 mM NaCl 10 CV gradient. The thio-Fabs produced by this method are sometimes referred to as "enzymatic thio-Fabs" herein. In another approach, DNA constructs encoding Fabs having an engineered cys residue or DNA constructs encoding heavy chain fragments containing one native cys residue in the hinge region, were subcloned into plasmid expression vectors and expressed directly in *E. coli*. The thio-Fabs produced by this method are sometimes referred to as "recombinant thio-Fabs" herein. A third approach was used for antibodies lacking an engineered cys residue and relied upon the native cys residue(s) present in the hinge region of IgG. This method was used to produce "hinge-cys-Fabs" and is described in further detail below.

For the preparation of hinge-cys-Fabs from native antibodies that did not contain an engineered cysteine for use in synthesis reactions, we used the following enzymatic procedure. While the following procedure was used for trastuzumab, the procedure is generally applicable to any IgG. Trastuzumab was digested with pepsin (1% w/w) by treatment in sodium acetate buffer at pH 4.5. After digestion for 1 hour, the F(ab')2 was isolated from the digestion mixture by capture on an SP-HP cation exchange resin and purified by a 10 CV salt gradient of 0-1 M NaCl. The F(ab')2 was then reduced in a buffer containing 25 mm MES, pH 5.8, 2 mM EDTA, and 300 mM NaCl. After reduction with 1 mM TCEP, the Fabs were oxidized by the addition of 5 mM DHAA to reform the disulfide between the heavy chain and light chain. We routinely observed that under these reaction conditions, only the disulfide between the heavy chain and light chain was reformed; the two cysteine residues in the hinge region remained unoxidized.

The two free thiols (cys residues) at the hinge were then reacted with a 1 molar equivalent of N-ethylmaleimide (NEM) (Sigma Aldrich, St. Louis, Mo.). The resultant mixture containing singly-modified, doubly-modified and unmodified Fabs were then reacted with an excess of the bis-maleimido crosslinker. These reaction conditions yielded three products: Fabs with one crosslinker and one NEM, Fabs with two NEM, and Fabs containing only one crosslinker. The Fabs containing only one crosslinker were found to have no free cysteine. Thus, under these reaction conditions, a single crosslinker reacted very efficiently with both cysteines resulting in a molecule where the cysteines have been cyclized by the crosslinker. The material comprising the above three reaction products was purified from the reaction mixture (to remove unwanted reaction components) by gel filtration and used in coupling to other hinge-cys-Fabs prepared in a similar manner or to thio-Fabs. Only hinge-cys-Fabs or thio-Fabs prepared as described and containing one crosslinker, one free-maleimido and one free sulfhydryl were able to react in the bis-Fab synthesis reactions described in detail below.

Protein Expression and Purification

Protein expression in *E. coli* was carried out either by overnight culturing in shake flasks or in a 10-liter fermentor as described previously. See, e.g., Carter, et al., *Biotechnology* (N Y) 10(2): 163-7 (1992); Simmons, et al., *J Immunol Methods* 263(1-2): 133-47 (2002). In the case of trastuzumab (full length Herceptin®) engineered to contain a reactive cysteine residue (hu4D5-thio-Mab), the antibody was expressed and purified as described in Junutula, et al. *J Immunol Methods* 332(1-2): 41-52 (2008). *E. coli* cell pellets expressing recombinant thio-Fabs or recombinant hinge-cys-Fabs were re-suspended in a buffer containing 25 mM Tris, pH 7.5, 125 mM NaCl, 5 mM EDTA (TEB) and lysed using a microfluidizer. The extract was treated with the flocculent polyethyleneimine (0.4%) adjusted to pH 9.0 for 1 hour with stirring followed by centrifugation for 45 minutes at 15,000×g. Thio-Fabs or hinge-cys-Fabs were purified by standard procedures known in the art using Protein G and cation exchange chromatography. Specifically, the supernatants were filtered through a 0.22 micron filter and then directly applied to a Protein G resin, typically Hi-Trap Protein G (GE Healthcare, Piscataway, N.J.). Elution was done with 0.2 M acetic acid followed by capture with SP-HP cation exchange resin (GE Healthcare, Piscataway, N.J.). Thio-Fabs or hinge-cys-Fabs were eluted with a 10 CV gradient of 0-1 M NaCl. Purified thio-Fabs were characterized by SDS-PAGE and mass spectrometry. These characterizations often showed mass increases of 275 Da and 306 Da. These mass increases were found to be disulfide adducts on the unpaired cysteine which were removed by reduction and oxidation to prepare the thio-Fabs for cross-linking with bis-maleimide. The reduction and oxidation of thio-Fabs was carried out as follows. First, thio-Fabs were reduced for 24 hrs by the addition of 2 mM tris(2-carboxy-ethyl) phosphine HCl(TCEP-HCl; also referred to as TCEP) (Pierce [Thermo Fisher Scientific], Rockford, Ill.) in a buffer containing 25 mM MES, pH 5.8, 300 mL NaCl, and 5 mM EDTA. After reduction, the protein was oxidized by the addition of 5 mM dehydroascorbic acid (DHAA) (Sigma-Aldrich, St. Louis, Mo.). The isolated thio-Fabs were analyzed by SDS-PAGE and mass spectrometry to ensure that the proteins were properly reduced and oxidized.

Bis-Fab Synthesis

FIG. 1 shows the scheme for the synthesis of bis-Fabs. In the first stage of the bis-Fab synthesis, thio-Fabs or hinge-cys-Fabs with an unpaired cysteine were used. Generally, the thio-Fab or hinge-cys-Fab was in the same buffer in which the reduction and oxidation was done (MES, pH 5.8, 2 mM EDTA, and 300 mM NaCl) at a protein concentration of 1 mg/mL (FIG. 1, Panel 1). There are two potential undesired reaction products at this stage, disulfide dimers and crosslinked dimers. We found that a protein concentration of 1 mg/mL at this stage of the synthesis was an important feature of the reaction because dimerization was minimized at that protein concentration. In addition, controlling the reaction by using a low pH buffer with EDTA helped minimize dimerization. A five-fold excess of bis-maleimido crosslinker (Quanta SioDesign, Powell, Ohio) was added to the reaction mixture (FIG. 1, Panel 2). This 5-fold excess of crosslinker was also helpful in minimizing undesirable dimerization. The reaction was incubated at room temperature (RT) or 37° C. for four hours until complete. The mixture was then concentrated to a volume suitable for gel filtration (FIG. 1, Panel 3). We typically used a 22 mL S-200 Tricorn column (GE Healthcare, Piscataway, N.J.) for μg to mg quantity synthesis. This first gel filtration step allowed for the removal of unused crosslinker yielding a purified thio-Fab or hinge-cys-Fab conjugated to the crosslinker. The conditions described above typically resulted in at least 90% or greater of the desired product. No thio-Fab or hinge-cys-Fab remained as free-thiol as all were conjugated to either a crosslinker or bound by disulfide to another thio-Fab or hinge-cys-Fab through the unpaired cysteines.

The isolated and purified thio-Fab (or hinge-cys-Fab) plus crosslinker species was then added to the second thio-Fab (or hinge-cys-Fab) and concentrated to 5 mg/mL or greater, generally to a volume suitable for gel filtration (FIG. 1, Panel 4). We found that a protein concentration of at least 5 mg/mL during this stage of the synthesis was important to drive the reaction to completion. Lower protein concentrations resulted in formation of only small quantities of crosslinked bis-Fab dimers. Without being bound by theory, we hypothesize that a steric effect or viscosity-related variable that hinders formation of cross-linked bis-Fab dimers is overcome by increasing concentrations of reactants. In addition, we tested a range of protein concentrations up to and including 65 mg/mL. We found a correlation between protein concentration and reaction time such that the higher the protein concentration, the faster the reaction reached completion (data not shown). After 2-24 hours at RT or 37° C., the reaction was complete as determined by mass spectrometry (FIG. 1, Panel 4). Generally, one reagent was in excess and remained uncoupled in the final mixture. The completed reaction was again purified by gel filtration; this time we collected the dimeric peak which contains the 100 kD bis-Fab irreversibly crosslinked through the free cysteine amino acid (in the case of thio-Fabs) or through the unpaired cysteine located in the hinge region (in the case of unengineered hinge-cys-Fabs) (FIG. 1, Panel 4). The reaction progress during both steps was often monitored by mass spectrometry which clearly showed the presence of both reactants and the formation of the bis-Fab product (FIG. 1, Panel 4). The purity of the desired product after the second gel filtration was determined by mass spectrometry and SDS-PAGE. Upon reduction and SDS-PAGE analysis, irreversible crosslinking was observed by the presence of a 50 kD band representing non-reducible crosslinked chains (FIG. 1, Panel 5). Using the process described above at small scale, we typically achieved microgram yields with microgram quantities of starting materials. In addition, at a larger scale, we typically achieved milligram yields from milligram quantities of starting materials.

Example 2

Synthesis of Bis-Fabs Targeting Her2 and Her1 and Analysis of Bis-Fab in Vitro Biological Activities To explore various biological activities of bis-Fabs, we synthesized bis-Fabs that target components of the Her axis, specifically Her2 and Her1. The importance of the Her axis in driving cancer cell growth has been well documented and various potent inhibitory antibodies are readily available. See, e.g., Kumar, R. et al., Semin Oncol 27(6 Suppl 11):84-91; discussion at 92-100 (2000); Yarden, Y. et al., Nat Rev Mol Cell Biol 2(2):127-37 (2001); Takai, N. et al., Cancer 104(12):2701-8 (2005); Patel, D. et al., Int J Oncol 34(1): 25-32 (2009). It has been suggested that a combination molecule could provide added or even synergistic benefit over a single antibody therapy. See, e.g., Ranson, et al., Oncology 63 Suppl 1:17-24 (2002); Jackson, J. et al., Cancer Res 64(7):2601-9 (2004); Lee-Hoeflich, S. T. et al., Cancer Res 68(14):5878-87 (2008). This is particularly the case where, as here, two receptors actively collaborate to drive tumor cell growth.

We generated bispecific bis-Fabs from two different antibodies that target Her2 and from two different antibodies that target Her1 (EGFR). The two Her2-targeting antibodies were pertuzumab (2C4) and trastuzumab (Herc). Both of these antibodies are well characterized molecules including knowledge of how they bind their targets. Nature 421(6924): 756-60 (2003); Cancer Cell (4):317-28 (2004). The two Her1-targeting antibodies were D1-5 and C3-101. Both of these antibodies bind to the extracellular domain (ECD) of EGFR and the regions to which they bind on the ECD of EGFR is known (International Patent Application Publication No. WO 2010/108127).

For each of those four antibodies, recombinant thio-Fabs were produced in E. coli as described. Then we synthesized bis-Fabs from these four thio-Fabs in a combinatorial format using a synthesis matrix. We started with approximately 5 mg of each thio-Fab. We combined the different thio-Fabs to synthesize 10 unique molecules as shown in bold in Table 1 below.

phosphorylate Her3 and to activate the signaling pathway and this is inhibited by Herceptin® and Herceptin® Fabs. Id.

Figure 2A:
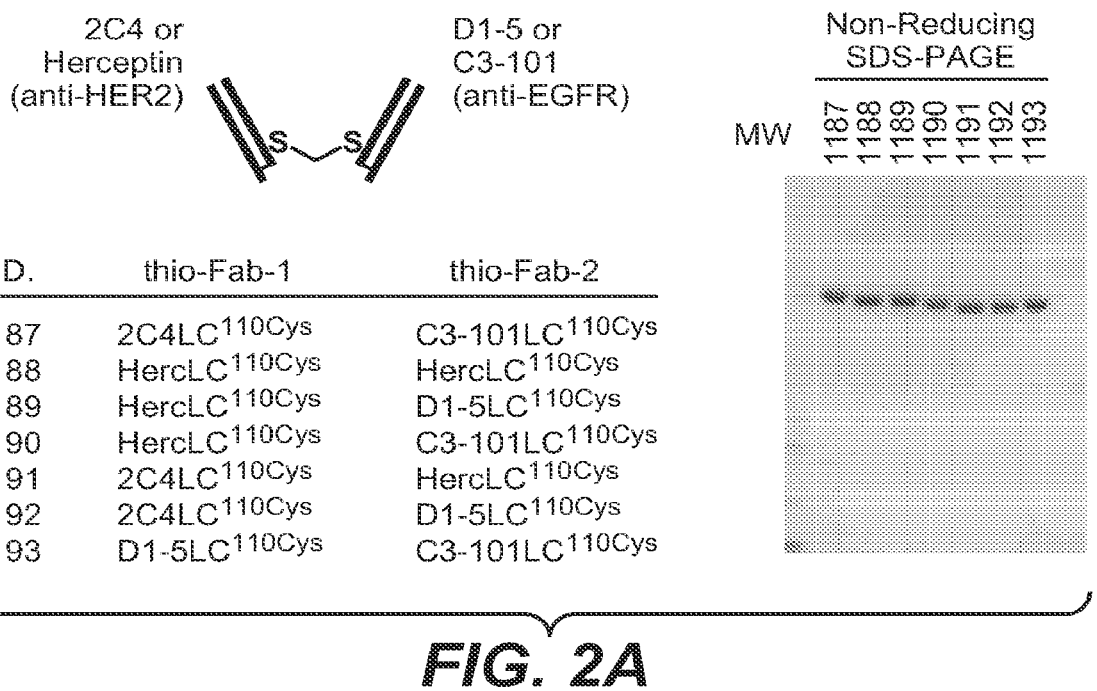
FIG. 2 shows the purity and certain biological properties of certain bis-Fabs as described in Example 2. (A) left side, a schematic of certain bis-Fabs and a table providing bis-Fab identifying numbers and the source of each thio-Fab; right side, non-reducing SDS-PAGE analysis of the bis-Fabs listed in the table; (B) upper panel, inhibition of TGFα-stimulated EGFR phosphorylation in NR-gD-EGFR cells by certain bis-Fabs containing Fabs derived from anti-EGFR antibodies; lower panel, inhibition of Heregulin-induced Hcr3 phosphorylation in MCF7 cells by certain bis-Fabs containing a Fab derived from an anti-Her2 antibody; (C) comparison of the indicated bis-Fab and Fab molecules on the growth of MDA-175 cells; (D) comparison of the indicated bis-Fab, Fab, and antibody molecules on the growth of NR6-EGFR cells; (E) comparison of pertuzumab and the bis-Fab 1204 on the growth of MDA-175 cells; (F) comparison of trastuzumab, trastuzumab-Fab, and the bis-Fab 1188 on the growth of BT474 cells.
Figure 2B:
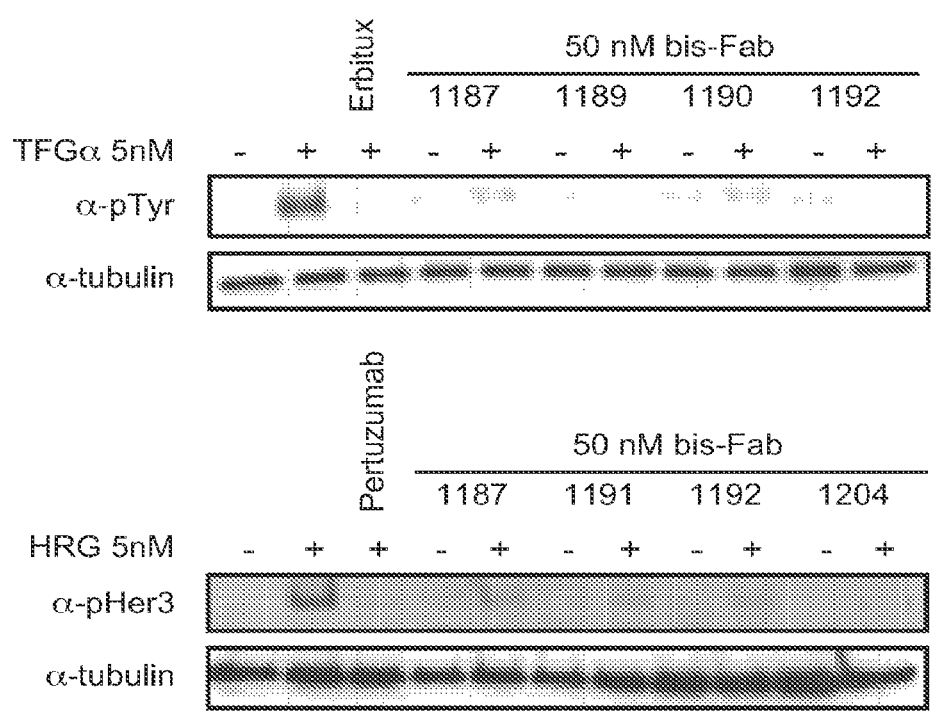

To assay anti-EGFR (anti-Her1) activity of the bis-Fabs, NR6-EGFR cells were treated with 5 nM TGFα to stimulate tyrosine phosphorylation of EGFR followed by treatment with the indicated bis-Fabs (FIG. 2B, upper panel) at a single dose of 50 nM. Each of the bis-Fabs tested, 1187, 1189, 1190, and 1192 contained one Fab derived from an anti-EGFR (anti-Her1) antibody, either D1-5 or C3-101. Phosphorylation activity was analyzed by probing a Western blot with α-pTyr as described in Junttila, T. T., et al., Cancer Cell 15(5): 429-40 (2009). As shown in FIG. 2B upper panel, each of the bis-Fabs tested exhibited potent inhibition of phosphorylation of EGFR in NR6-EGFR cells. Erbitux® (cetuximab) is a monoclonal antibody marketed by Bristol-Meyers Squibb Co. that binds specifically to the ECD of EGFR and was used as a positive control. Blots were probed with α-tubulin to normalize protein loading in each of the lanes.

To assay inhibition of Her2-Her3 dimerization, heregulin (HRG)-induced tyrosine phosphorylation of Her3 in MCF7 cells was monitored by anti-tyrosine Western blotting as described in Junttila, T. T., et al., Cancer Cell 15(5): 429-40 (2009). MCF7 cells were treated with 5 nM HRG to stimulate phosphorylation of Her3 followed by treatment with the indicated bis-Fabs (FIG. 2B, lower panel) at a single dose of 50 nM. Each of the bis-Fabs tested, 1187, 1191, 1192, and 1204 contained at least one Fab derived from an anti-Her2 antibody, 2C4. As shown in FIG. 2B, lower panel, each of the bis-Fabs tested exhibited potent inhibition of Her3 phosphorylation which is the result of preventing Her2-Her3 dimerization. The parent antibody 2C4 (pertuzumab) was used as a positive control. Blots were probed with α-tubulin to normalize protein loading in each of the lanes. Bis-Fab

TABLE 1

Bis-Fab Synthesis Matrix.

| Step 2 (react with bis-Mal-thio-Fabs from Step 1) | Step 1 (+bis-maleimido crosslinker to form bis-Mal-thio-Fab) | | | |
|---|---|---|---|---|
| | $2C4^{V110C}$ | $Herc^{V110C}$ | $D1-5^{V110C}$ | $C3-101^{V110C}$ |
| $2C4^{V110C}$ | $2C4^{V110C}/2C4^{V110C}$ (1204) | $Herc^{V110C}/2C4^{V110C}$ | $D1-5^{V110C}/2C4^{V110C}$ | $C3-101^{V110C}/2C4^{V110C}$ |
| $Herc^{V110C}$ | $2C4^{V110C}/Herc^{V110C}$ (1191) | $Herc^{V110C}/Herc^{V110C}$ (1188) | $D1-5^{V110C}/Herc^{V110C}$ | $C3-101^{V110C}/Herc^{V110C}$ |
| $D1-5^{V110C}$ | $2C4^{V110C}/D1-5^{V110C}$ (1192) | $Herc^{V110C}/D1-5^{V110C}$ (1189) | $D1-5^{V110C}/D1-5^{V110C}$ (1400) | $C3-101^{V110C}/D1-5^{V110C}$ |
| $C3-101^{V110C}$ | $2C4^{V110C}/C3-101^{V110C}$ (1187) | $Herc^{V110C}/C3-101^{V110C}$ (1190) | $D1-5^{V110C}/C3-101^{V110C}$ (1193) | $C3-101^{V110C}/C3-101^{V110C}$ (1401) |

Approximately one mg of each bis-Fab listed in Table 1 was recovered from the synthesis. Each of the bis-Fabs was given a unique identifier as indicated in Table 1 (number in parentheses). The purity of each bis-Fab was analyzed by SDS-PAGE (shown in FIG. 2 A) and mass spectrometry (data not shown). These molecules were tested to determine whether they retained the ability to inhibit cell signaling and cell proliferation similar to the parent antibodies. We tested two specific readouts for cell signaling activity, the phosphorylation of EGFR in response to transforming growth factor (TGFα) and the phosphorylation of Her3 after treatment with heregulin (HRG). The Her3 phosphorylation assay specifically probes the ability of Her2 to dimerize with Her3 in response to heregulin (Junttila, T. T., et al., Cancer Cell 15(5): 429-40 (2009)). Dimerization allows for Her2 to titrations of the molecules showed that the molecules retained effective inhibitory concentrations that were similar to the parent antibody Fabs (data not shown).

We next examined the effect of various bis-Fabs on cell growth in culture. The breast tumor cell lines, MDA-175 (ATCC HTB-25) or BT474 (ATCC No. HTB-20), were used to test bis-Fabs containing anti-Her2 derived Fab(s). In experiments not shown here, we have determined that MDA-175 cells express the Hcr2 receptor. A mouse fibroblast cell line stably transfected with human EGFR, NR6-EGFR cells (see Glading et al., J. Biol. Chem. 275:2390-98 [2000]; Cancer Res. 67(3):1228-38 [2007]), was used to test bis-Fabs containing anti-Her1 derived Fab(s). Each of these cell lines was maintained and propagated using standard cell culture procedures. For the cell proliferation assays, cells were grown to confluence and the media was exchanged for fresh media (DMEM:F12, 10% FCS, PenStrep, Glutamax). The cells were trypsinized for harvest, washed by centrifugation, and exchanged into new media containing 1% serum. Cells were adjusted to a density of 20,000 cells per mL and 250 µL were added to each well of 96-well plate (5,000 cells/well). Plated cells were grown overnight and then challenged the following day by adding antibody reagents (e.g., bis-Fabs) directly to the wells. Cells were grown under these conditions for five days, after which the media was aspirated from the wells and replaced with 250 µL of fresh media. Alamar blue (25 µL) was added to each well and incubated at 37° C. for 3-4 hours. The plate was read in a fluorescent plate reader at 545/590 nm (excitation/emission). The amount of cell proliferation was either reported directly in relative fluorescent units (RFUs) or by normalizing to controls.

Figure 2C:
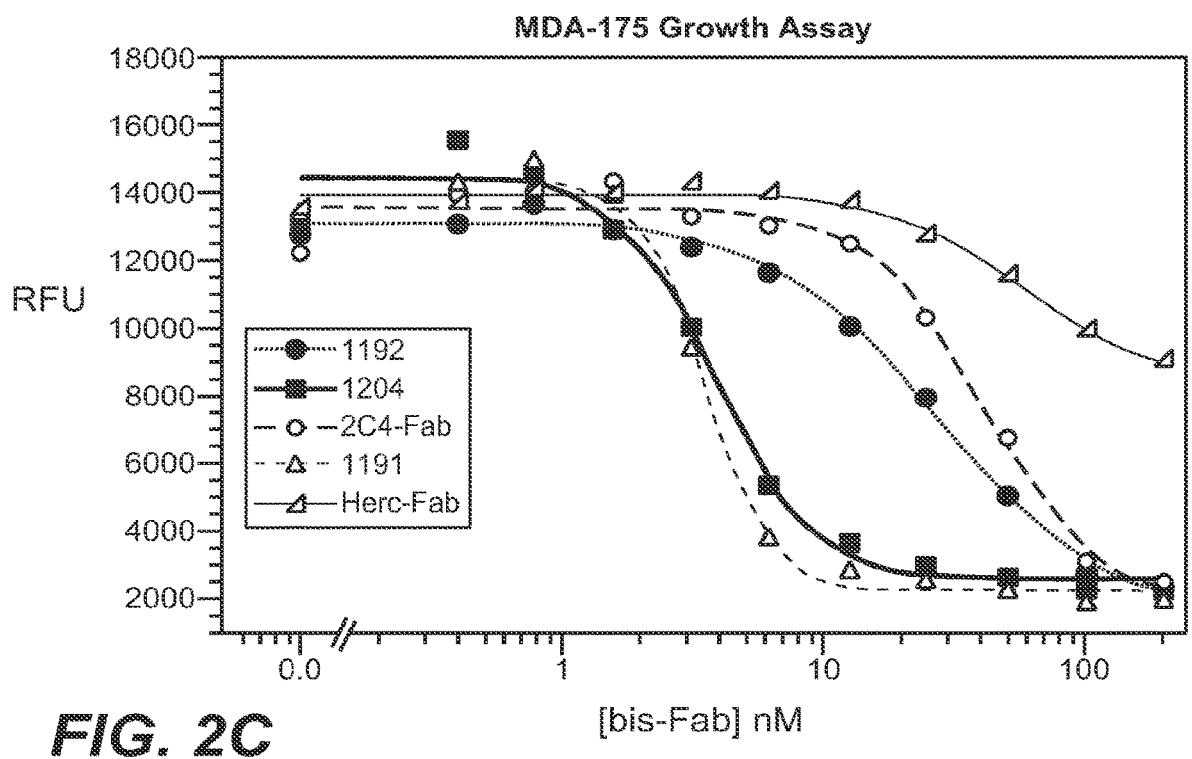
Figure 2D:
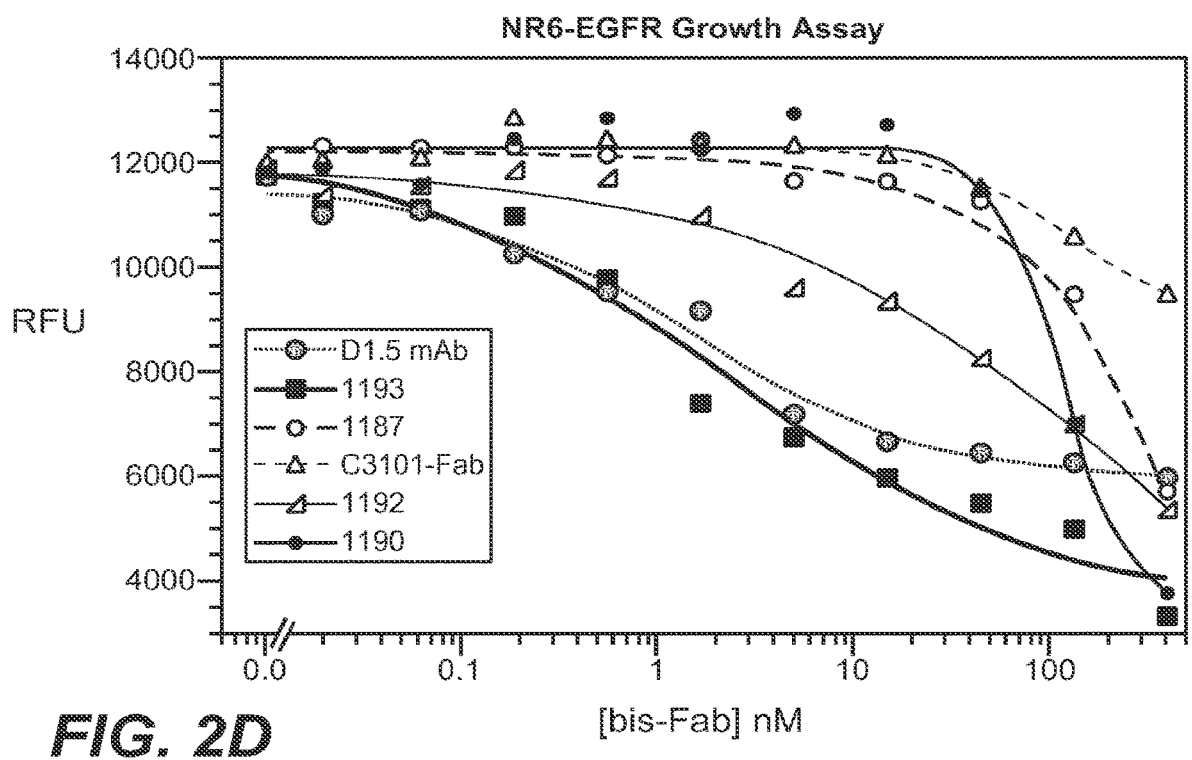

FIGS. 2C and 2D show the results of testing various bis-Fabs on the indicated cell lines for their effects on cell growth. FIG. 2C shows that the bis-Fabs 1191 and 1204, each containing two anti-Her2 Fabs, were the most potent inhibitors of MDA-175 cell growth. The single-Fab molecules, 2C4-Fab and Herc-Fab, were the least potent inhibitors, and the bis-Fab 1192, which contains one anti-Her2 Fab and one anti-Her1 Fab was intermediate in its ability to inhibit MDA-175 cell growth in this experiment. FIG. 2D shows that the bis-Fab 1193, containing two anti-Her1 Fabs, was a potent inhibitor of NRG-EGFR cell growth, similar to the D1-5 (anti-Her1) monoclonal antibody. Bis-Fabs containing one anti-Her1 Fab, as well as the C3-101-Fab, while still displaying growth inhibitory activity, were less potent inhibitors. Accordingly, these results show that 2C4- and Herc-containing bis-Fabs (1192, 1204, and 1191) were able to inhibit cell proliferation in MDA-175 cells that express Her2. And bis-Fabs that contain anti-EGFR Fab(s) (1187, 1190, 1192, and 1193) were able to inhibit cell proliferation in an EGFR expressing cell lines (NR6-EGFR).

Figure 2E:
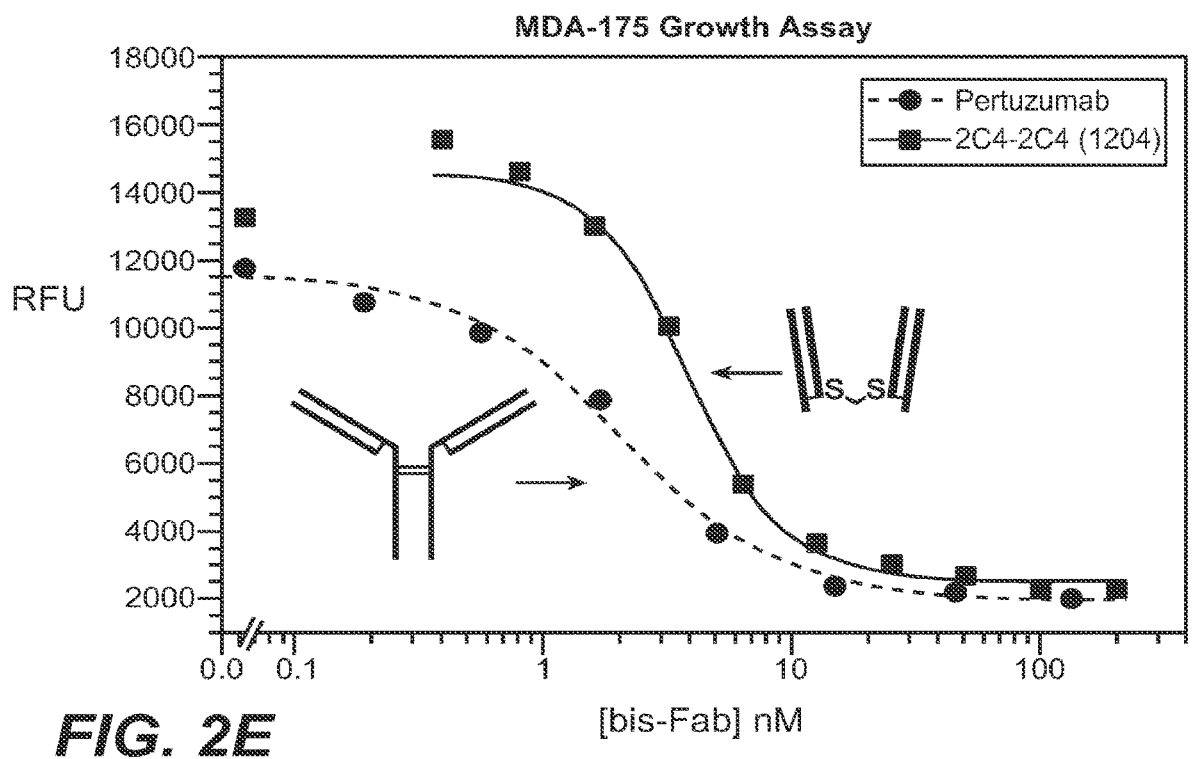

Next, we directly compared the in vitro cell-growth inhibitory activity of two bis-Fabs that are structural analogs of their parent antibodies to the in vitro cell-growth inhibitory activity of their parent antibody. The first comparison was between pertuzumab (2C4) and bis-Fab 1204 ($2C4^{V110C}/2C4^{V110C}$) on MDA-175 cells. FIG. 2E shows that the LC-110C-linked 2C4 bis-Fab appeared to exhibit biphasic activity in inhibiting MDA-175 cell proliferation in this experiment. At lower concentrations (1 nM), the bis-Fab appeared to stimulate growth while at higher concentrations it was inhibitory. The half-maximal inhibition was at ~2 nM compared to the parent antibody, pertuzumab.

Figure 2F:
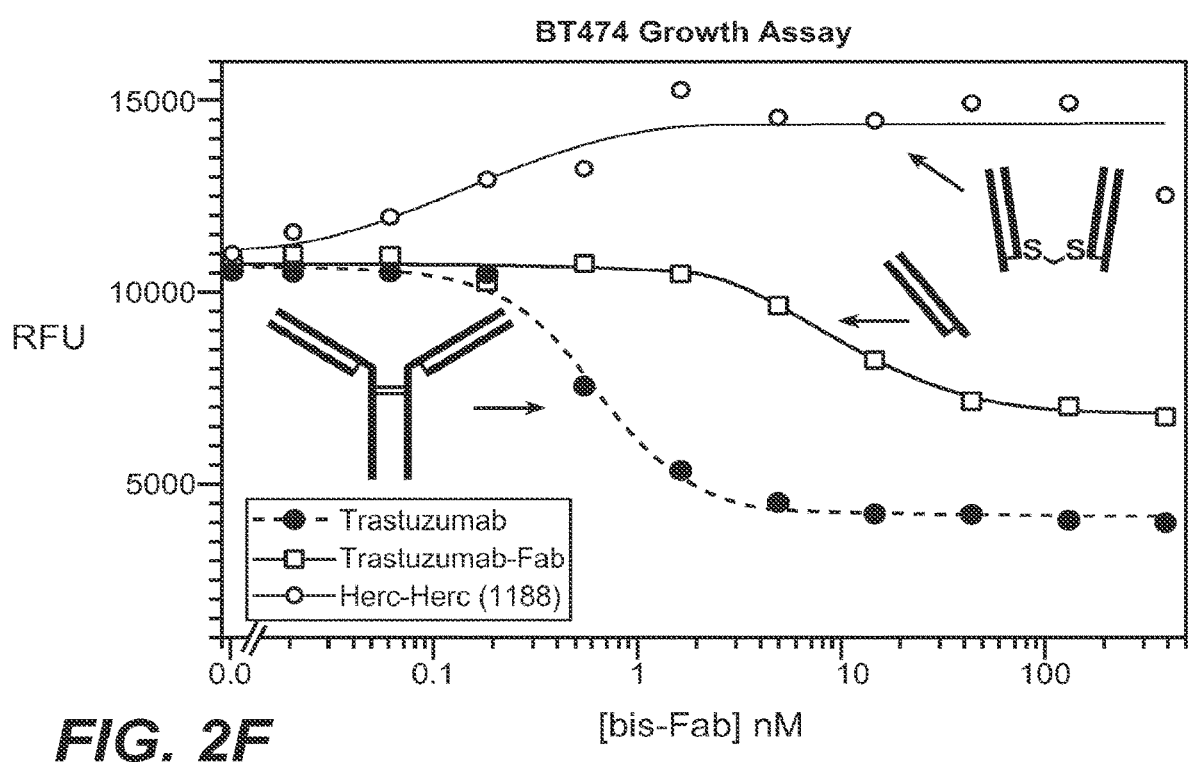

The second comparison was between trastuzumab and the bis-Fab 1188 ($Herc^{V110C}/Herc^{V110C}$) on BT474 cells, which overexpress Her2. We also included the trastuzumab-Fab in this experiment. The results are shown in FIG. 2F. Based on the results we observed with pertuzumab and bis-Fab 1204, discussed above, we expected to observe in this experiment that bis-Fab 1188 would inhibit BT474 cell proliferation similar to the parent antibody, trastuzumab. FIG. 2F shows that, as expected, trastuzumab strongly inhibited BT474 cell proliferation and the trastuzumab-Fab was a less potent inhibitor of cell growth. Surprisingly, however, we observed that bis-Fab 1188 had exactly the opposite effect on cell proliferation. As clearly shown in FIG. 2F, bis-Fab 1188 strongly promoted BT474 cell growth. BT474 cells rapidly proliferate even in the absence of any exogenous agonists, and in fact, there are no known agonists of this cell line. Given these proliferative properties of the BT474 cell line, the discovery that bis-Fab 1188 could function as an agonist of these cells was particularly surprising and unexpected.

One structural difference between the Fab arms of trastuzumab and the Fabs of bis-Fab 1188 is the site of conjugation. In contrast to the parent antibody which has the typical IgG structure with the Fabs joined through their heavy chains, the two thio-Fabs of bis-Fab 1188 are conjugated through their light chains at a position between the variable and first constant domain. Because no ligand for Her2 has been identified that directly activates the receptor (Yarden, Y. et al., *Nat Rev Mol Cell Biol* 2(2):127-37 (2001); Jackson, J. et al., *Cancer Res* 64(7):2601-9 (2004)), it was unexpected that such a structural difference between the bis-Fab and the parent antibody would result in the bis-Fab having agonist activity rather than the antagonist activity of its parent. Therefore, the identification of a trastuzumab analog having agonist activity under these conditions was quite surprising. We wondered whether other variations in structure could influence the biological activity of the molecules. We therefore developed a structural array, or analog library, of crosslinked variants by generating four different thio-Fabs derived from trastuzumab. These are discussed in further detail below.

Example 3

Synthesis of and Characterization of Trastuzumab-derived Bis-Fab Structural Variants Using the matrix recombination approach described above, we synthesized a series of trastuzumab-derived bis-Fab structural variants. We chose four different thio-attachment points to synthesize the bis-Fabs; two of the positions were in the heavy chain and two of the positions were in the light chain. Fabs containing thio-attachment points were derived from three different sources; 1) thio-Mabs with cysteine substitutions that were digested with Lysine-C to liberate the thio-Fab from the antibody, 2) thio-Fabs with cysteine substitutions that were directly expressed in and purified from *E. coli*, and 3) hinge-cys-Fabs generated by the enzymatic method described above for the attachment of a single crosslinker to the hinge region of a non-engineered antibody after digestion with pepsin. This approach produced four different substitution points in thio-Fabs for recombination with other thio-Fabs, thus yielding a panel of structural variants (FIG. 3A). The four different substitution positions are in the light chain at position 110 ($LC^{110Cys}$), the light chain at position 205 ($Lc^{205Cys}$), the heavy chain at position 118 ($HC^{118Cys}$), and the heavy chain at the hinge region ($HC^{Hg-Cys}$). The synthesis was done in matrix format in which the set of four thio-Fabs were first conjugated with the crosslinker and then re-combined with each other to produce 16 molecules, 10 of which were unique in mass and structure. The thio-Fabs are depicted schematically in FIG. 3A along with a listing of the unique identifiers for the bis-Fabs synthesized and the source of each thio-Fab for each bis-Fab. The final purified products from the synthesis reactions were characterized by mass spectrometry to ensure purity of the test material. In addition, we analyzed the molecular weight of the bis-Fabs by non-reducing SDS-PAGE (FIG. 3B). As shown in FIG. 3B, all of the bis-Fab structural variants had vastly different apparent molecular weights, an interesting result considering that each of the source thio-Fabs were of the same molecular weight and the same crosslinker was used to synthesize each bis-Fab. The most likely explanation for the different apparent molecular weights is that the linkage sites (the thio attachment points)

create structural variants that are observed in the linearly extended polypeptide that occurs in denaturing conditions.

Figure 3C:
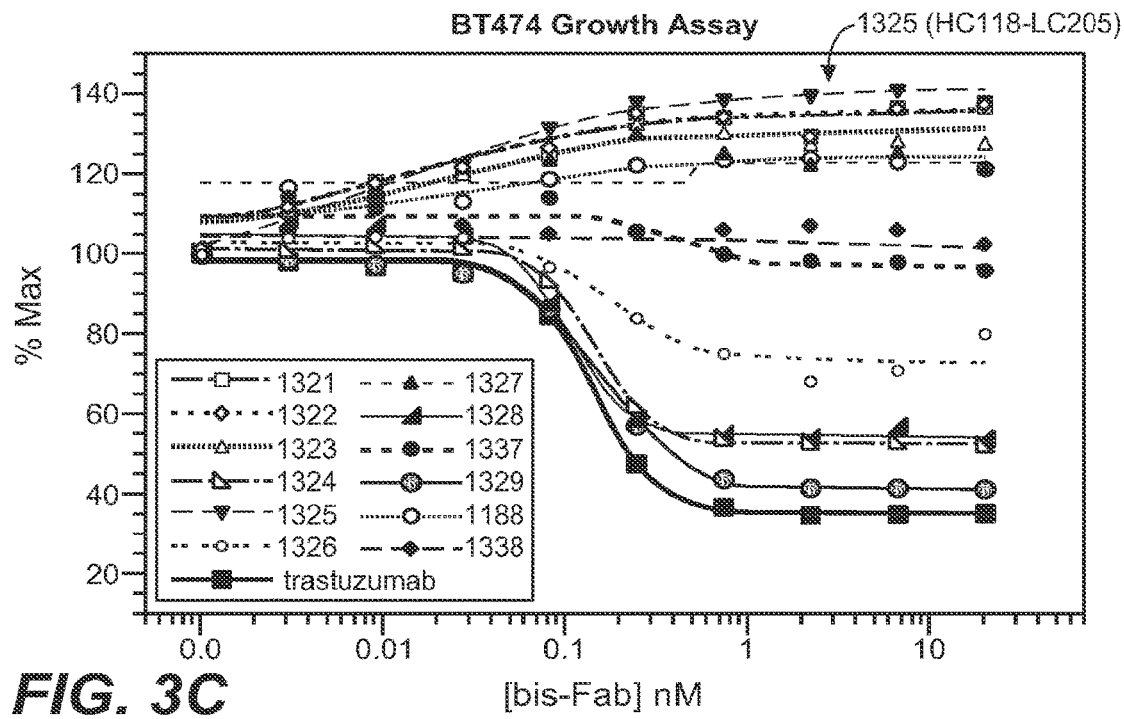
FIG. 3 shows the production and characterization of trastuzumab-derived bis-Fab structural variants as described in Example 3. (A) Schematic representation of four trastuzumab-derived Fabs showing the thio-attachment points (upper portion) and table indicating the unique identifier for each bis-Fab and the source of each thio-Fab (lower portion); (B) non-reducing SDS-PAGE of the bis-Fabs; (C) effect of bis-Fabs at varying concentrations on BT474 cell growth; (D) effect of bis-Fab 1325 (upward slanted striped bars) in comparison to the parent antibody Herceptin® (trastuzumab) (open bars) on BT474 cell growth over time. Downward slanted striped bars, no treatment.
Figure 3D:
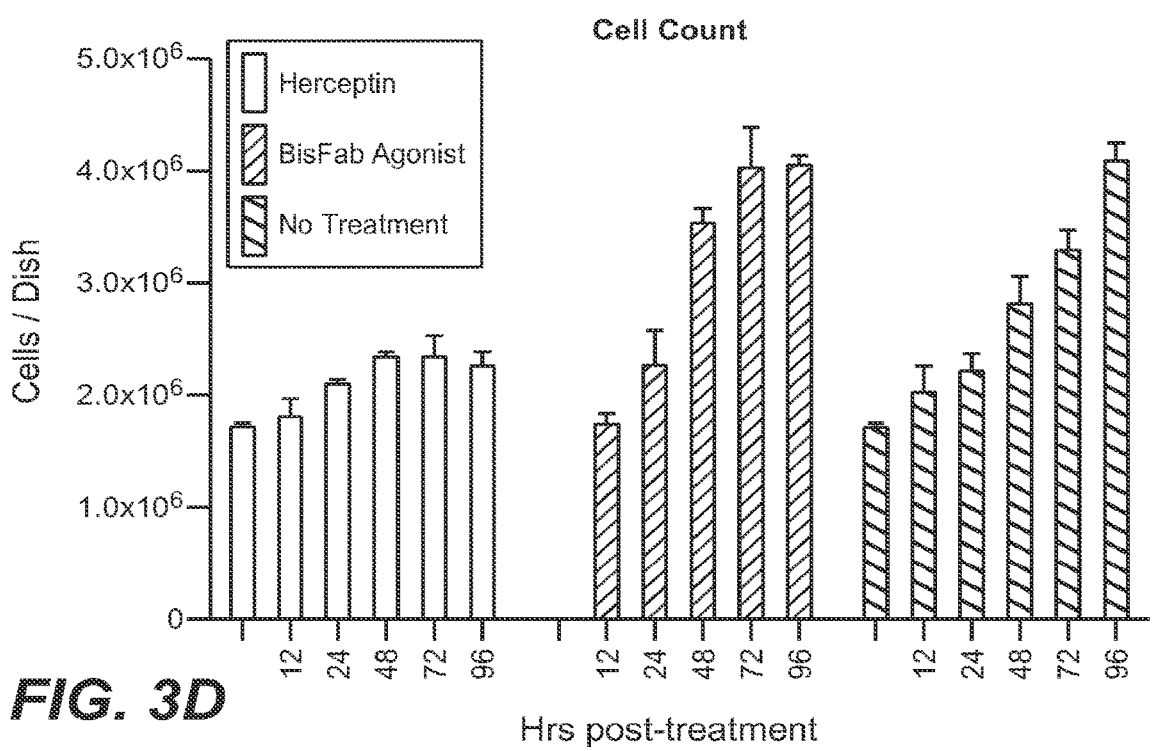

Next, we tested each of the bis-Fab structural variants for their effect on BT474 cell proliferation in comparison to trastuzumab. FIG. 3C shows the effect of each of the bis-Fabs and the parent antibody, trastuzumab, tested at varying concentrations (indicated on the horizontal axis) on the growth of BT474 cells. Viable cells were determined by Alamar blue staining and reported as a percentage of the maximum normalized to untreated controls (% Max on the vertical axis). As shown in FIG. 3C, the trastuzumab bis-Fab structural variants exhibited a wide range of activities that spanned from antagonists displaying activity similar to the parent antibody (bis-Fabs 1324, 1328, and 1329) to very potent agonists (bis-Fabs 1321, 1322, 1323, and 1325). Interestingly, four of these agonist bis-Fabs were more potent agonists than the original agonist identified, bis-Fab 1188 (FIG. 3C). In this assay, the most potent agonist was the bis-Fab 1325, which is the combination of HercHC$^{118Cys}$ and HercLC$^{205Cys}$. Finally, a time course experiment was performed testing the effect of bis-Fab 1325 compared to Herceptin® (trastuzumab) on BT474 cell growth. As shown in FIG. 3D, Herceptin® (trastuzumab) (open bars) inhibited cell growth throughout the course of the experiment, while bis-Fab 1325 (upward slanted striped bars) promoted cell growth, consisting with the cell growth assay described above. The downward slanted striped bars show the control cells that received no treatment.

Figure 4:
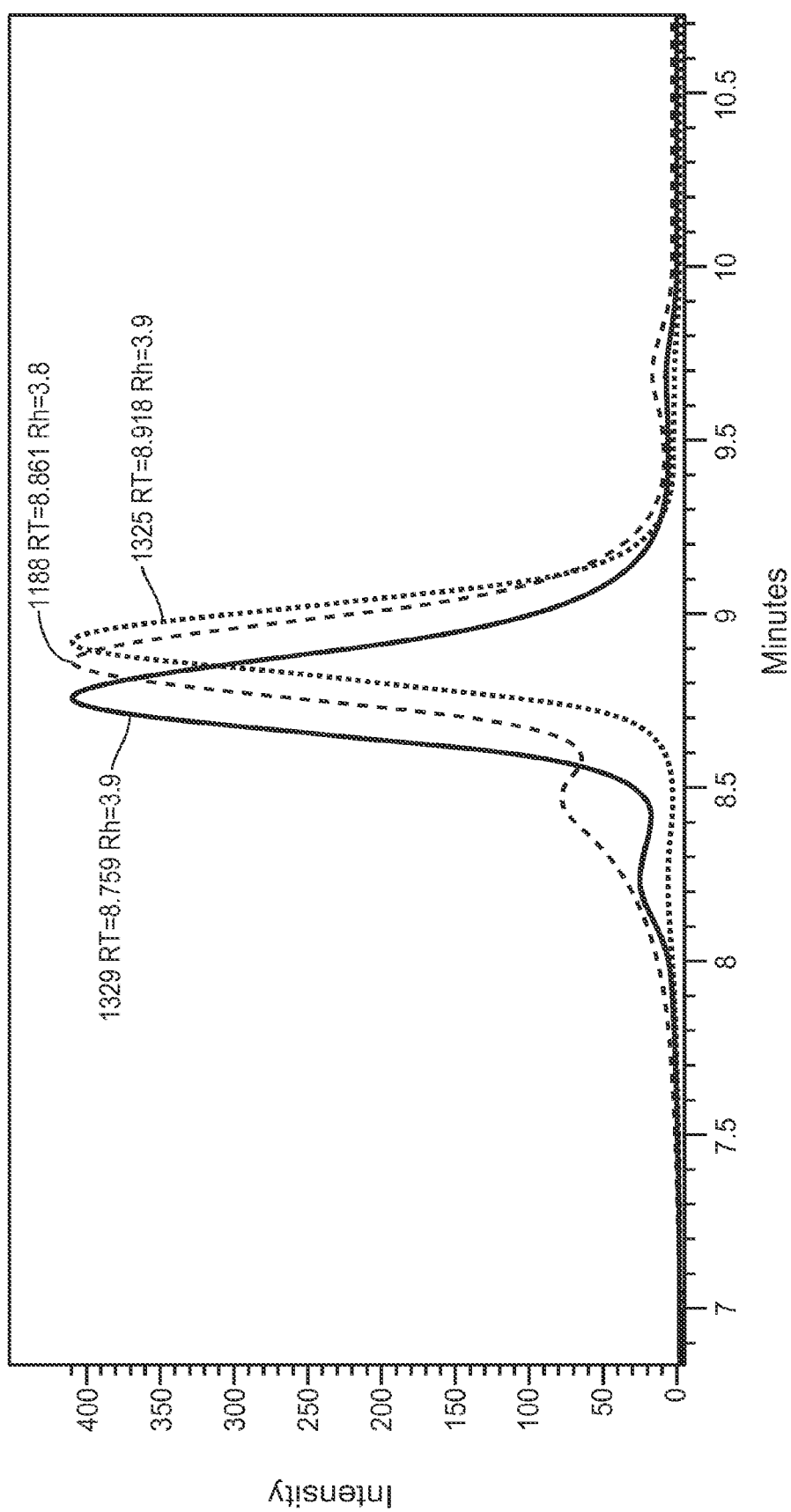
FIG. 4 shows a gel-filtration analysis of the indicated bis-Fabs as described in Example 3. The relative retention times (horizontal axis) (RT) and hydrodynamic radius (Rh) are indicated.

We considered the various linkage combinations of the bis-Fabs in connection with certain physical attributes of the molecules. As shown in FIG. 3B, SDS-PAGE analysis revealed differences in apparent molecular weight between the different bis-Fabs. This, however, was not a reliable predictor of the BT474 cell proliferation activity of the bis-Fab. Most notably, the most potent agonist in the BT474 assay, HercHC$^{118Cys}$-HercLC$^{205Cys}$, showed an apparent molecular weight very close to the apparent molecular of the potent antagonists. In addition to the observed migration differences on SDS-PAGE, which is likely due to the location of linkage sites, we analyzed other physical properties. We tested for internalization, affinity to the target receptor by Scatchard analysis, SEC-MALS elution and molecular weight and hydrodynamic radius. The results of the analysis of the cell-surface dissociation constant (Kd) and sites per cell for the indicated molecules are shown in Table 2 below. No significant difference was observed between agonist and antagonist molecules. FIG. 4 provides a gel-filtration analysis on Shodex SEC showing the relative retention times (indicated on the horizontal axis) (RT) and hydrodynamic radius (Rh) of the indicated molecules. Again, no significant difference was observed between agonist and antagonist molecules. Accordingly, these experiments did not reveal any significant differences in these physical properties between agonist and antagonist molecules, only migration differences on SDS-PAGE (FIG. 3B) and a slight shift in retention on SEC (FIG. 4).

TABLE 2

Antagonist and agonist cell-surface Kd and sites per cell.

| Molecule | Kd 1 (nM) | Kd 2 (nM) | Ave. (nM) | Sites per cell | Cell line |
|---|---|---|---|---|---|
| Bis-Fab 1188 (agonist) | 3.2 | 3.3 | 3.3 | 1.70 × 10$^6$ | Calu3 |
| Herceptin (trastuzumab) (antagonist) | 3.6 | 3.8 | 3.7 | 1.50 × 10$^6$ | Calu3 |
| Herceptin-Fab (trastuzumab-Fab) (antagonist) | 7.3 | 9.2 | 8.3 | 2.10 × 10$^6$ | Calu3 |
| Bis-Fab 1325 (agonist) | 3.9 | 4.0 | 4.0 | 0.98 × 10$^6$ | BT474 |
| Herceptin (trastuzumab) (antagonist) | 4.4 | 4.5 | 4.5 | 0.86 × 10$^6$ | BT474 |

We next analyzed the Her signaling pathway, specifically by examining receptor activation in BT474 cells after agonist treatment. In Her2 overexpressing cells lines such as BT474, Herceptin® (trastuzumab) inhibits ligand-independent interactions between Her2 and Her3 which accounts for the antiproliferative effects of the antibody in cell culture (Junttila, T. T., et al. *Cancer Cell* 15(5):429-40 (2009)). The disruption of Her2/Her3 interactions by Herceptin® (trastuzumab) results in the loss of phosphorylation of Her3 and a decrease in activity of the serine/threonine kinase, AKT. Id.

Figure 5A:
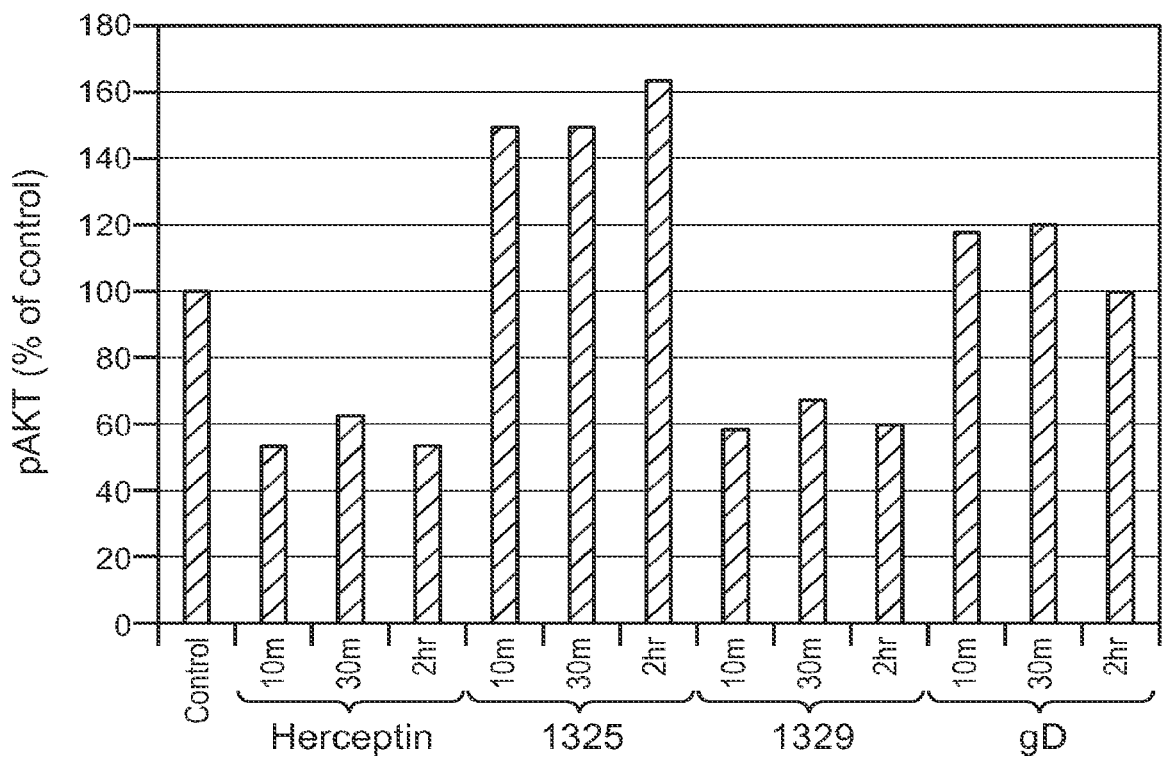
FIG. 5 shows the results of the analysis of the signaling pathway for Her2 bis-Fabs and Herceptin® (trastuzumab) in BT474 cells as described in Example 3. (A) ELISA analysis of AKT phosphorylation in response to treatment with Herceptin® (trastuzumab), the agonist bis-Fab 1325, the antagonist bis-Fab 1329, or gD; (B) Western blot analysis probing the phosphorylation state of certain Her signaling pathway enzymes (HER3, AKT, and MAPK) in BT474 cells treated with Herceptin® (trastuzumab), the agonist bis-Fab 1325, the antagonist bis-Fab 1329, or gD (pHER3, pAKT, pMAPK: phospho-specific antibodies; HER3, AKT, MAPK: non-phospho-specific antibodies; tubulin: control); (C) Table of phosphorylated peptides derived from trypsin cleavage of Her2. The phosphorylated residues of interest in each peptide are indicated by small cap letters in bold italicized type in the peptide sequence. The table also provides mass spectrometry analysis of total phosphorylation of phosphopeptide sites in Her2 after no treatment (basal), treatment with Herceptin® (trastuzumab), treatment with the agonist bis-Fab 1325 (Bis-Fab), or treatment with 10 nM Heregulin as quantitated by absolute quantitation (AQUA) or by label-free quantitation. The data represent the mean of three independent biological and technical replications and include the standard deviation (SD); (D) Table listing the synthetic peptides containing heavy atoms used for AQUA (AQUA peptides); "+13C:" the number of heavy carbon atoms in the AQUA peptide; "+15N:" the number of heavy nitrogen atoms in the AQUA peptide; "add mass:" the total mass increase of the AQUA peptide over the mass of the natural peptide; "heavy monoisotopic MH+:" total mass of the heavy peptide in the singly charged state; residues in the AQUA peptide that contain heavy atoms are indicated by large cap, bold, italicized, underlined letters; phosphorylation sites in the AQUA peptide are indicated by small cap, bold, italicized letters; (E) Pairwisc comparison of the three treatment groups bis-Fab 1325 (BF agonist, top graph), trastuzumab (Herc, middle graph) and Heregulin (Hrg, bottom graph), each compared to no treatment. Phosphorylation sites are indicated along the horizontal axis of the bottom graph; differences in mean percent phosphorylation are indicated along the vertical axis of each graph.
Figure 5B:
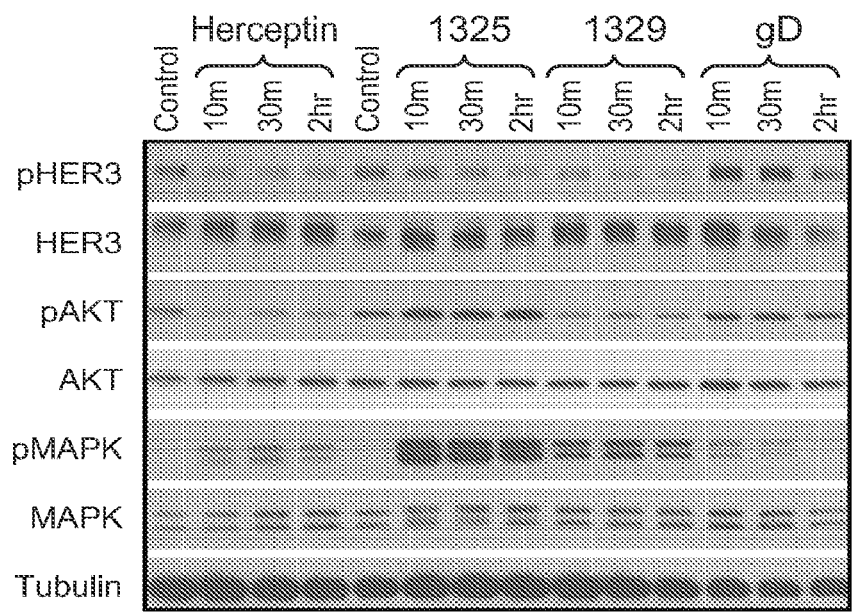

We compared the effects of the agonist bis-Fab 1325, the antagonist bis-Fab 1329, the parent antibody, Herceptin® (trastuzumab), and a control antibody lacking phosphorylation action, gD, on phosphorylation of AKT and Her3. BT474 cells were treated with each of these molecules. Cells were harvested at 10 minutes, 30 minutes, and two hours after treatment was initiated. Cell lysates were measured for AKT phosphorylation by ELISA with anti-phospho AKT antibodies. The results are shown in FIG. 5A. The antagonists Herceptin® (trastuzumab) and bis-Fab 1329 decreased the amount of phosphorylated AKT, as measured by ELISA, while the agonist bis-Fab 1325 increased the amount of phosphorylated AKT (FIG. 5A). The inhibitory activity of the antibody and bis-Fab 1329 was observed at ten minutes and continued to increase slightly for up to two hours. The bis-Fab antagonist 1329 was slightly less potent than the parent antibody in the first thirty minutes of the experiment but reached the same level of inhibition by 2 hrs. (FIG. 5A). The agonist bis-Fab 1325, however, resulted in an increase in the level of phospho-AKT after ten minutes and the level of phosphor-AKT continued to rise slightly during two hours of treatment (FIG. 5A). An antibody effect is seen with gD where phospho-AKT levels rise slightly after treatment. The effect, however, is within the range of untreated variability. Western blot analysis using phospho-AKT antibodies also showed that the level of phospho-AKT increased in response to the agonist bis-Fab 1325 (FIG. 5B, compare pAKT row to AKT row).

We also examined levels of Her3 phosphorylation because Herceptin® (trastuzumab) treatment is known to reduce the levels of phosphorylated Her3 (*Cancer Cell* 15(5):429-40 [2009]). For these experiments, BT474 cells were treated with Herceptin® (trastuzumab), bis-Fab 1325, bis-Fab 1329, or gD in 96-well plates for up to two hours. At the times indicated (10 minutes, 30 minutes, or 2 hours) cells were solubilized. Western blot analysis of the cell lysates was carried out as follows. Cell lysates were separated by SDS-PAGE and transferred to nitrocellulose membranes. The nitrocellulose membranes were probed with the indicated phospho-specific (pHER3, pAKT, or pMAPK) or non-phospho-specific antibodies (HER3, AKT, or MAPK) to assess the activation state of the indicated Her signaling pathway enzymes. An anti-tubulin antibody was used as a control. As shown in FIG. 5B, western blot analysis using anti-Her3 phosphotyrosine antibodies showed a characteristic and expected decrease in phospho-Her3 in response to the antagonists Herceptin® (trastuzumab) and bis-Fab 1329 that occurred over two hours (FIG. 5B, compare pHER3 row to HER3 row). The treatment of cells with the gD antibody had no effect on the level of Her3 phosphorylation (FIG. 5B, compare pHER3 row to HER3 row. Surprisingly, we did not observe an anticipated increase in phospho-Her3 by treatment with the agonist bis-Fab 1325 (FIG. 5B, compare pHER3 row to HER3 row). In fact, there was a slight decrease in the amount of phospho-Her3 over the two hour time period, similar to what was observed with the antagonists (FIG. 5B). The observed phosphorylation of MAPK in response to treatment with bis-Fab 1325 (FIG. 5B, compare pMAPK row to MAPK row) indicates that the agonist may be activating a pathway generally associated with ligand-induced activation. This surprising result raises questions about the mechanisms through which the Her2 bis-Fab agonists are acting.

Figure 5E:
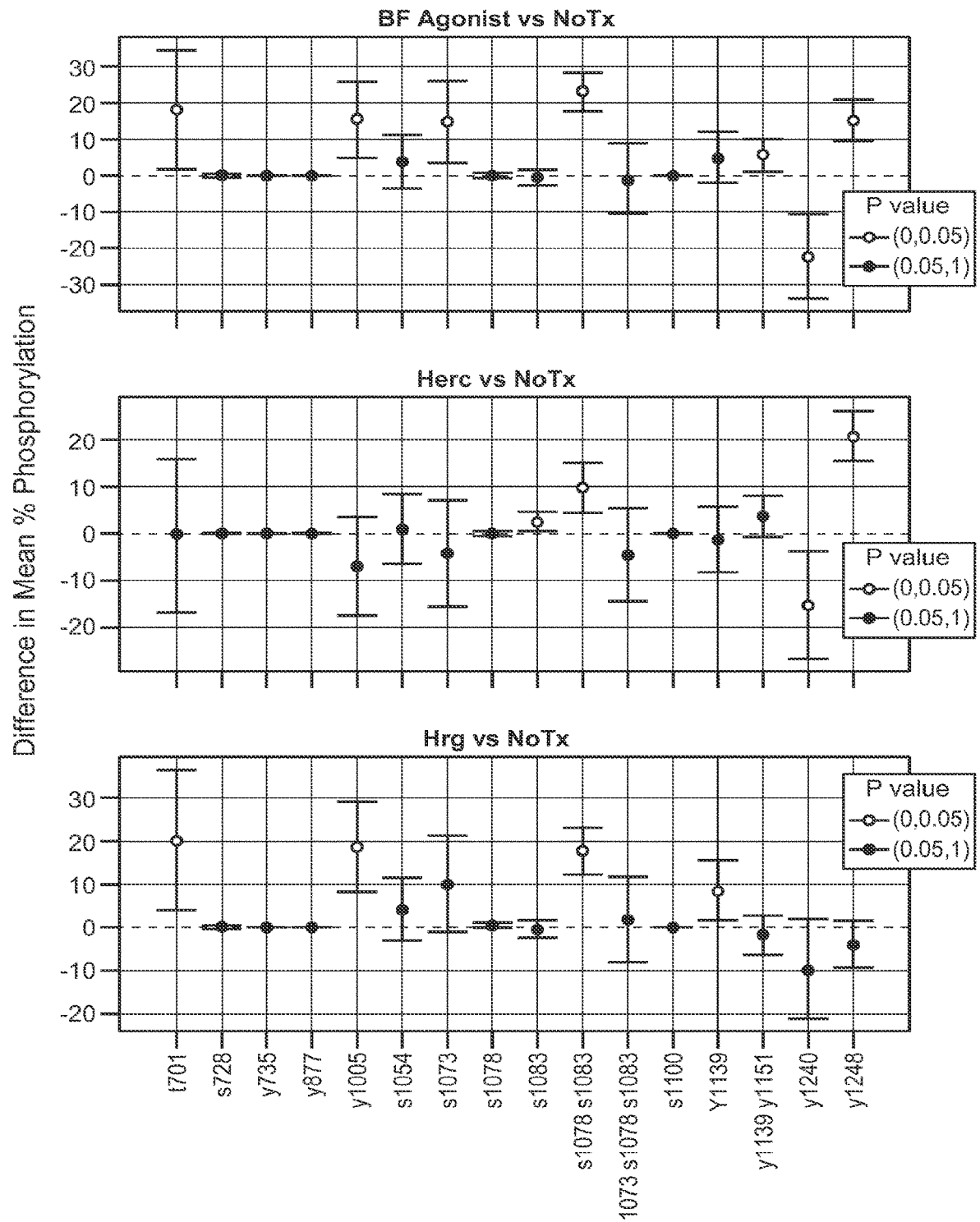

Therefore, we next investigated whether there is a direct impact on phosphorylation of Her2 when cells are treated with the agonist bis-Fab 1325. It has been shown previously that Herceptin® (trastuzumab) treatment does not significantly alter the phosphorylation state of Her2. Kito, K. et al., *Curr Genomics* 9(4):263-74 (2008). Because Her2 is highly phosphorylated in the basal state (see Id.), we used quantitative mass spectrometry to probe phosphorylation site changes in Her2 in response to the different molecules. Using phospho-mapping techniques we determined that a number of sites were phosphorylated to different levels in Her2 in untreated BT474 cells (FIG. 5C, basal column). The table in FIG. 5C provides a list of the phosphorylated peptides derived from trypsin cleavage of Her2. The amino acid in each peptide sequence denoted with a small cap bold italicized letter indicates the phosphorylated residue of interest. The quantitative measurement of these sites showed that after treatment with Herceptin® (trastuzumab), there were few changes in the level of phosphorylation of the phosphopeptides compared to untreated cells (FIGS. 5C and 5E). But treatment with the agonist bis-Fab 1325 showed several phosphorylation sites that increased in amount of phosphorylation compared to untreated cells (FIGS. 5C and 5E). Some of the phosphorylation sites also increased in the level of phosphorylation following treatment with Heregulin, a known PI3K pathway agonist (FIGS. 5C and 5E). We also performed a statistical test. For each peptide, a mixed effects model was fitted to the relative phosphorylation level, with treatment as a fixed effect and sample as a random effect. As shown in FIG. 5E, pairwise comparisons of groups were carried out using Tukey-Kramer's method to adjust for multiple comparisons. This controls the overall false positive rate associated with performing multiple statistical tests for each peptide. In summary, these results reveal possible ligand-independent and Her3-independent activation of cell signaling pathways leading to proliferation. In addition, such results could lead to the identification of additional signaling components that are involved in cell proliferation thus leading to new therapeutic targets for cell proliferative disorders such as, but not limited to, cancer.

Example 4

Synthesis of and Characterization of Bis-Fabs Targeting FcγRIIb and FcεRI

To test the general applicability of the bis-Fab synthesis approach to other molecular targets, we designed a bispecific bis-Fab matrix using thio-Fabs or a hinge-cys-Fab derived from one antibody (5A6) that targets FcγRIIb and thio-Fabs or a hinge-cys-Fab derived from one antibody that targets FcεRIα (22E7). The 5A6 and 22E7 antibodies are described in U.S. Patent Pub. No. 20060073142 and Jackman, et al., *J. Biol. Chem.* 285:20850-20859 (2010). The FcγRIIb cell-surface protein is a protein tyrosine phosphatase that can dephosphorylate nearby tyrosine kinase receptors such as FcεRIα to inhibit their activity. We have previously described a bispecific IgG that targets these two receptors on the surface of mast cells (Id.). In addition, we showed that the bispecific antibody bound to and crosslinked FcεRIα and FcγRIIb forming a heterodimeric receptor complex, which potently inhibited the cellular signaling and histamine release initiated by IgE binding to FcεRIα. Id. Based on that mechanism of action of the bispecific IgG, we postulate that a bis-Fab targeting FcγRIIb and FcεRIα on the surface of mast cells would have an analogous mechanism of action. Thus, without being bound by theory, we hypothesize that treatment with a bis-Fab targeting FcγRIIb and FcεRIα will lead to recruitment of FcγRIIb into the activated receptor complex and result in inhibition of histamine release.

To synthesize bis-Fabs targeting FcγRIIb and FcεRIα, we generated thio-Fabs from each of the parent antibodies having cys substitutions at position 110 in the light chain and position 121 in the heavy chain. We also generated hinge-cys-Fabs from each of the parent antibodies having only one cys in the hinge region. These hinge-cys-Fabs were prepared using recombinant DNA methods, i.e., by subcloning a DNA fragment of the parent antibody Fab and expressing it in *E. coli*, followed by purification. All recombinant DNA methods and protein purification methods were standard procedures well known to those skilled in the art and described generally above. Table 3 below shows the bis-Fab synthesis matrix indicating the thio attachment points and providing the unique identifying number for each bis-Fab (in parentheses).

TABLE 3

Bis-Fab Synthesis Matrix.

| Step 2 (react with bis-Mal-thio-Fabs from Step 1) | Step 1 (+bis-maleimido crosslinker to form bis-Mal-thio-Fab) | | |
|---|---|---|---|
| | FcγRIIb$^{110C}$ | FcγRIIb$^{121C}$ | FcγRIIb$^{Hg\text{-}Cys}$ |
| FcεRIα$^{110C}$ | FcγRIIb$^{110C}$/FcεRIα$^{110C}$ (1307) | FcγRIIb$^{121C}$/FcεRIα$^{110C}$ (1301) | FcγRIIb$^{Hg\text{-}Cys}$/FcεRIα$^{110C}$ (1304) |

TABLE 3-continued

Bis-Fab Synthesis Matrix.

| Step 2 (react with bis-Mal-thio-Fabs from Step 1) | Step 1 (+bis-maleimido crosslinker to form bis-Mal-thio-Fab) | | |
|---|---|---|---|
| | FcγRIIb$^{110C}$ | FcγRIIb$^{121C}$ | FcγRIIb$^{Hg\text{-}Cys}$ |
| FcεRIα$^{121C}$ | FcγRIIb$^{110C}$/FcεRIα$^{121C}$ (1305) | FcγRIIb$^{121C}$/FcεRIα$^{121C}$ (1299) | FcγRIIb$^{Hg\text{-}Cys}$/FcεRIα$^{121C}$ (1302) |
| FcεRIα$^{Hg\text{-}Cys}$ | FcγRIIb$^{110C}$/FcεRIα$^{Hg\text{-}Cys}$ (1306) | FcγRIIb$^{121C}$/FcεRIα$^{Hg\text{-}Cys}$ (1300) | FcγRIIb$^{Hg\text{-}Cys}$/FcεRIα$^{Hg\text{-}Cys}$ (1303) |

Figure 6A:
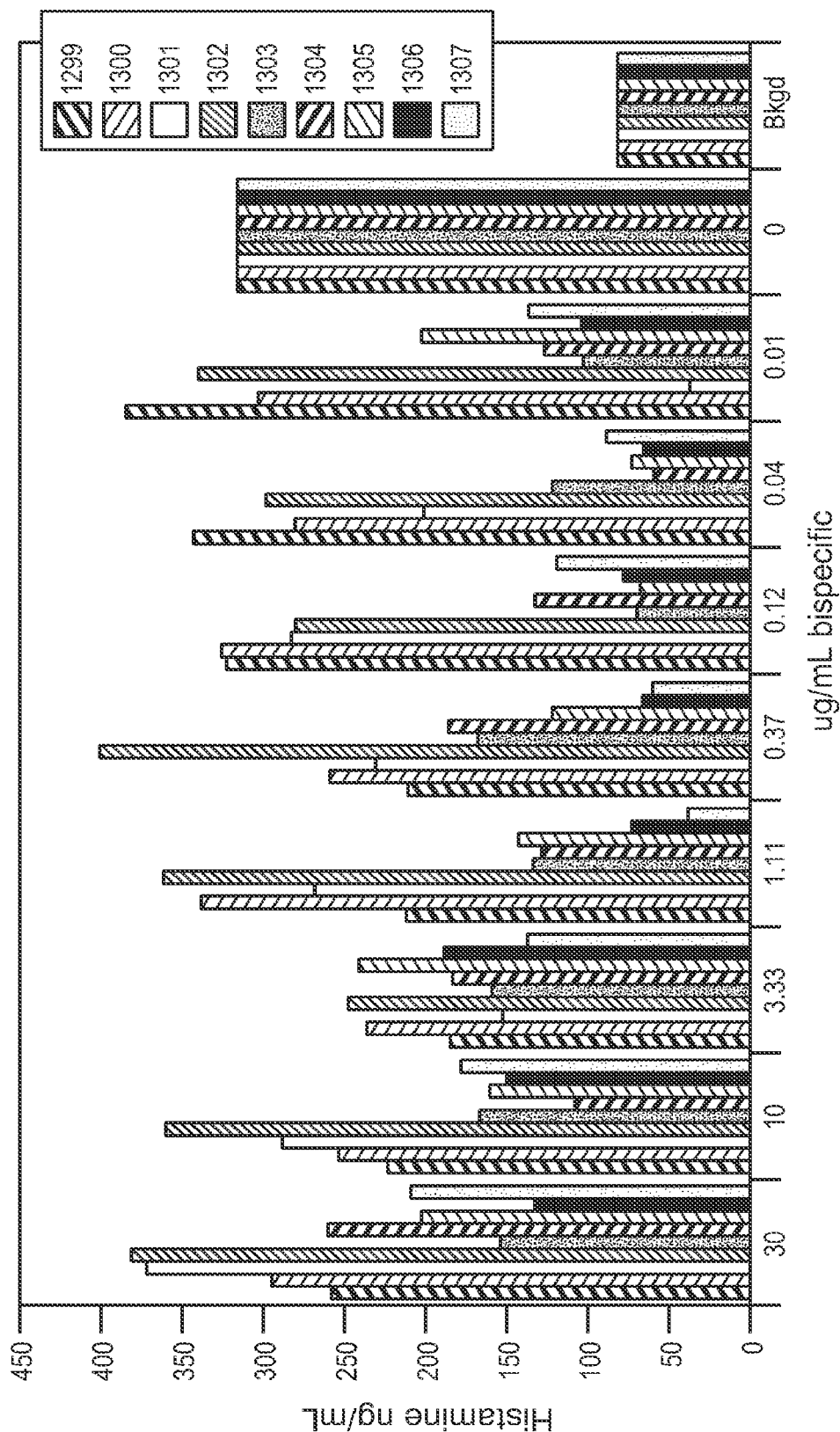
FIGS. 6A and 6B show the effect of increasing concentrations of the indicated bis-Fabs on histamine release from RBL cells expressing both FcεRIα and FcγRIIb as measured by ELISA as described in Example 4.
Figure 6B:
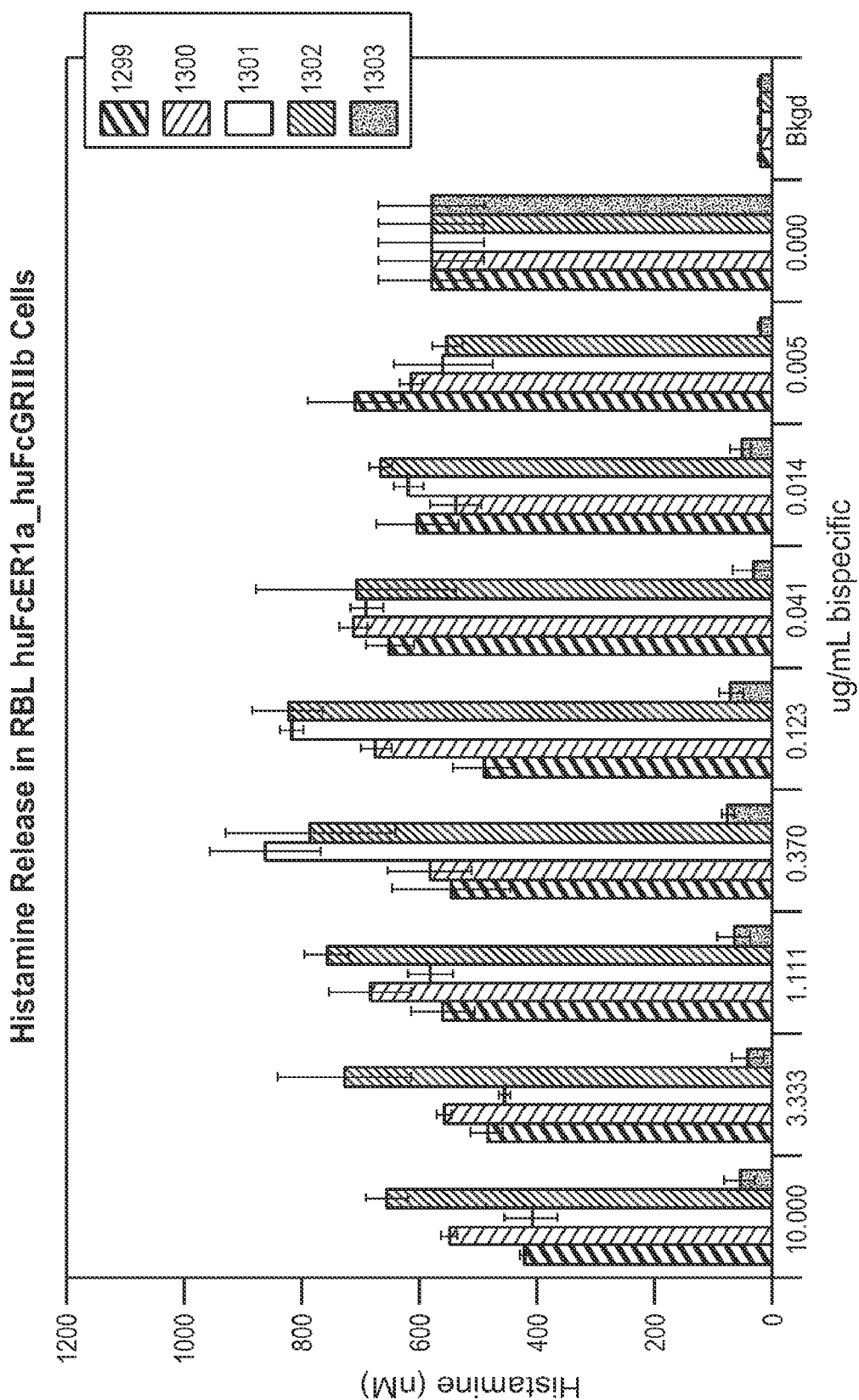

We previously described the generation of RBL cell line variants expressing both FcεRIα and FcγRIIb (Jackman, et al., *J. Biol. Chem.* 285:20850-20859 (2010)). We tested the effect of each of the bis-Fabs listed in Table 3 on histamine release from RBL cells expressing both FcεRIα and FcγRIIb. Cells were treated with increasing concentrations of each of the bis-Fabs and histamine release was measured by ELISA. The results are shown in FIGS. 6A-B. As can be seen, the different bis-Fabs displayed a range of activities. For several of the potent antagonists, the highest activity level of inhibition was seen at concentrations of 370-110 ng/mL. This is presumably the concentration at which the maximum number of inhibitory complexes are formed. At higher concentrations, one arm of the bis-Fab may bind to its receptor where the other arm may not bind the other receptor of the inhibitory complex. This would be analogous to the bell shaped activity curves that some dimeric hormones have when receptor dimerization is required to generate intracellular signals (eg. VEGF and its receptor). In addition, several of the molecules did not show any inhibitory activity while one molecule showed extraordinary inhibition. These results are shown in FIG. 6B. The four molecules that did not display potent inhibition (1299, 1300, 1301, 1302) contain at least one heavy chain 121Cys linkage. The most potent inhibitory molecule, 1303, is linked to both thio-fabs through the hinge-cys.

Example 5

Modified Bis-Fabs and in Vivo Activity

One feature of the bis-Fabs described above is an expected short half-life in vivo due, at least in part, to the lack of an Fc region in the molecule. For certain in vivo applications, it would be desirable for bis-Fabs to possess pharmacokinetic properties similar to native antibodies. Accordingly, we have designed a method for producing modified crosslinkers for use in the synthesis of bis-Fabs. The use of such modified crosslinkers, as described in detail below, allows for the addition of reagents useful for modifying in vivo half-life, such as, but not limited to, polyethylene glycol (PEG). In addition, modified crosslinkers as described herein allow for the addition of reagents useful as imaging or detection agents, such as, but not limited to, fluorescent tags, or cytotoxic agents, such as, but not limited to, monomethyl auristatin E (MMAE), or reagents possessing other desirable properties or functions, such as, but not limited to, siRNA.

Synthesis of Modified Crosslinker and Modified Bis-Fabs

We designed a process to synthesize a modified crosslinker that would allow for the attachment of any sulfhydryl-reactive moiety. Below, we describe a process for attaching N-succinimidyl-S-acetylthioacetate (SATA) to bis-maleimide to form bis-maleimido-acetylthioacetate (BMata) having a protected SH group which can be used in further reactions for the attachment of desired functional groups.

Figure 7A:
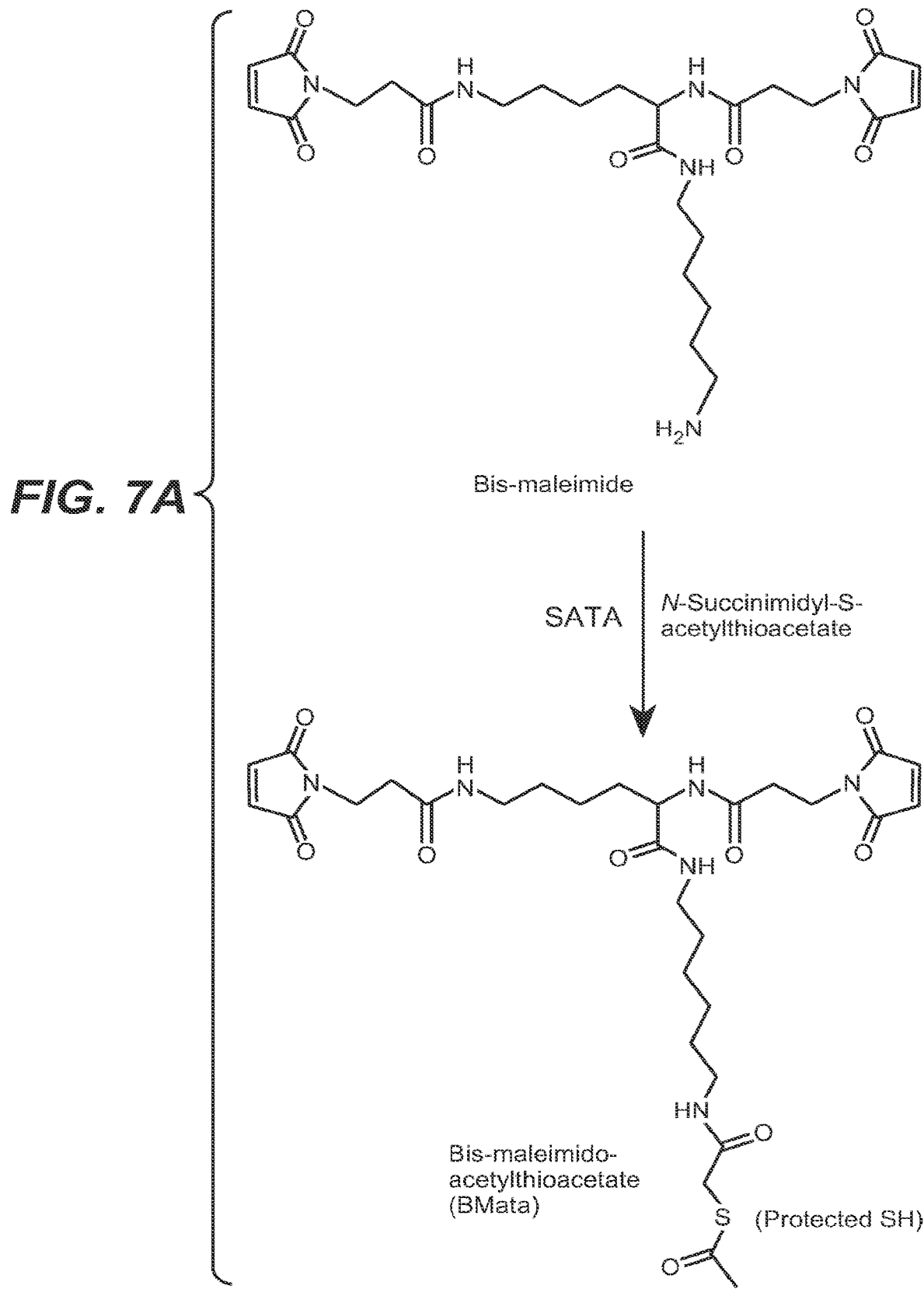
FIG. 7 shows the synthesis of the modified crosslinker, BMata (A) and the general scheme for the synthesis of a pegylated bis-Fab (B) as described in Example 5.

We started with bis-maleimide amine (MW 546.62) obtained from Quanta BioDesign Limited, Powell, Ohio. Sixty micromoles (32 mg) was dissolved in 100 μL dimethylamine (DMA) and diluted with 1 ml acetonitrile. One hundred thirty micromoles (31 mg) SATA (N-Succinimidyl-S-acetylthioacetate, MW 231.23, Thermo Fisher Scientific) was dissolved in 1 ml acetonitrile and added to the bis-maleimide solution. Hepes buffer (potassium salt, pH 7.1, 0.5 M) was added to a final concentration of 0.15 M and the reaction mixture was incubated overnight in the dark at 4° C. The mixture was diluted 4-fold with 0.1% trifluoroacetic acid (TFA) before separation on a 10×250 mm C4 column (Vydac) with an acetonitrile gradient of 15-50% in 0.1% TFA). Fractions containing bis-maleimido-acetylthioacetate (MW 662.29), as assessed by electrospray mass spectrometry (Agilent 6210 TOF), were pooled, dried under vacuum centrifugation and stored at −20° C. The reaction to synthesize this modified crosslinker, BMata, is shown in FIG. 7A.

One reagent that can be attached to BMata is PEG, which we investigated for its effects on the half-life of modified bis-Fabs in vivo. We followed the following procedure to generate a bis-Fab containing BMata for subsequent reaction with PEG.

One lot of bis-Fab targeting EGFR (Her1) (C3-101 thio-Fab$^{V110C}$) and Her2 (trastuzumab (Here) thio-Fab$^{V110C}$) was produced with the BMata crosslinker. About 500 mgs of modified bis-Fab was synthesized using 500 mgs of each thio-Fab as starting material. The thio-Fabs were expressed in *E. coli* and purified as described above. The bis-Fab was synthesized by first chemically reacting BMata with trastuzumab thio-Fab$^{V110C}$. The complex was isolated by gel filtration and reacted with C3-101 thio-Fab$^{V110C}$ to produce the crosslinked bispecific polypeptide. The final complex was isolated again by gel filtration and characterized by mass spectrometry and SDS-PAGE as described above.

Figure 7B:
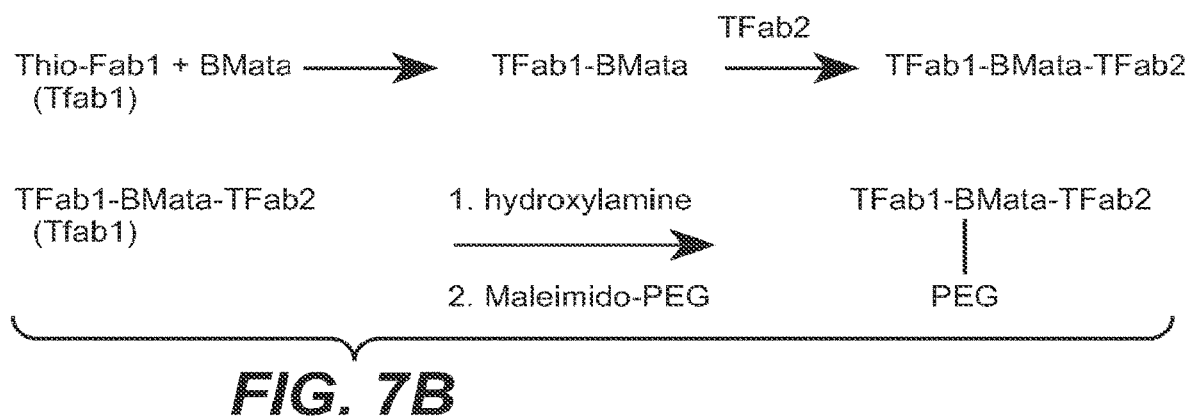

Because of the masked-thiol in Bmata (FIG. 7A), the bis-Fab produced using this crosslinker is amenable to PEGylation with maleimido containing polymers after deprotection of the blocking group with hydroxlamine. To do this, the bis-Fab was first separated into several aliquots of about 50-60 mgs each. To each aliquot, one tenth the volume of 0.5 M hydroxylamine, 25 mM EDTA in phosphate buffered saline (PBS) at pH 7.2 was added. The deprotection proceeded at room temperature for about two hours. Removal of the protecting group by hydroxylamine resulted in the loss of 42 daltons which can be observed by a change in the mass of the bis-Fab by mass spectrometry (data not shown). After deprotection, a 1:1 molar equivalent of PEG-maleimido was added to the bis-Fab aliquots and allowed to react for 2-20 hours. This resulted in near complete conversion of the bis-Fab to a higher molecular weight species contain a single PEG (data not shown). The general reaction scheme is shown in FIG. 7B.

Figure 8A:
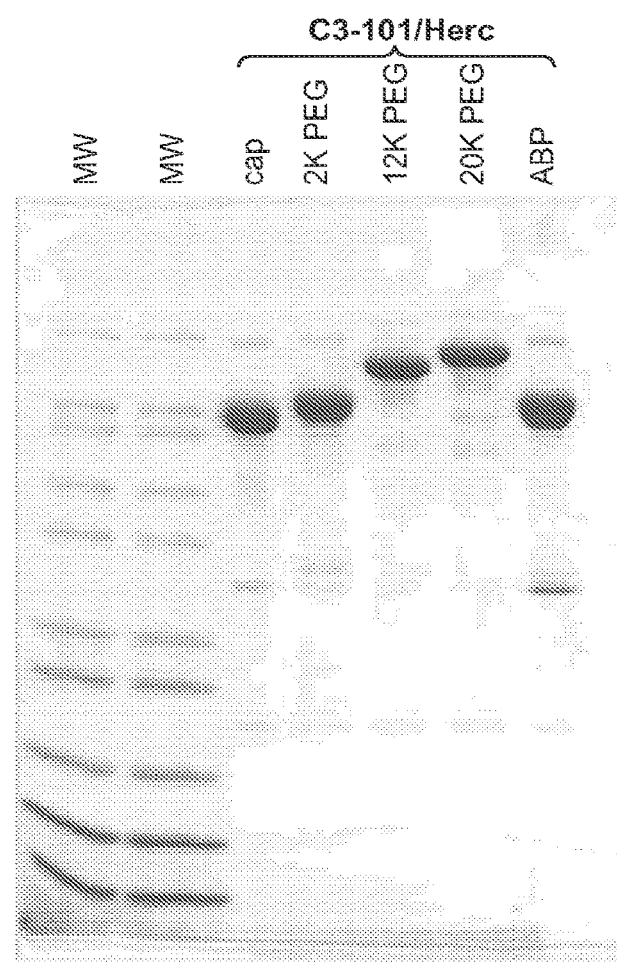
FIG. 8 shows SDS-PAGE analysis (A) and S-200 gel filtration analysis (B) of bis-Fab C3-101$^{V110C}$/Herc$^{V110C}$ modified to contain varying sizes of PEG or ABP as described in Example 5.

Starting with the BMata crosslinked bis-Fab C3-101$^{V110C}$/Herc$^{V110C}$, several different sizes of PEG polymers were used in the synthesis reaction described above to generate PEGylated bis-Fabs carrying PEG of varying molecular weight. The various PEG polymers were purchased as maleimido derivatives from NOF Corporation (Japan). After reaction with the PEG reagents, the PEGylated bis-Fabs were purified by S-200 gel filtration in 25 mM MES, pH 5.8, 300 mM NaCl, and 1 mM EDTA. FIG. 8A shows an SDS-PAGE analysis of the purified bis-Fabs. Five different reaction products are shown, left to right. Starting from the left is BMata bis-Fab reacted with an N-ethylmaleimide (NEM) cap, then BMata bis-Fab reacted with linear PEG chains of 2 kDa, 12 kDa and 20 kDa, respectively, and finally, BMata bis-Fab reacted with a maleimido-albumin-binding-peptide, ABP, mal-H, QRLMEDICLPRWGCL-WEDDF (SEQ ID NO: 24). Nguyen et. al, *Prot. Engineering, Design and Selection* 19:291-97 (2006). The bis-Fab-ABP was synthesized to investigate the ABP moiety as an alternative to PEG as a means to increase half-life of the bis-Fab by increasing binding to serum albumin. See Id.

Figure 8B:
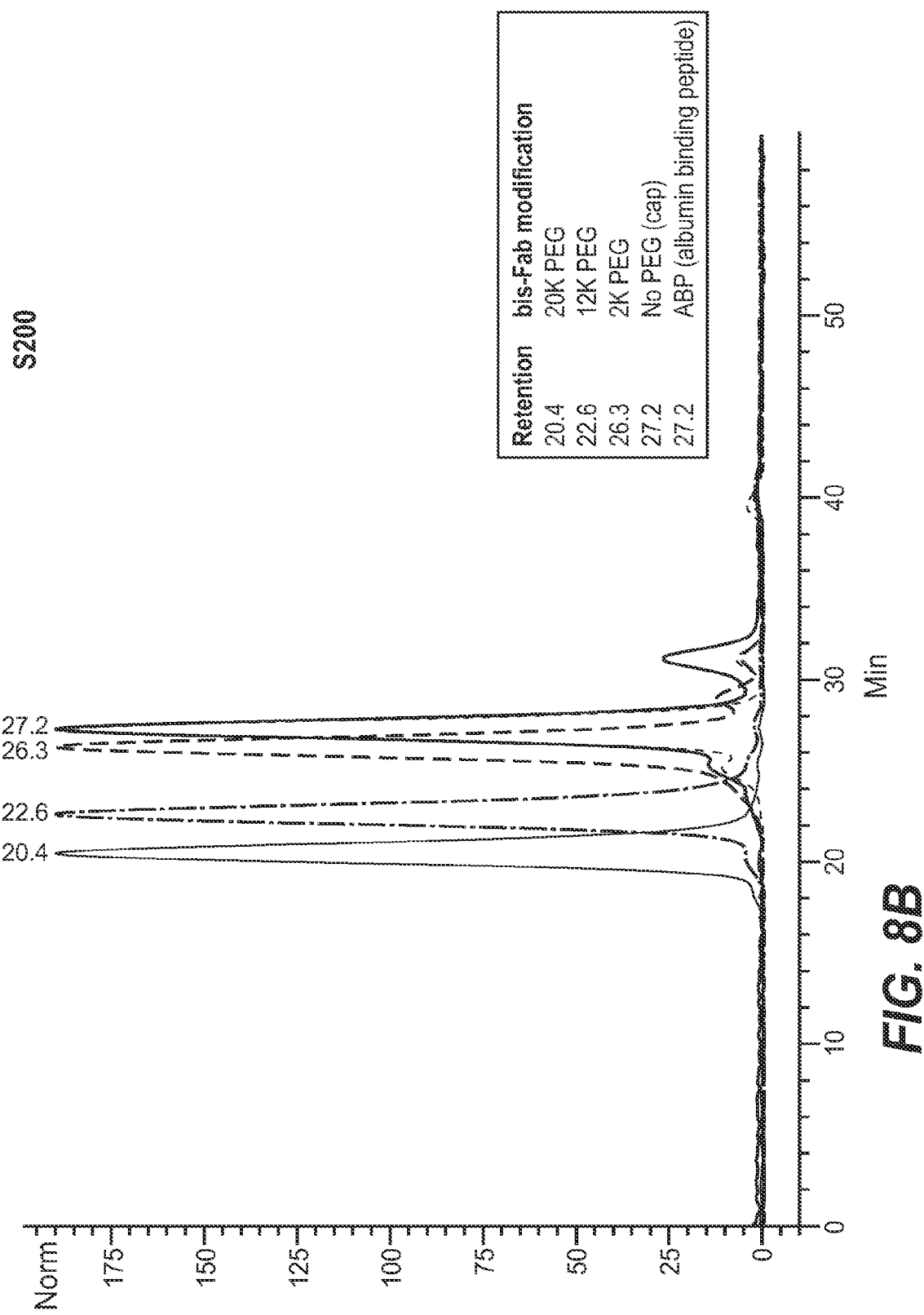

These five modified bis-Fabs were analyzed by gel filtration chromatography, and shown to have a greatly increased hydrodynamic radius. The 20 K PEG and the 12 K PEG containing bis-Fabs and the ABP containing bis-Fab were observed to elute on S-200 gel filtration significantly earlier than a typical human IgG (retention time 25.2 min) (FIG. 8B). We next investigated the pharmacokinetic parameters, including half-lives, of each of these five modified C3-101$^{V110C}$/Herc$^{V110C}$ bis-Fabs in both mice and nude rats. These experiments and results are described in detail below.

Bis-Fab Pharmacokinetics

Two separate experiments were performed to asses the effects of the BMata-PEG or BMata-ABP modifications described above on in vivo serum half-life of C3-101$^{V110C}$/Herc$^{V110C}$ bis-Fabs. A single 5 mg/kg IV bolus dose was administered to either mice or nude rats and bis-Fab present in the serum was analyzed for up to 14 days. Individual mice were used for each data point, whereas in the rats, serum samples were taken from the same animals over the course of the experiment.

An ELISA assay was developed to detect the intact bispecific bis-Fab in the mouse and rat serum. The details of the ELISA are as follows.

The concentration of bis-Fab in rodent serum was determined using an ELISA. Briefly, EGFR-Fc (Genentech Reagent) diluted to 1 µg/ml in PBS, was coated onto 384 well Maxisorb polystyerene plates (Nalgate Nunc International Cat#464718). After 16 to 72 hours, the coat was removed and the plates were blocked with block buffer (PBS/0.5% BSA/Proclin 300) for 0.5 to 3 hours. Dilutions of bis-Fab standard (0.156 to 20 ng/ml) were prepared in assay buffer (PBS/0.5% BSA/0.05% Tween 20/0.25% CHAPS/5 mM EDTA/0.2% BGG/0.35M NaCl/15 ppm Proclin 300). Samples (rat or mouse serum containing bis-Fab) were diluted to a minimum dilution of 1/100 into assay buffer, and then serially diluted 8 times into assay range. Blocked plates were washed 3 times with wash buffer (PBS/0.05% Tween 20) and standards and samples were added to appropriate assay wells. After a 1-hour incubation, plates were washed 6 times with wash buffer. The bound bis-Fab was detected using a biotinylated HER2ECD (Genentech Reagent Lot 39575-15-biotinylation was perform using NHS-Succimide chemistry (Biotin-X-NHS research organics 10554B-2)). After a 1-hour incubation, plates were washed 6 times with wash buffer and streptavidin linked horseradish peroxidase (GE Healthcare RPN1231) diluted 1/40,000 in conjugate buffer (PBS/0.5% BSA/0.05% Tween 20/15 ppm Proclin 300) was added to all assay wells. After a 30-minute incubation, plates were washed 6 times and the substrate TMB (KPL, Cat#50-65-02) was added to all assay wells. The substrate reaction was stopped after 15-20 minutes with 1M Phosphoric Acid. Plates were read at 450 nm using a reference wavelength of 620 nm. Sample concentrations were determined by comparing results to standards using a 4-parameter curve-fitting algorithm.

Figure 9A:
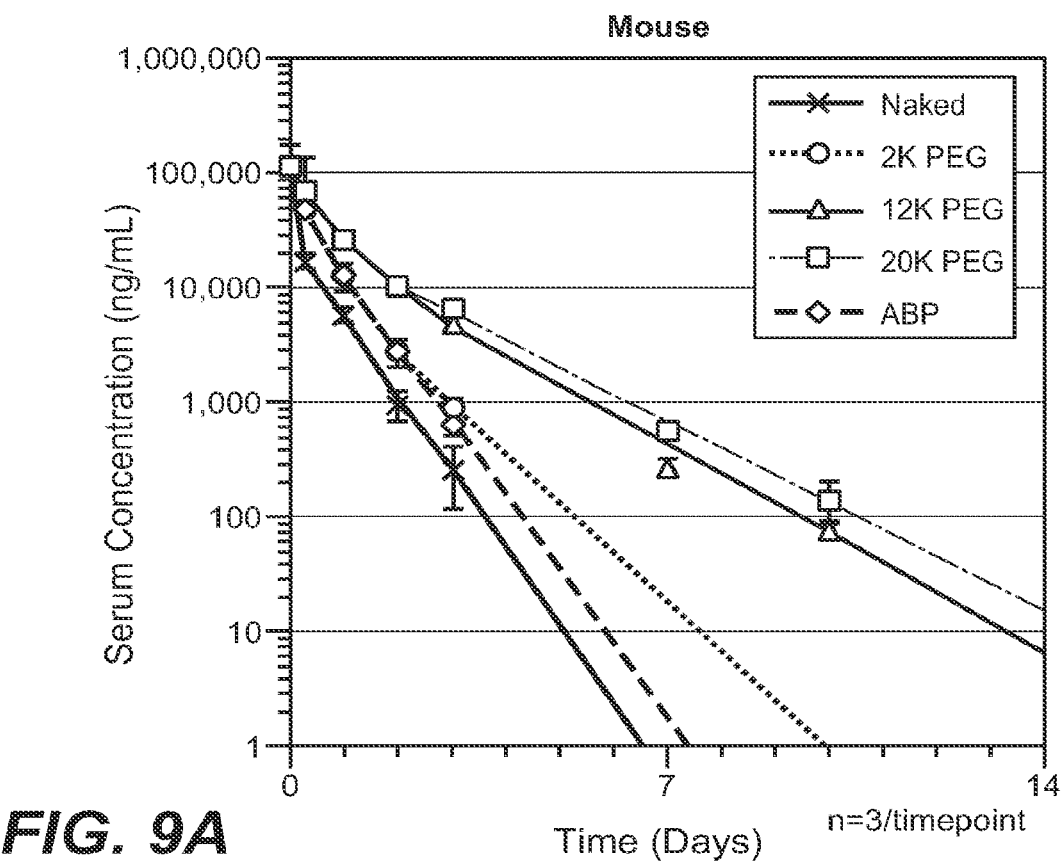
FIG. 9 shows pharmacokinetic analyses of bis-Fab C3-101$^{V110C}$/Herc$^{V110C}$ unmodified (naked) or modified to contain varying sizes of PEG or ABP following administration to mice (A) or nude rats (B) as described in Example 5.
Figure 9B:
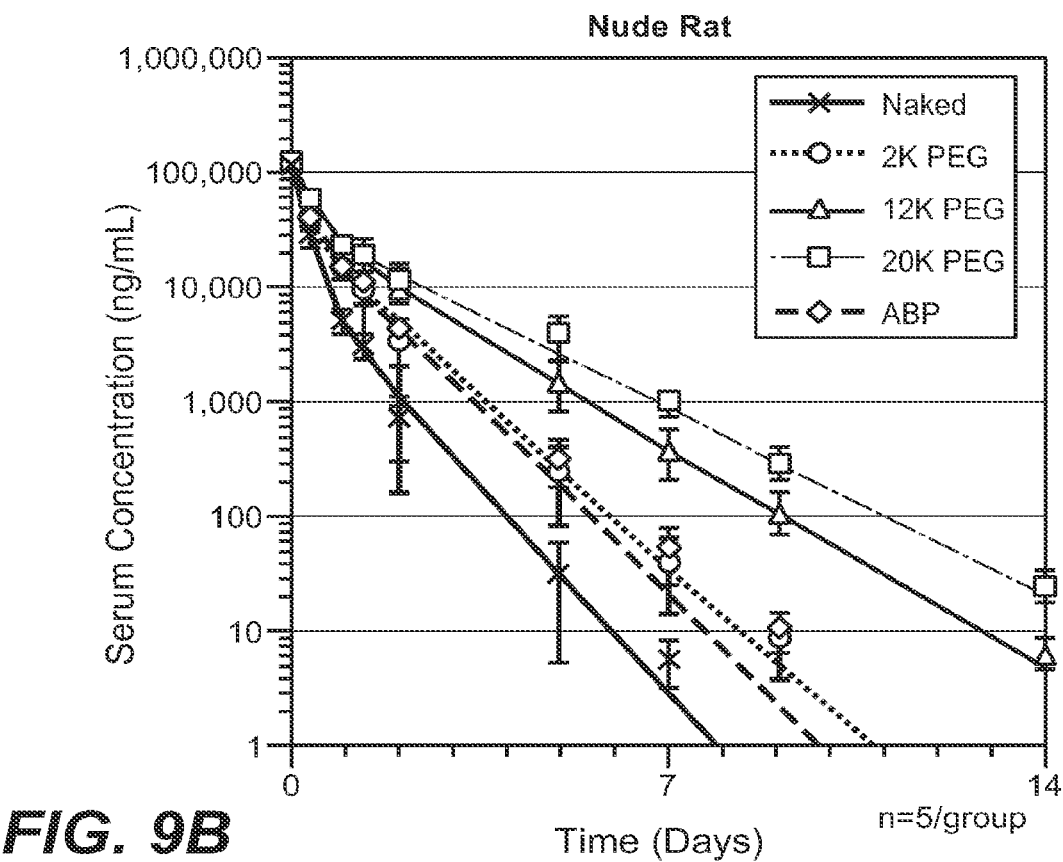

In both mice and rats, the addition of PEG to the bis-Fab lowered the rate of clearance of the molecule (FIGS. 9A-B, Table 4). The 2K PEGylation was observed to decrease the clearance by a factor of two (FIGS. 9A-B, Table 4). By adding a 20K PEG, the bis-Fab half-life could be extended to 30-35 hours (FIGS. 9A-B, Table 4). These results indicate that a range of dosing can be achieved for bis-Fabs and that the PK of the molecule can be modulated to accommodate different needs by varying the size of the PEG attached. The clearance of the un-PEGylated bis-Fab was approximately that expected for a F(ab')$_2$ and the 20K PEGylated bis-Fab possessed a half-life and clearance closer to an IgG. In addition, there was little difference in half-life between the 12K-bis-Fab and the 20K-bis-Fab (FIGS. 9A-B, Table 4) indicating that a larger PEG may not increase half life significantly. Finally, the ABP-bis-Fab half-lives were not significantly extended over the unmodified bis-Fabs in these experiments. (FIGS. 9A-B, Table 4). Additional pharmacokinetic data is presented in Table 4 below.

TABLE 4

Pharmacokinetic parameters based on two compartmental model.

| Treatment | Alpha_HL hours | AUC day*ng/mL | Beta_HL hours | CL mL/day/kg | Cmax ng/mL | V1 mL/kg | Vss mL/kg |
|---|---|---|---|---|---|---|---|
| MICE | | | | | | | |
| Unlabeled | 1.55 | 23239 | 10.8 | 215 | 99660 | 50.2 | 103.6 |
| 2 PEG | 5.85 | 41986 | 17.2 | 119 | 87946 | 56.9 | 74.2 |
| 12 PEG | 7.18 | 104356 | 27.7 | 47.9 | 161283 | 31.0 | 47.3 |
| 20 PEG | 6.78 | 91896 | 31.1 | 54.4 | 126336 | 39.6 | 66.9 |
| ABP | 2.94 | 47753 | 11.4 | 105 | 128186 | 39.0 | 56.3 |
| RATS | | | | | | | |
| Unlabeled | 4.1 | 30855 | 16.4 | 163.3 | N/A | 52.2 | 70.2 |
| 2 PEG | 5.0 | 49272 | 18.3 | 106 | N/A | 52.5 | 76.9 |
| 12 PEG | 6.1 | 83665 | 26.4 | 61.1 | N/A | 43.3 | 68.7 |
| 20 PEG | 4.7 | 96669 | 32.2 | 53.1 | N/A | 41.7 | 80.2 |
| ABP | 6.8 | 76078 | 19.2 | 70.6 | N/A | 43.2 | 51.4 |

Alpha_HL = alpha phase half-life;
Beta_HL = beta phase half-life;
AUC = area under the serum concentration-time curve to last observation point;
CL = clearance; Cmax = maximum observed concentration during the dosing period;
$V_{ss}$ = volume of distribution at steady state;
N/A = not available.

Bis-Fab in Vivo Activity

Figure 10A:
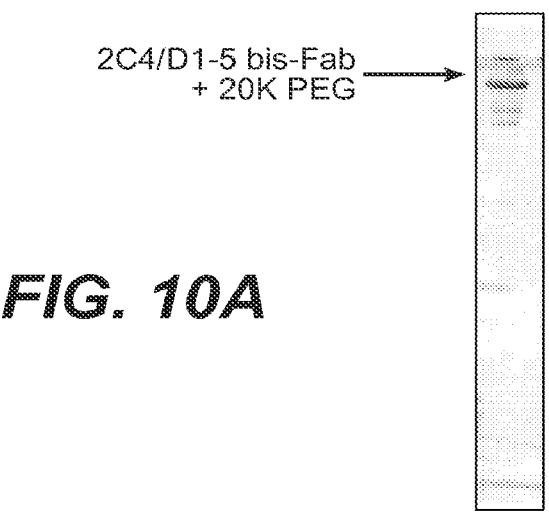
FIG. 10 shows SDS-PAGE analysis of purified 20K PEG-bis-Fab 2C4$^{V110C}$/D1-5$^{V110C}$ (A) and a cell growth inhibition assay using Calu3 cells (B) as described in Example 5.
Figure 10B:
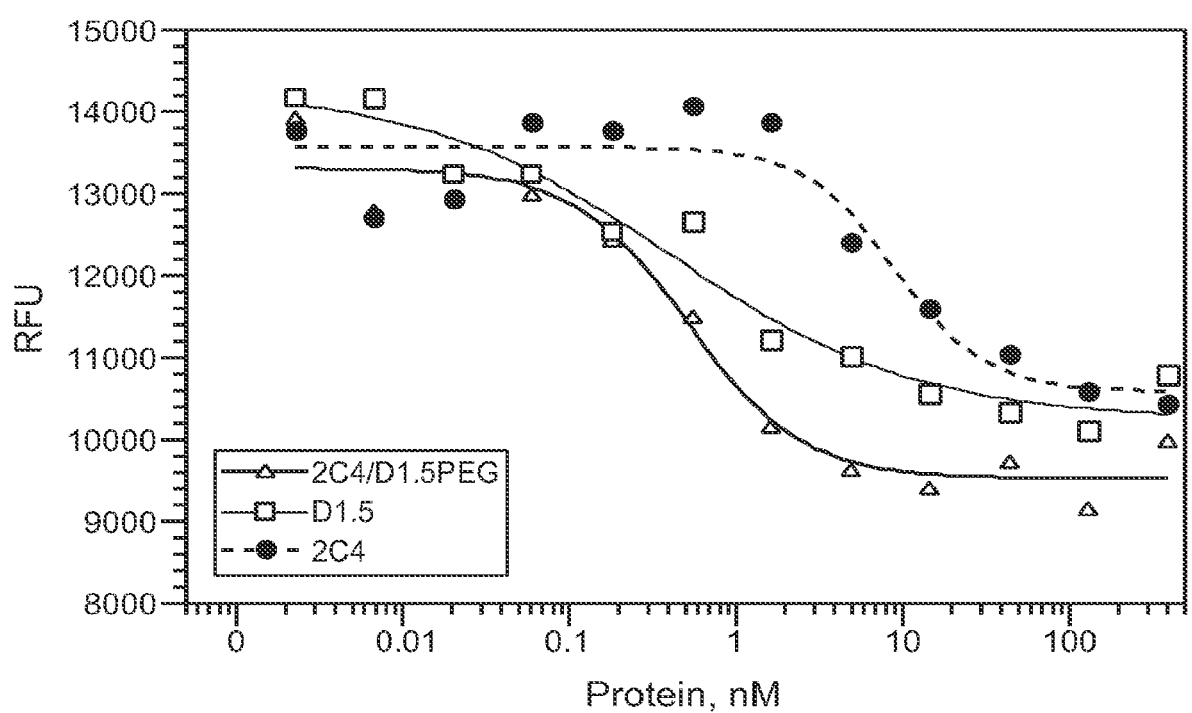

For in vivo mouse xenograft model studies, we constructed a PEGylated bis-Fab as follows. We first generated a BMata crosslinked bis-Fab containing a Her2-targeting thio-Fab, 2C4$^{V110C}$, and an EGFR (Her1)-targeting thio-Fab, D1-5$^{V110C}$. This BMata crosslinked bis-Fab was then reacted with hydroxylamine and a 1:1 molar equivalent of 20K mal-PEG to produce the PEGylated bis-Fab. The PEGylated bis-Fab was purified and analyzed by SDS-PAGE (FIG. 10A). The PEGylated bis-Fab was tested for its ability to inhibit proliferation of Calu3 cells in vitro. Calu3 cells are known to express both Her2 and EGFR (data not shown). For the assay, 8500 cells were seeded per well and treated with 2 nM heregulin and 5 nM TGFa. We then tested varying concentrations of bis-Fab and parent antibodies (concentrations indicated on the horizontal axis of FIG. 10B) for the ability to block ligand-stimulated cell growth. Alamar blue (25 µL) was added to each well and incubated at 37° C. for 3-4 hours. The plate was read in a fluorescent plate reader at 545/590 nm. The amount of cell proliferation was either reported directly in relative fluorescent units (RFUs) or by normalizing to controls. FIG. 10B shows that the PEGylated bis-Fab was a potent inhibitor of Calu3 proliferation in this experiment. Indeed it was more potent than either of the parent antibodies, 2C4 and D1-5.

Figure 11A:
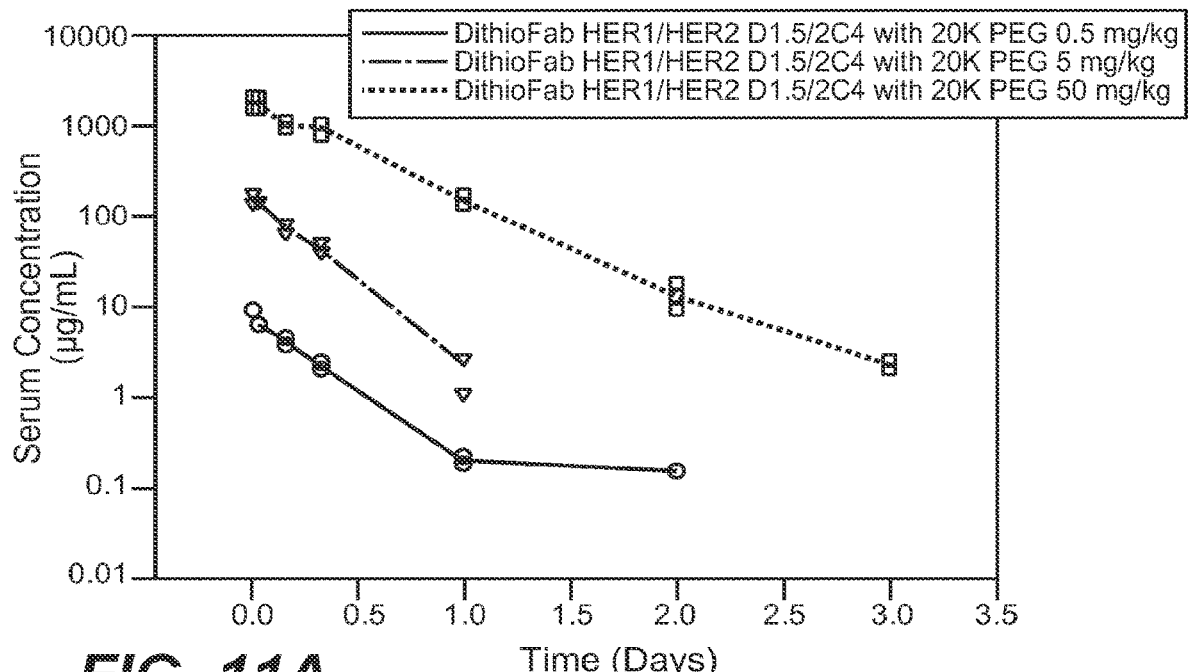
FIG. 11 shows a pharmacokinetic experiment of 20K PEG-2C4$^{V110C}$/D1-5$^{V110C}$ bis-Fab (dithioFab) in SCID Beige mice as described in Example 5. (A) Plot of serum concentration versus time; (B) Plot of serum concentration/dose versus time.
Figure 11B:
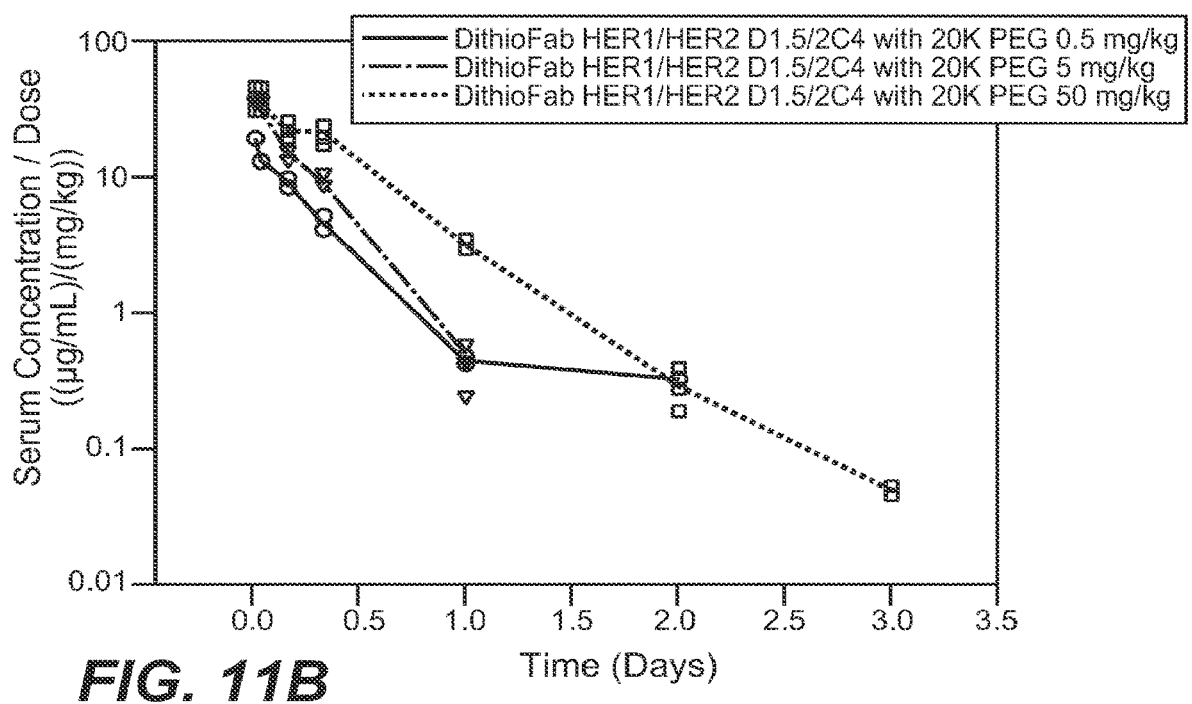

Next, we assessed the pharmacokinetics of the 20K PEG-2C4$^{V110C}$/D1-5$^{V110C}$ bis-Fab in SCID Beige mice. A similar ELISA-based capture assay as described above for the C3-101$^{V110C}$/Herc$^{V110C}$ bis-Fab was used to determine the amount of the molecule in serum. FIG. 11A shows the results plotted as serum concentration versus time while FIG. 11B shows the results plotted as serum concentration/dose versus time. The 20K PEG-2C4$^{V110C}$/D1-5$^{V110C}$ bis-Fab was cleared more rapidly from the scrum than the 20K-PEG-C3-101$^{V110C}$/Herc$^{V110C}$ bis-Fab (compare FIGS. 11A-B to FIG. 9A). We believe that host cross-reactivity accounts for the more rapid clearance of 20K PEG-2C4$^{V110C}$/D1-5$^{V110C}$ bis-Fab. Numerical data is presented in Table 5 below further illustrating the relatively short half-life of the 20K PEG-2C4$^{V110C}$/D1-5$^{V110C}$ bis-Fab in this experiment.

TABLE 5

Pharmacokinetic parameters.

| Dose (mg/kg) | HL-Lambda_z (hours) | CL$_{obs}$ (mL/day/kg) | AUC$_{inf\text{-}obs}$ normalized by dose |
|---|---|---|---|
| 0.5* | 4.61 | 200 | 5.01 |
| 5.0 | 3.84 | 102 | 9.81 |
| 50 | 7.27 | 53.1 | 18.8 |

*2 hr time point was excluded from the data analysis.
HL-Lambda_z refers to half-life associated with the elimination phase,
CL$_{obs}$ refers to observed clearance,
AUC$_{inf\text{-}obs}$ refers to observed area under the serum concentration-time curve extrapolated to infinity.

Figure 12:
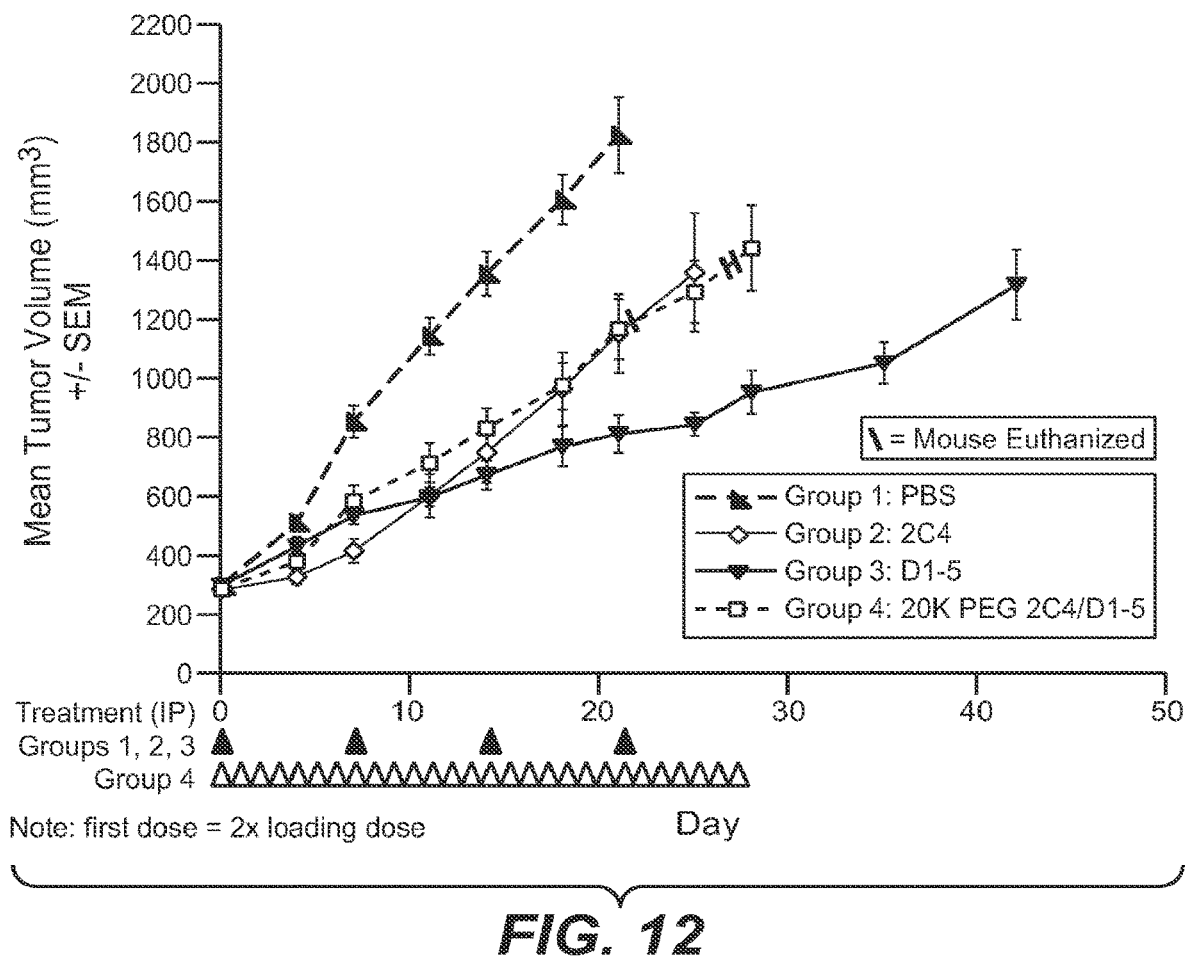
FIG. 12 shows the effect of 20K PEG-2C4$^{V110C}$/D1-5$^{V110C}$ bis-Fab and each of the parent antibodies, 2C4 and D1-5, on tumor cell growth in a Calu3 xenograft mouse model as described in Example 5.

We next examined the effects of the 20K PEG-2C4$^{V110C}$/D1-5$^{V110C}$ bis-Fab in comparison to the parent antibodies 2C4 and D1-5 in a Calu3 xenograft model in SCID Beige mice. We injected 5 million Calu3 cells/mouse followed by daily injections of 20K PEG-2C4$^{V110C}$/D1-5$^{V110C}$ bis-Fab (50 mg/kg), 2C4 (25 mg/kg), or D1-5 (25 mg/kg). Tumor volumes were measured periodically (timepoints indicated in FIG. 12) during the course of the experiment. The results shown in FIG. 12 indicate that the 20K PEG-2C4$^{V110C}$/D1-5$^{V110C}$ bis-Fab was effective at slowing the growth of tumors at this concentration, similar to the effectiveness observed with each parent antibody.

We then performed an expanded study to assess the effects of 20K PEG-2C4$^{V110C}$/D1-5$^{V110C}$ bis-Fab on tumor cell growth in the Calu3 xenograft mouse model described above and in comparison to the parent antibodies, 2C4 (pertuzumab) and D1-5. First, we analyzed the period of time it took for tumors to progress, defined as the time it took for tumors to double in size (2xVo) or the survival time if there was no tumor volume progression.

To carry out these experiments, 5 million Calu3 cells (suspended in HBSS) were inoculated subcutaneously into SCID beige mice (mice obtained from Charles River Labs, San Diego facility). The parent antibodies, 2C4 and D1-5 were dosed at 25 mg/kg (concentration of material was 5 mg/ml), IP, once per week for four weeks. The 20K PEG-2C4$^{V110C}$/D1-5$^{V110C}$ bis-Fab was dosed at 50 mg/kg (concentration of material was 7.5 mg/ml), IP once every day for 28 days. In all cases, the first dose was a 2x loading dose (i.e. 50 mg/kg 2C4 and D1-5 [concentration of material was 10 mg/ml] and 100 mg/kg 20K PEG-2C4$^{V110C}$/D1-5$^{V110C}$ bis-Fab [concentration of material was 7.5 mg/ml]).

Figure 13A:
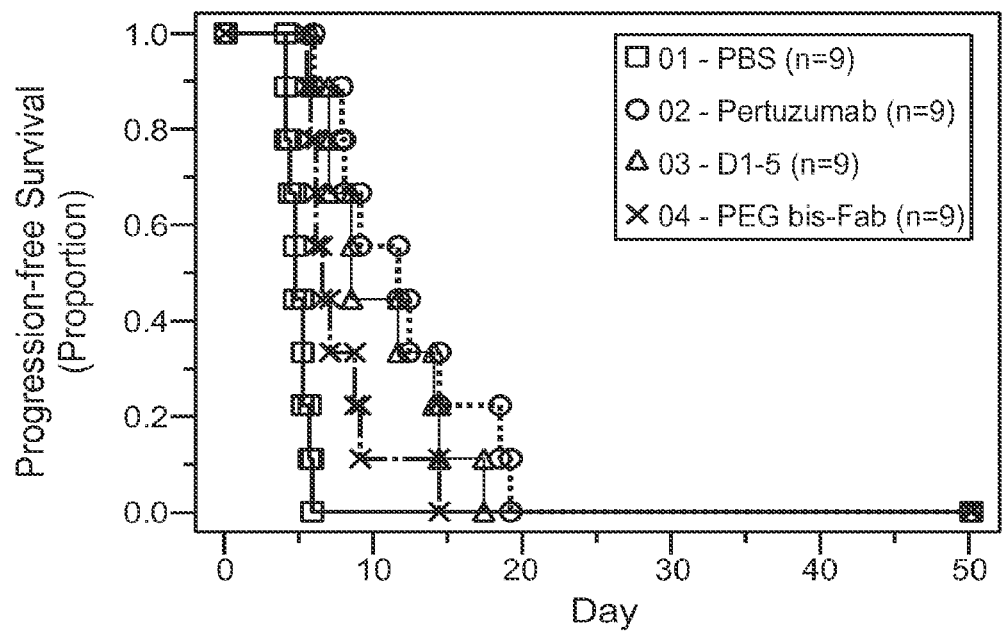
FIG. 13 shows the effect of 20K PEG-2C4$^{C110C}$/D1-5$^{V110C}$ bis-Fab and each of the parent antibodies, 2C4 and D1-5, on tumor cell growth in a Calu3 xenograft mouse model, analyzed as the time it took for tumors to double size (2× Vo) as described in Example 5. (A) Kaplan-Meier analysis; (B) oneway analysis.
Figure 13B:
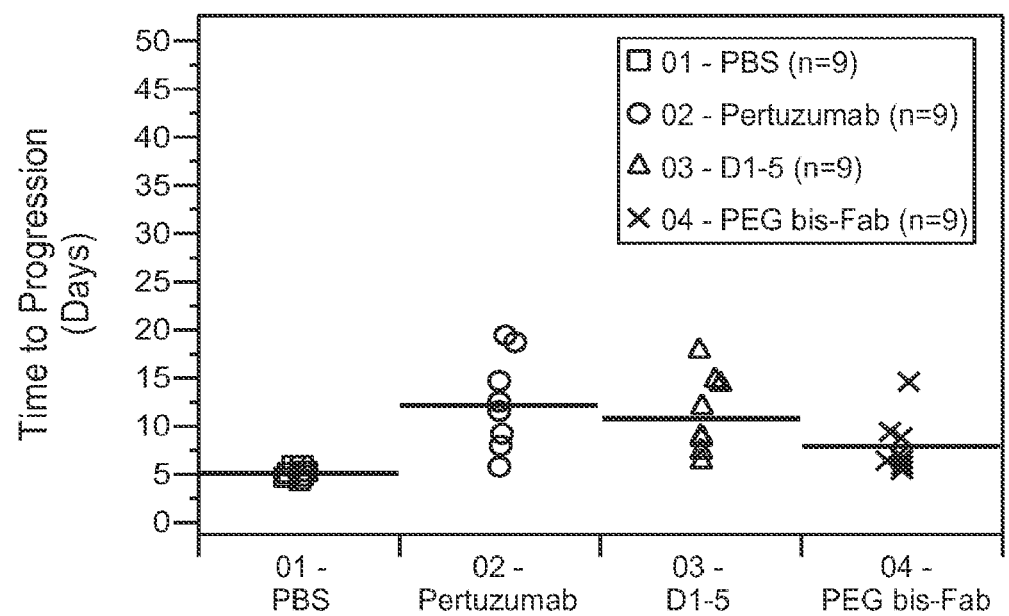
Figure 14A:
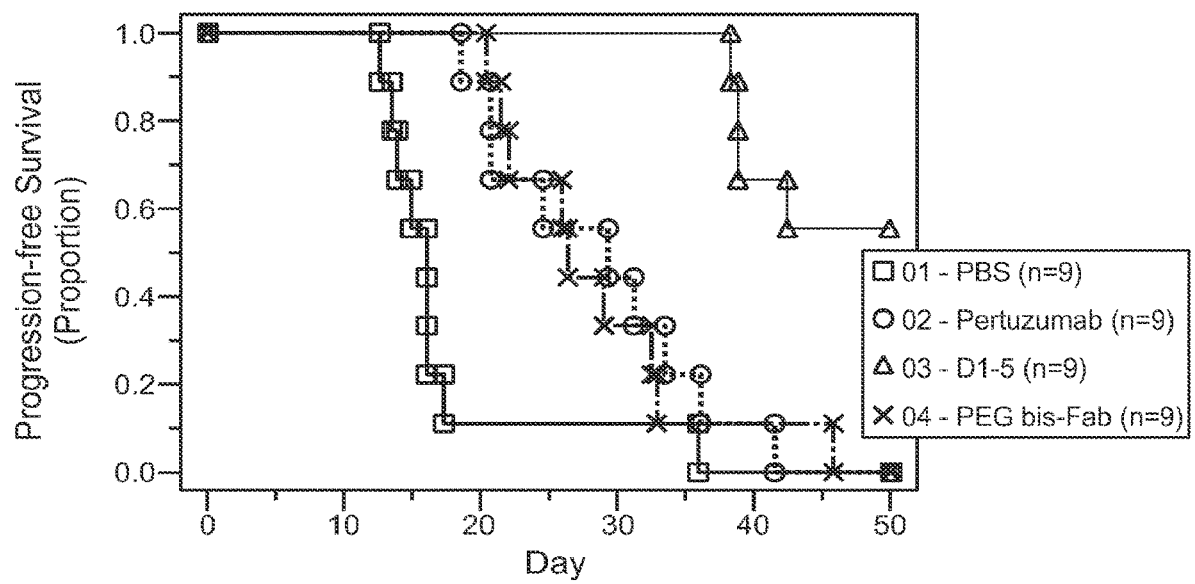
FIG. 14 shows the effect of 20K PEG-2C4$^{V110C}$/D1-5$^{V110C}$ bis-Fab and each of the parent antibodies, 2C4 and D1-5, on tumor cell growth in a Calu3 xenograft mouse model, analyzed as the time it took for tumors to reach a volume of 1500 mm³ as described in Example 5. (A) Kaplan-Meier analysis; (B) oneway analysis.
Figure 14B:
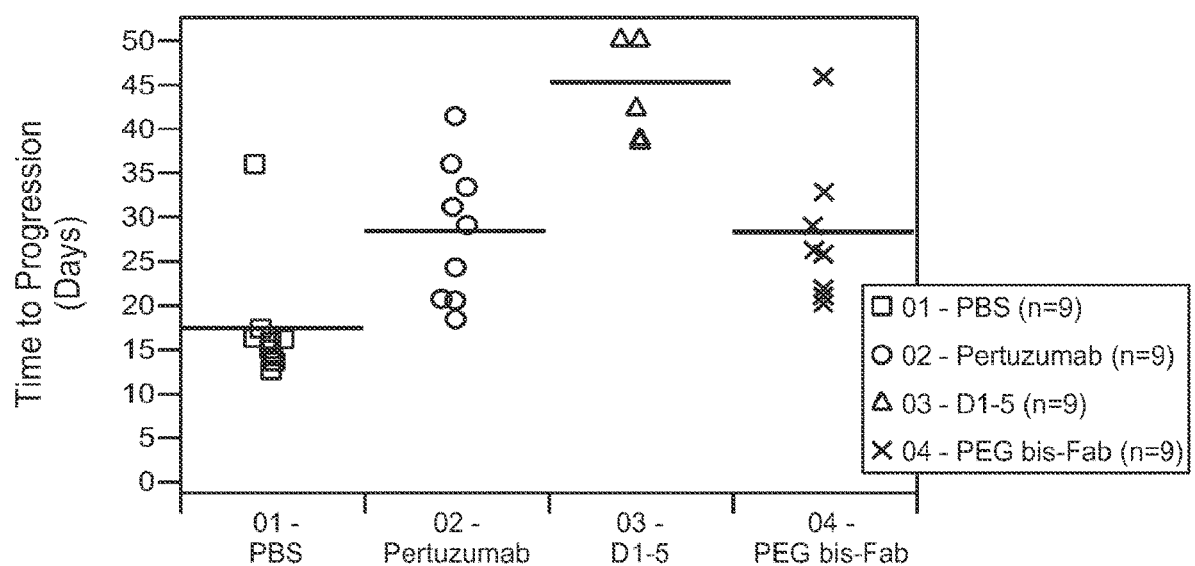

The Kaplan-Meier analysis is shown in FIG. 13A and the oneway analysis is shown in FIG. 13B. Second, we analyzed the period of time it took for tumors to progress, defined as the time it took for tumors to reach a volume of 1500 mm$^3$ or the survival time if there was no tumor volume progression. The Kaplan-Meier analysis is shown in FIG. 14A and the oneway analysis is shown in FIG. 14B. The results of these studies indicate that 20K PEG-2C4$^{V110C}$/D1-5$^{V110C}$ bis-Fab was effective at inhibiting tumor cell growth at the treatment dose, approaching the effectiveness of each of the parent antibodies. Accordingly, the bispecific antibody format described here is a useful platform for the development of therapeutic molecules.

Discussion

Her2 is involved in normal development and cell growth in heart, breast, and neural tissues, and is associated with the development of other organ systems. Falls, D. L. et al., *Exp Cell Res* 284(1):14-30 (2003); Casalini, P., et al., *J Cell Physiol* 200(3):343-50 (2004); Negro, A., et al., *Recent Prog Horm Res* 59:1-12 (2004); Britsch, S. *Adv Anat Embryol Cell Biol* 190:1-65 (2007). Most notable is the involvement of Her2 overexpression in breast cancer cell proliferation and the use of Her2 overexpression as a diagnostic marker for identifying breast cancer patients who will benefit from Herceptin® (trastuzumab). Lee, K. F., et al., *Nature* 378 (6555):394-8 (1995); Erickson, S. L., et al., *Development* 124(24):4999-5011 (1997); Britsch, S., et al., *Genes Dev* 12(12):1825-36 (1998); Morris, J. K., et al., *Neuron* 23(2): 273-83 (1999); Woldeyesus, M. T., et al., *Genes Dev* 13(19): 2538-48 (1999); Lin, W., et al., *Proc Natl Acad Sci USA* 97(3):1299-304 (2000); Park, S. K., et al., *J Cell Biol* 154(6):1245-58 (2001); Leu, M., et al., *Development* 130 (11):2291-301 (2003); Brufsky, A. *Am J Clin Oncol*. Aug. 11, 2009 (EPub PMID: 19675448). Herceptin® (trastuzumab) is a monoclonal antibody that binds to the fourth domain of the receptor's extracellular portion near the transmembrane region (Cho, H. S., et al., *Nature* 421(6924): 756-60 [2003]). Her2 is one of a family of four receptors that contribute to cell growth and development and are also targets for disease therapy (Casalini, P., et al., *J Cell Physiol* 200(3):343-50 [2004]). The coordinated effort of more that one receptor is often responsible for driving tumor cell growth (Yarden, Y. et al., *Nat Rev Mol Cell Biol* 2(2):127-37 (2001); Lee-Hoeflich, S. T., et al., *Cancer Res* 68(14): 878-87 [2008]). In this regard, the neutralization of the activity of more that one receptor may be desirable to provide a particularly effective therapy for certain cancers.

One approach to building and designing such molecules is to use bispecific antibody technologies, whereby a single antibody molecule possesses two unique monoclonal activities (Drakeman, D. L., et al., *Expert Opin Investig Drugs* 6(9): 1169-78 (1997); Kontermann, R. E. *Acta Pharmacol Sin* 26(1):1-9 (2005); Chames, P. et al., *Curr Opin Drug Discov Devel* 12(2):276-83 [2009]).

We developed the bis-Fab technology described herein at least in part as a means to screen for such molecules and to search for those that could provide increased efficacy over a single antibody or antibody combination. We have demonstrated here that the bis-Fab synthesis process is a robust and simple method to generate bispecific molecules. We determined that, in general, bis-Fab molecules possessed the combined biochemical activities of both parent antibodies. We observed a slight drop in cell-surface affinity with some bis-Fabs likely due to the monovalent structure of the molecules. This can be offset, however, in a number of ways. For example, bis-Fabs that target two receptors on the surface of one cell can be synthesized, two domains in the same receptor can be targeted, or the monovalent Fab affinity can be increased. The synthesis of a set of bis-Fabs targeting Her2 and EGFR using a matrix approach described here yielded highly pure molecules in sufficient quantity for various assays.

Using bis-Fabs in cell-based assays, we observed some unique activities. For example, the bis-Fab 1191 showed potent inhibition of cell proliferation with an uncharacteristically steep inhibition curve (FIG. 2C). An interesting aspect of this molecule is that it binds two different domains of Her2 simultaneously. The 2C4 arm of the bis-Fab targets domain II of the ECD and the Herc arm of the bis-Fab targets domain IV (Franklin, M. C., et al., *Cancer Cell* 5(4):317-28 (2004); Schmitz, K. R., et al., *Exp Cell Res* 315(4):659-70 [2009]). The curve appears cooperative and may suggest a mechanism of action that is unique to a molecule binding two domains in the same target. Such a molecule may offer advantages in efficacy over either single antibody or a combination of the two individual monoclonal antibodies in certain therapeutic settings.

Another more striking finding, however, was with trastuzumab thio-Fabs that were linked to each other to form the bis-Fab 1188. In this case, the bis-Fab is structurally similar to a single parent antibody except that it is lacking the Fc portion and the Fabs are covalently linked at a site that differs from the native hinge disulfide linkage. The bis-Fab 1188, Here $LC^{110Cys}$-Here $LC^{110Cys}$ showed an unexpected boost in cell proliferation, acting as an agonist instead of a potent antagonist (FIG. 2F). This was surprising because not only was the activity opposite to that of its structurally-similar parent antibody, but also because cell proliferation in BT474 cells overexpressing Her2 is not ligand-dependent and is considered to be maximally stimulated in the basal state. In addition, a different bis-Fab linking two 2C4 Fabs together had activity similar to its parent antibody (FIG. 2E). Without being bound by theory, it is likely that the different mechanism of action of the Fabs derived from different antibodies accounts for the different results observed with the bis-Fabs. Whereas 2C4 binds to domain II and inhibits the dimerization of Her2 with itself and other Her family members, trastuzumab appears to influence complex formation differently since domain IV is not a dimerization domain. The trastuzumab epitope is very close to the transmembrane region, a location where the antibody could have a significant impact of the orientation of the transmembrane regions effecting the orientation of two kinase domains (Cho, H. S., et al., *Nature* 421(6924):756-60 [2003]). Allosteric or other direct interactions with the kinase active site could be influenced by the binding of an antibody or bis-Fab to two receptor molecules in close proximity (Bocharov, E. V., et al., *J Biol Chem* 283(11):6950-6 (2008); Schmitz, K. R., et al., *Exp Cell Res* 315(4):659-70 [2009]).

Since the 1188 bis-Fab is a structural analog of Herceptin® (trastuzumab), we investigated whether changing the linkage attachment sites would alter the function of these molecules further. We also investigated the effects of thio-Fabs prepared from different sources. We showed that it was possible to obtain good results using the native antibody hinge region after digestion by pepsin. This allows one to use any antibody source as a starting point for building a bis-Fab without having to produce a mutant (cys-engineered) form of the molecule. Of course, because the thio-attachment point is limited to the hinge region, only certain structural variants can be produced. We also showed that good results could be obtained by using thio-Fabs derived from thio-Mabs prepared by proteolytic digestion with lysine-C. In addition, recombinant thio-Fabs were constructed, expressed in *E. coli*, purified, and used successfully to create bis-Fabs which also produced good results. Thus, all of these methods provide general opportunities for novel bis-Fab synthesis and discovery.

Our investigation into varying the linkages of Herc bis-Fabs led to the identification of a complete spectrum of activities that ranged from potent agonists, antagonists, and molecules that showed little effect on cell growth. Thus, it will be possible to identify molecules that possess activities different from the parent antibodies. Previously, changes in the hinge region of antibodies have been shown to impact antibody function (Dillon, T. M., et al., *J Biol Chem* 283 (23):16206-15 [2008]). It is not always possible to identify antibodies that possess the desired activity, whether activating or inhibitory, or to identify antibodies with varying levels of activity. Thus, the bis-Fab linkage variants offer an approach to further engineer the activity desired. In addition, previous studies with anti-CD20 antibodies have shown that subtle changes in the way the antibody interacts with the epitope can influence function (Ernst, J. A., et al., *Biochemistry* 44(46):15150-8 [2005]). A typical antibody engineering program could thus be extended to include covalent association of Fabs to help build more potent, effective therapeutic candidate molecules.

We also investigated certain physical and biochemical properties of bis-Fab agonists 1325 and 1188 in comparison to a potent bis-Fab antagonist, 1329, and Herceptin® (trastuzumab). We found no difference in the number of receptor binding sites on the surface of BT474 cells between the agonists and antagonists. Furthermore, there was no difference in the affinity of the molecules for the cell surface as determined by Scatchard analysis. The kD was about 3 nM for both types of molecules. We also assessed the molecular weight, retention by gel filtration, and the hydrodynamic radius of each of the molecules, but again we observed no gross differences in these physical properties. There was a minor trend towards the agonist molecules having a larger hydrodynamic radius by SEC-MALS analysis; however the observed differences were within the margin of error. One major analytical difference in the structure was observed on SDS-PAGE where these molecules, nearly identical in molecular weight, showed large migration differences on the gel. The denaturing conditions of SDS-PAGE did not correlate with our solution state analysis. For example, the differences observed on the gel did not reveal a pattern associated with activity because the most potent agonist, 1325, migrated between the extremes and similar to a potent antagonist, 1324. One major difference in these molecules is the orientation of the Fv regions relative to each other. This could account for the differing activities between the molecules. The present analysis did not reveal a predictive structure-function pattern, but a more detailed structure-function investigation may allow the design of a 3D-modeling approach to understanding the activity relationships. At present, functional variants of any antibody or antibody combination may be readily identified using an empirical approach based on the synthetic matrix process described here and functional activity assays available for the antibody(ies) of interest.

Using the most potent agonist derived from the trastuzumab thio-Fab combination matrix, 1325, we investigated the signaling pathway involved in propagating the cell proliferation signal. To test the signaling pathway we turned to the well characterized analysis of the activity of trastuzumab that has been recently reported. Here it has been shown that trastuzumab inhibits the interaction of Her2 and Her3 on cells that overexpress Her2 (Junttila, T. T., et al., Cancer Cell 15(5):429-40 [2009]). These two receptors are in a complex that recruits and activates PI3K in the basal state. The activation of this kinase results in the phosphorylation and activation of the key signaling kinase AKT. In our examination described above, AKT was phosphorylated to a much higher level in cells that were treated with the agonist bis-Fab 1325. This is something that we expected and consistent with the cell-proliferation signaling pathways known for Her2. What was different and unexpected was that the level of phosphorylation of Her3 did not change with the agonist addition. In fact, it appeared there was even a slight decrease in the phospho-tyrosine level in Her3 over the two hour time course. This suggests that the agonist may be bypassing the Her2/Her3 interaction to stimulate the activity of AKT. This could be accomplished by altering the phosphorylation state of Her2 directly. We probed the phosphorylation state of Her2 by mass spec analysis to look at individual phospho-peptides in the receptor intracellular domain (ICD). First, we identified several peptides that were phosphorylated in the basal state in BT474 cells. Then, we looked at the percentage phosphorylation of Her2 in response to either trastuzumab or 1325 agonist treatment. We observed that in total, several of these phosphorylation sites changed in response to the agonist but not in response to trastuzumab. It appears that the agonist further activates the receptor, but that this activation does not result in increased phosphorylation of Her3. This indicates that a slightly different activation complex may be propagating the signal and suggests that the bis-Fab 1325 may be useful to activate Her2 even in the absence of Her3 or a ligand.

Thus we investigated possible therapeutic areas where the activation of Her2 might be useful. An association between Herceptin® (trastuzumab) and the health of cardiac tissue has been documented. Chien, K. R. N Engl J Med 354(8): 789-90 (2006); Perik, P. J., et al., Eur J Heart Fail 9(2): 173-7 (2007); Suter, T. M., et al., J Clin Oncol 25(25):3859-65 (2007). During Herceptin® (trastuzumab) therapy cardiac toxicity can occur. In the presence of certain chemotherapy drugs, e.g., anthracyclines, the occurrence of cardiotoxicity during Herceptin® (trastuzumab) treatment has been shown to rise significantly (Morris, P. G., et al., Breast Cancer Res Treat DOI 10.1007/s10549-008-0172-5 (2008); Popat, S., et al., Nat Clin Pract Oncol 5(6):324-35 [2008]). Anthracycline alone is well understood to cause cardiotoxicity resulting in cardiomyopathy and congestive heart failure (Annals of Internal Medicine 125(1):47-58 [1996]). The damage associated with anthracycline and Herceptin® (trastuzumab) combined may be due to the disrupting of the normal function of Her2 in the natural repair process of damaged heart tissue. Thus, we reasoned that because of the effects sometimes observed on cardiac tissue in patients treated with Herceptin® (trastuzumab) and because Her2 activity is likely associated with heart cell growth (Freedman, N. J., et al., J Am Coll Cardiol 48(7): 1448-50 [2006]), it is possible that a Her2 agonist could benefit patients with heart disease. Recently it was shown definitively that, contrary to prior dogma, cardiac myocytes continue to proliferate during the course of adult life (Bergmann, O., R. et al., Science 324(5923):98-102 (2009); Bersell, K., S., et al., Cell 138(2):257-70 (2009); Doggen, K., et al., J Mol Cell Cardiol 46(1):33-8 [2009]). Accordingly, we suggest that trastuzumab-derived agonist bis-Fab molecules, such as bis-Fab 1325, may activate Her2 in growing adult cardiomyocytes thus providing a possible therapeutic lead for treatment of certain types of heart disease.

Several other cell types, tissues, and cellular processes are also dependent upon the activation of Her2 and other HER family members. These receptors are activated by the neuregulin family of ligands for which many important signaling functions have been observed. These cell types, tissues and processes include muscle cells, cardiac myocytes, Schwann cells, oligodendrocytes, neuromuscular synapse, cranial sensory neurons, motor and sensory neurons, peripheral and cranial nerves, sympathetic neurons, cortical neuron precursors, cerebellar granule cells, hypothalamus, parasympathetic tissue, hippocampus, heart tissue, development of cardiac valves, AV-septum, growth, repair and survival of cardiomyocytes, angiogenesis, development of pulmonary epithelium, myogenesis, gonadogenesis, and proliferation of gastric epithelium. Falls, D. L. Exp Cell Res 284(1):14-30 (2003); Falls, D. L. J. Neurocytol. 32(5-8):619-47 (2003); Britsch, S. Adv Anat Embryol Cell Biol 190:1-65 (2007). Accordingly, these cell types are additional potential targets for Her2 agonists. Additionally, the maintenance and differentiation of human embryonic stem cells (hECS) is dependent upon Her2 activity and could provide another important application of a Her2 agonist molecule (Jones, F. E., et al., Oncogene 18(23):3481-90 (1999); Leone, F., E., et al., J Leukoc Biol 74(4):593-601 (2003).

We have also investigated whether this technology is generally applicable by developing bis-Fabs to additional molecular targets. We synthesized bis-Fabs targeting FcγRIIb and FcεRIα and tested the effects of each on histamine release from RBL cells expressing both FcεRIα and FcγRIIb. The results showed that the different bis-Fabs displayed a range of activities.

In addition, we described a method for producing modified crosslinkers for use in the synthesis of bis-Fabs. We showed that such modified crosslinkers were useful for the addition of reagents useful for modifying in vivo half-life, such as PEG. We also showed the bis-Fabs containing PEG had an improved in vivo serum half-life compared to bis-Fabs lacking PEG. Finally, using in vivo mouse xenograft models, we showed that bis-Fabs containing PEG were effective at inhibiting tumor cell growth validating their potential as therapeutic candidates targeting solid tumors.

This new approach described here for the synthesis of antibody-like molecules, which we term bis-Fabs, can be a useful new tool in designing molecular therapies and assisting in basic research. As a screening method, this technology can be applied, for example, to the identification of the most useful bispecific antibody combination for a given application or as a tool for probing receptor signaling pathways. It is also useful for rapidly and robustly producing molecules for discovery and provides new opportunities to generate a wide range of activities that may otherwise not be possible with native immunoglobulin structures.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

We claim:

1. A method of synthesizing a panel of multispecific antibodies, the method comprising:
   (i) obtaining a first antigen binding fragment from a first parent antibody having a first monospecificity and a free sulfhydryl group;
   (ii) reacting the first antigen binding fragment with a thio-reactive crosslinker to produce an antigen binding fragment-crosslinker moiety; and
   (iii) reacting the antigen binding fragment-crosslinker moiety in different reaction mixtures with each of three or more additional antigen binding fragments obtained from one or more parent antibodies of different monospecificity from the first antigen binding fragment, wherein each of the three or more additional antigen binding fragments has a single free sulfhydryl group, and wherein the single free sulfhydryl groups of the additional antigen binding fragments are located at least at three different amino acid positions from each other,
thereby synthesizing the panel of isolated multispecific antibodies,
   wherein each multispecific antibody of the panel if isolated multispecific antibodies comprises the first antigen binding fragment crosslinked to the additional antigen binding fragment via single free sulfhydryl group pairs selected from the group consisting of:
   (a) position 110 of the light chain and position 110 of the light chain;
   (b) position 110 of the light chain and position 205 of the light chain;
   (c) position 110 of the light chain and position 118 of the heavy chain;
   (d) position 110 of the light chain and position 121 of the heavy chain;
   (e) position 110 of the light chain and a position in a hinge region;
   (f) position 205 of the light chain and position 205 of the light chain;
   (g) position 205 of the light chain and position 118 of the heavy chain;
   (h) position 205 of the light chain and position 121 of the heavy chain;
   (i) position 205 of the light chain and position in the hinge region;
   (j) position 118 of the heavy chain and position 118 of the heavy chain;
   (k) position 118 of the heavy chain and position 121 of the heavy chain;
   (l) position 118 of the heavy chain and a position in the hinge region;
   (m) position 121 of the heavy chain and position 121 of the heavy chain;
   (n) position 121 of the heavy chain and a position in the hinge region; and
   (o) a position in the hinge region and a position in the hinge region,
      wherein the numbering of the residues is according to the EU numbering system, and
wherein the first antigen binding fragment and the additional antigen binding fragments each comprise 6 CDRs.

2. The method of claim 1, wherein the first parent antibody is selected from the group consisting of an anti-Her1 antibody, an anti-Her2 antibody, an anti-FcεRIα antibody and anti-FcγRIIb antibody.

3. The method of claim 2, wherein the first antigen binding fragment is obtained from an anti-Her2 antibody and each of the two or more additional antigen binding fragments is obtained from anti-Her1 antibody, or the first antigen binding fragment is obtained from anti-Her1 antibody and each of the three more additional antigen binding fragments is obtained from anti-Her2 antibody, or the first antigen binding fragment is obtained from an anti-FcεRIα antibody and each of the three or more additional antibgen binding fragments is obtained from an anti-FcγRIIb antibody, or the first antigen binding fragment is obtained from anti-FcγRIIb antibody and each of the three or more additional antigen binding fragments is obtained from anti-FcεRIα antibody.

4. The method of claim 2, wherein the first parent antibody is an anti-Her2 antibody and is selected from the group consisting of trastuzumab and pertuzumab.

5. The method of claim 2, wherein the first parent antibody is an anti-Her1 antibody and is selected from the group consisting of D1-5 and C3-101.

6. The method of claim 1, wherein the first antigen binding fragment is obtained from an anti-Her2 antibody and the additional antigen binding fragments are obtained from an anti-Her1 antibody, and wherein the anti-Her2 antibody is trastuzumab or pertuzuamb and the anti-Her1 antibody is D1-5 or C3-101.

7. The method of claim 2, wherein the anti-FcγRIIb antibody is 5A6.

8. The method of claim 2, wherein the anti-FcεRIαantibody is 22E7.

9. The method of claim 3, wherein the anti-FcγRIIb antibody is 5A6 and the anti-FcεRIα antibody is 22E7.

10. The method of claim 1, wherein the thio-reactive crosslinker is selected from bis-maleimide, bis-alkyl halides, pyridyl disulfides, bis-mercurial salts, and bis-thiosulfonates.

11. The method of claim 10, wherein the thio-reactive crosslinker is bis-maleimide.

12. The method of claim 1, wherein the first antigen binding fragment or each of the three or more additional antigen fragments are obtained from a cysteine-engineered antibody.

13. The method of claim 12, wherein the cysteine-engineered antibody comprises a substitution at position 110 or at position 205 of the light chain, wherein the numbering of the residues is according to the EU numbering system, and wherein the substitution is cysteine.

14. The method of claim 12, wherein the cysteine-engineered antibody comprises a substitution at position 118 or at position 121 of the heavy chain, wherein the numbering of the residues is according to the EU numbering system, and wherein the substitution is cysteine.

15. A method of synthesizing a panel of antibody analogs, the method comprising:
(i) reacting a first antigen binding fragment having a free sulfhydryl group with a thio-reactive crosslinker to produce an antigen binding fragment-crosslinker moiety, and
(ii) reacting the antigen binding fragment-crosslinker moiety in different reaction mixtures with each of two or more additional antigen fragments,
wherein each of the two or more additional antigen binding fragments has a single free sulfhydryl group, and
wherein the single free sulfhydryl groups of each of the additional antigen binding fragments are located at least at two different amino acid positions from each other,
thereby synthesizing the panel of isolated antibody analogs,
wherein each of the first antigen binding fragment and the additional antigen binding fragments have the same monospecificity,
wherein each antibody analog of the panel of isolated antibody analogs comprises the first antigen binding fragment crosslinked to the additional antigen binding fragment via single free sulfhydryl group pairs selected from the group consisting of:
(a) position 110 of the light chain and position 110 of the light chain;
(b) position 110 of the light chain and position 205 of the light chain;
(c) position 110 of the light chain and position 118 of the heavy chain;
(d) position 110 of the light chain and position 121 of the heavy chain;
(e) position 110 of the light chain and a position in a hinge region;
(f) position 205 of the light chain and position 205 of the light chain;
(g) position 205 of the light chain and position 118 of the heavy chain;
(h) position 205 of the light chain and position 121 of the heavy chain;
(i) position 205 of the light chain and a position in a hinge region;
(j) position 118 of the heavy chain and position 118 of the heavy chain;
(k) position 118 of the heavy chain and position 121 of the heavy chain;
(l) position 118 of the heavy chain and a position in a hinge region;
(m) position 121 of the heavy chain and position 121 of the heavy chain;
(n) position 121 of the heavy chain and a position in a hinge region; and
(o) a position in the hinge region and a position in the hinge region,
wherein the numbering of the residues is according to the EU numbering system, and
wherein the first antigen binding fragment and the additional antigen binding fragments each comprise 6 CDRs.

16. The method of claim 15, wherein the antigen binding fragments bind to Her1, Her2, FcεRIα or FcγRIIb.

17. The method of claim 16, wherein the parent antibodies of the antigen binding fragments are selected from the group consisting of trastuzumab and pertuzumab, and cysteine engineered fragments thereof.

18. The method of claim 16, wherein the parent antibodies of the antigen binding fragments are selected from the group consisting of D1-5 and C3-101, and cysteine engineered fragments thereof.

19. The method of claim 16, wherein the anti-FcγRIIb antibody is 5A6.

20. The method of claim 16, wherein the anti-FcεRIα antibody is 22E7.

21. The method of claim 15, wherein the thio-reactive chemical crosslinker is selected from the group bis-maleimide halides, bis-alkyl halides, pyridyl disulfides, bis-mercurial salts, and bis-thiosulfonates.

22. The method of claim 21, wherein the thio-reactive chemical crosslinker is bis-maleimide.

23. The method of claim 15, wherein the first antigen binding fragment or each of the two or more additional antigen binding fragments are obtained from a cysteine-engineered antibody.

24. The method of claim 23, wherein the cysteine-engineered antibody comprises a substitution at position 110 or at position 205 of the light chain, wherein the numbering of the residues is according to the EU numbering system, and wherein the substitution is cysteine.

25. The method of claim 23, wherein the cysteine-engineered antibody comprises a substitution at position 118 or at position 121 of the heavy chain, wherein the numbering of the residues is according to the EU numbering system, and wherein the substitution is cysteine.

26. The method of claim 1, comprising
   (i) obtaining two or more first antigen binding fragments from a parent antibody having a first monospecificity and single free sulfhydryl groups,
   (ii) reacting the first antigen binding fragments with a thio-reactive crosslinker to produce antigen binding fragment-crosslinker moieties, and
   (iii) reacting the antigen binding fragment-crosslinker moieties with each of three or more additional antigen binding fragments obtained from one or more parent antibodies of different monospecificity from the first antigen binding fragments, each having a single free sulfhydryl group,
   thereby synthesizing the panel of isolated multispecific antibodies,
      wherein the single free sulfhydryl groups of each of the first antigen binding fragments are located at least at two different amino acid positions from each other,
   wherein each multispecific antibody of the panel of isolated multispecific antibodies comprises the first antigen binding fragment crosslinked to the additional antigen binding fragment via single free sulfhydryl group pairs selected from the group consisting of:
      (a) position 110 of the light chain and position 110 of the light chain;
      (b) position 110 of the light chain and position 205 of the light chain;
      (c) position 110 of the light chain and position 118 of the heavy chain;
      (d) position 110 of the light chain and position 121 of the heavy chain;
      (e) position 110 of the light chain and a position in the hinge region;
      (f) position 205 of the light chain and position 205 of the light chain;
      (g) position 205 of the light chain and position 118 of the heavy chain;
      (h) position 110 of the light chain and position 121 of the heavy chain;
      (i) position 110 of the light chain and a position in the hinge region;
      (j) position 118 of the heavy chain and position 118 of the heavy chain;
      (k) position 118 of the heavy chain and position 121 of the heavy chain;
      (l) position 118 of the heavy chain and a position in the hinge region;
      (m) position 121 of the heavy chain and position 121 of the heavy chain;
      (n) position 121 of the heavy chain and a position in the hinge region; and
      (o) a position in the hinge region and a position in the hinge region,
         wherein the numbering of the residues is according to the EU numbering system, and
      wherein the first antigen binding fragments and the additional antigen binding fragments each comprise 6 CDRs.

27. The method of claim 1, further comprising purifying the antigen binding fragment-crosslinker moiety prior to reacting the antigen binding fragment-crosslinker moiety with each of three or more additional antigen binding fragments.

28. A method of synthesizing a panel of isolated multispecific antibodies, the method comprising:
   (i) obtaining a first antigen binding fragment from a first parent antibody having a first monospecificity and a single free sulfhydryl group;
   (ii) reacting the first antigen binding fragment with a thio-reactive crosslinker to produce an antigen binding fragment-crosslinker moiety; and
   (iii) reacting the antigen binding fragment-crosslinker moiety in different reaction mixtures with each of two or more additional antigen binding fragments obtained from one or more parent antibodies of different monospecificity from the first antigen binding fragment,
      wherein each of the two or more additional antigen binding fragments has a single free sulfhydryl group, and
      wherein the single free sulfhydryl groups of each of the additional antigen binding fragments are located at least at two different amino acid positions from each other,
   thereby synthesizing the panel of isolated multispecific antibodies,
      wherein each multispecific antibody of the panel of isolated multispecific antibodies comprises the first antigen binding fragment crosslinked to the additional antigen binding fragment via single free sulfhydryl group pairs selected from the group consisting of:
         (a) position 110 of the light chain and position 110 of the light chain;
         (b) position 110 of the light chain and position 205 of the light chain;
         (c) position 110 of the light chain and position 118 of the heavy chain;
         (d) position 110 of the light chain and position 121 of the heavy chain;
         (e) position 110 of the light chain and a position in a hinge region;
         (f) position 205 of the light chain and position 205 of the light chain;
         (g) position 205 of the light chain and position 118 of the heavy chain;
         (h) position 205 of the light chain and position 121 of the heavy chain;
         (i) position 205 of the light chain and a position in a hinge region;
         (j) position 118 of the heavy chain and position 118 of the heavy chain;
         (k) position 118 of the heavy chain and position 121 of the heavy chain;

(l) position 118 of the heavy chain and a position in a hinge region;

(m) position 121 of the heavy chain and position 121 of the heavy chain;

(n) position 121 of the heavy chain and a position in the hinge region; and (o) a position in the hinge region and a position in the hinge region, wherein the numbering of the residues is according to the EU numbering system, and wherein the first antigen binding fragment and the two or more additional antigen binding fragments each comprise 6 CDRs.

29. The method of claim 1, further comprising testing each of the multispecific antibodies for a multispecific antibody having a desired activity.

30. The method of claim 15, further comprising testing each of the antibody analogs for an antibody analog having a desired activity.

* * * * *

UNITED STATES PATENT AND TRADEMARK OFFICE
CERTIFICATE OF CORRECTION

PATENT NO. : 10,584,181 B2
APPLICATION NO. : 13/510145
DATED : March 10, 2020
INVENTOR(S) : Justin Scheer et al.

It is certified that error appears in the above-identified patent and that said Letters Patent is hereby corrected as shown below:

In the Claims

In Claim 1:

At Column 149, Line 36:
Please change "panel of" to --panel of isolated--

At Column 149, Line 39:
Please change "free sulfhydryl group" to --single free sulfhydryl group--

At Column 149, Line 59:
Please replace "if" with --of--

At Column 150, Line 48:
Please change "position" to --a position--

In Claim 2:

At Column 151, Line 4:
Please change "antibody and" to --antibody and an--

In Claim 3:

At Column 151, Line 7:
Please change "two" to --three--

At Column 151, Line 8:
Please change "anti-Her1 antibody" to --an anti-Her1 antibody--

Signed and Sealed this
Fourth Day of August, 2020

Andrei Iancu
*Director of the United States Patent and Trademark Office*

At Column 151, Line 9:
Please change "anti-Her1 antibody" to --an anti-Her1 antibody--

At Column 151, Line 11:
Please change "anti-Her1 antibody" to --an anti-Her1 antibody--

At Column 151, Line 13:
Please change "antibgen" to --antigen--

At Column 151, Line 16:
Please change "anti-FcγRIIb antibody" to --an anti-FcγRIIb antibody--

At Column 151, Line 17:
Please change "anti-FcεRIα antibody" to --an anti-FcεRIα antibody--

In Claim 6:

At Column 151, Line 30:
Please change "pertuzuamb" to --pertuzumab--

In Claim 10:

At Column 151, Line 40:
Please change "from bis-maleimide" to --from the group consisting of bis-maleimide--

In Claim 12:

At Column 151, Line 47:
Please change "antigen" to --antigen binding--

In Claim 15:

At Column 151, Line 59:
Please change "antibody" to --isolated antibody--

At Column 151, Line 60:
Please change "single" to --single free--

At Column 151, Line 62:
Please change "crosslinker" to --chemical crosslinker--

At Column 151, Line 67:
Please change "antigen" to --antigen binding--

At Column 152, Line 35:
Please change "a" to --the--

At Column 152, Line 42:
Please change "a hinge" to --the hinge--

At Column 152, Line 46:
Please change "a hinge" to --the hinge--

In Claim 17:

At Column 152, Line 56:
Please change "the parent" to --parent--

In Claim 18:

At Column 152, Line 60:
Please change "the parent" to --parent--

In Claim 21:

At Column 153, Line 3:
Please change "bis-maleimide halides," to --bis-maleimide,--

In Claim 28:

At Column 154, Line 62:
Please change "a hinge" to --the hinge--

At Column 155, Line 2:
Please change "a hinge" to --the hinge--